US008071549B2

(12) United States Patent
Kiselyov et al.

(10) Patent No.: US 8,071,549 B2
(45) Date of Patent: Dec. 6, 2011

(54) COMPOUNDS CAPABLE OF AFFECTING DIFFERENTIATION, PROLIFERATION, REGENERATION, PLASTICITY AND SURVIVAL CELLS

(76) Inventors: Vladislav V Kiselyov, Copenhagen Ø (DK); Galina Skladchikova, Hellerup (DK); Vladimir Berezin, Copenhagen N (DK); Elisabeth Bock, Charlottenlund (DK)

( * ) Notice: Subject to any disclaimer, the term of this patent is extended or adjusted under 35 U.S.C. 154(b) by 0 days.

(21) Appl. No.: 12/435,043

(22) Filed: May 4, 2009

(65) Prior Publication Data

US 2009/0305951 A1 Dec. 10, 2009

Related U.S. Application Data

(63) Continuation of application No. 10/486,731, filed as application No. PCT/DK02/00541 on Aug. 19, 2002, now abandoned.

(30) Foreign Application Priority Data

Aug. 17, 2001 (DK) .............................. 2001 01228
May 2, 2002 (DK) .............................. 2002 00667

(51) Int. Cl.
*A61K 38/00* (2006.01)
*C07K 14/78* (2006.01)
*C07K 14/705* (2006.01)

(52) U.S. Cl. .......... 514/19.1; 514/7.5; 514/8.3; 514/9.1; 514/13.3; 530/300; 530/327

(58) Field of Classification Search ........................ None
See application file for complete search history.

(56) References Cited

U.S. PATENT DOCUMENTS

| | | | |
|---|---|---|---|
| 4,599,311 A | 7/1986 | Kawasaki | |
| 4,683,202 A | 7/1987 | Mullis | |
| 5,010,175 A | 4/1991 | Rutter et al. | |
| 5,223,409 A | 6/1993 | Ladner et al. | |
| 5,693,488 A * | 12/1997 | Fang et al. | ................ 435/69.1 |
| 5,837,813 A | 11/1998 | Ruoslahti et al. | |
| 5,840,689 A * | 11/1998 | Daniloff | ................ 514/12 |
| 6,313,265 B1 | 11/2001 | Phillips et al. | |
| 6,576,607 B1 | 6/2003 | Schachner | |
| 6,749,850 B1 | 6/2004 | Finkelstein et al. | |
| 7,167,819 B1 * | 1/2007 | Gibson et al. | ................ 703/12 |
| 7,504,490 B1 * | 3/2009 | Weinstock et al. | ................ 536/23.1 |
| 2009/0105149 A1 | 4/2009 | Albrechtsen et al. | |

FOREIGN PATENT DOCUMENTS

| | | |
|---|---|---|
| WO | WO 00/18791 | 4/2000 |
| WO | WO 00/24770 | 5/2000 |
| WO | WO 01/16166 | 3/2001 |
| WO | WO 01/96364 | 12/2001 |
| WO | WO 03/016351 | 2/2003 |
| WO | WO 2004/056865 | 7/2004 |

OTHER PUBLICATIONS

Kolkova et al., Journal of Neuroscience, Mar. 15, 2000, 20(6):2238-2246.*
Dickson, et al., "Human Muscle Neural Cell Adhesion Molecule (N-CAM): Identification of a Muscle-Specific Sequence in the Extracellular Domain", *Cell*, vol. 50, pp. 1119-1130, Sep. 25, 1987.
Rønn, et al., "Neurite Outgrowth Induced by a Synthetic Peptide Ligand of Neural Cell Adhesion Molecule Requires Fibroblast Growth Factor Receptor Activation", *Journal of Neurochemistry*, vol. 75, pp. 665-671, 2000.
Stahlhut, et al., "NCAM-Fibronectin-Type-III-Domain Substrata With and Without a Six-Amino-Acid-Long Proline-Rich Insert Increase the Dendritic and Axonal Arborization of Spinal Motoneurons", *Journal of Neuroscience Research*, vol. 48, pp. 112-121, 1997.
USPTO, Final Rejection, mailed Jan. 18, 2011 on Application of Albrechtsen, U.S. Appl. No. 10/567,365.
U.S. Appl. No. 12/745,129, filed May 27, 2001, Berezin, et al.
Alber et al., "Nucleotide Sequence of the Triose Phosphate Isomerase Gene of *Saccharomyces cerevisiae*", *J. of Molecular and Applied Genetics*, vol. 1, No. 5, pp. 419-434, 1982.
Altman et al., "Postnatal Development of Locomotion in the Laboratory Rat", *Anim. Behav.*, vol. 23, pp. 896-920, 1975.
Beaucage et al., "Deoxynucleoside Phosphoramidites—A New Class of Key Intermediates forDeoxypolynucleotide Synthesis", *Tetrahedron Letters*, vol. 22, No. 20, pp. 1859-1862, 1981.
Bruses, et al., "Roles, regulation, and mechanism of polysialic acid function during neural development", *Biochemie*, vol. 83, pp. 635-643, 2001.
Cambon et al., "A Synthetic Neural Cell Adhesion Molecule Mimetic Peptide Promotes Synaptogenesis. Enhances Presynaptic Function, and Facilitates Memory Consolidation", *J. of Neuroscience*, vol. 24, No. 17, pp. 4197-4204, Apr. 28, 2004.
Cancilla et al., "Fibroblast growth factor receptors and their ligands in the adult rat kidney", *Kidney International*, vol. 60, pp. 147-155, 2001.
Castelnau et al., "Prion Protein Gene Expression in Cultured Astrocytes Treated by Recombinant Growth Hormone and Insulin-like Growth Factor", *Experimental Neurology*, vol. 130, pp. 407-410, 1994.
Cerbone et al., "Behavioral Habituation to Spatial Novelty: Interference and Noninterference Studies", *Neuroscience and Behavioral Reviews*, vol. 18, No. 4, pp. 497-518, 1994.
Cheng et al., "NGF and bFGF Protect Rat Hippocampal and Human Cortical Neurons against Hypoglycemic Damage by Stabilizing Calcium Homeostasis", *Neuron*, vol. 7, pp. 1031-1041, Dec. 1991.

(Continued)

*Primary Examiner* — Daniel C Gamett
(74) *Attorney, Agent, or Firm* — Iver P. Cooper

(57) ABSTRACT

The present invention relates to a compound comprising the third Immunoglobulin (Ig3) module, and/or the fourth Immunoglobulin (Ig4) module, and/or the fifth immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, capable of interacting with an Fibroblast Growth Factor (FGF) receptor and/or Adenosine-Tri-Phosphate (ATP) and/or L1, and thereby the compounds are capable of inducing differentiation, modulating proliferation, stimulate regeneration, neuronal plasticity and/or survival of cells. Further, the present invention relates to a pharmaceutical composition comprising said compound, a process of producing a pharmaceutical composition and the use of said compound.

60 Claims, 13 Drawing Sheets

OTHER PUBLICATIONS

Figure 1:
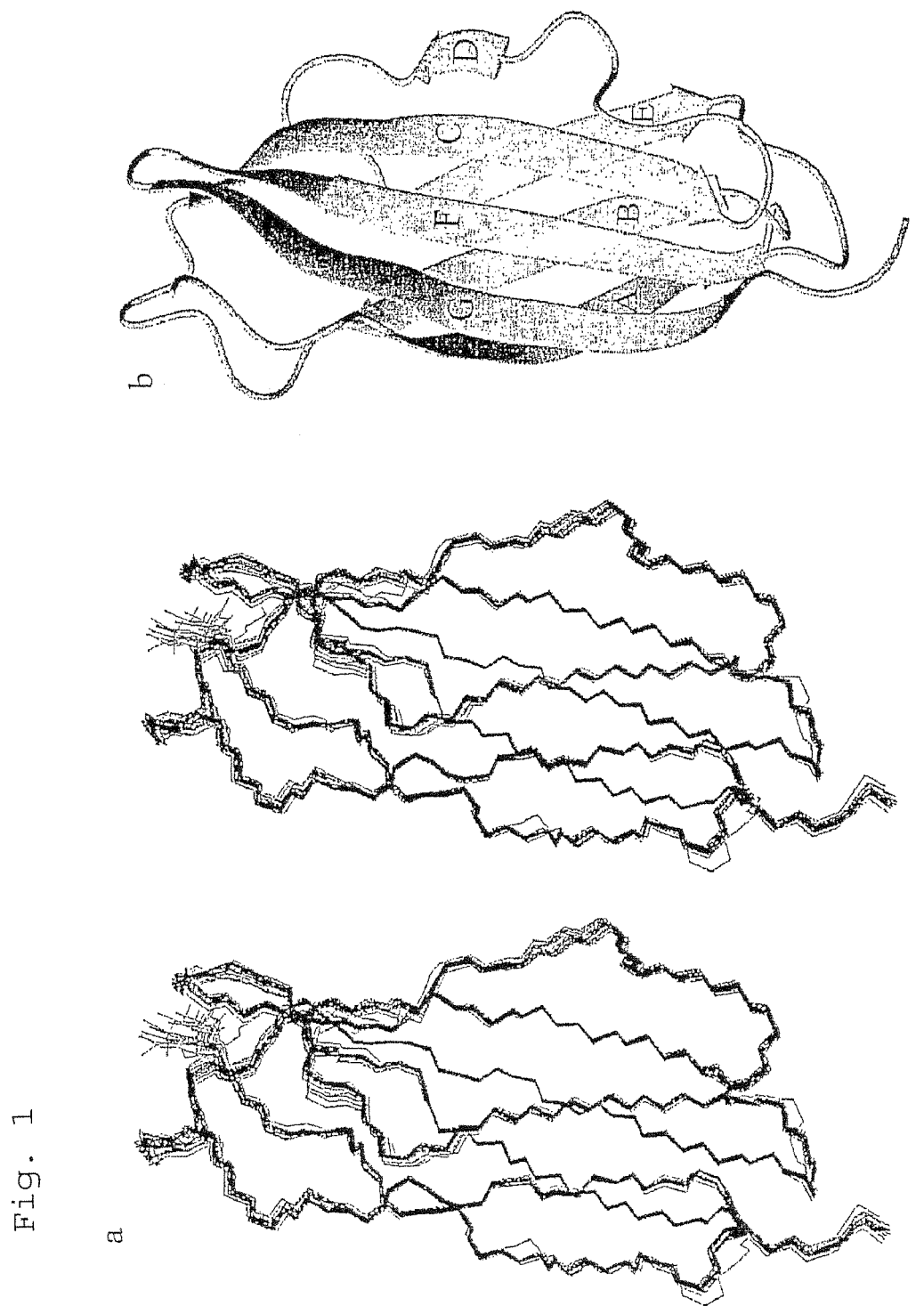

Clayton et al., "Noradrenergic Receptor Blockade of the NTS Attenuates the Mnemonic Effects of Epinephrine in an Appetitive Light-Dark Discrimination Learning Task", *Neurobiology of Learning and Memory*, vol. 74, pp. 135-145, 2000.

Cordero et al., "Prior exposure to a single stress session facilitates subsequent contextual fear conditioning in rats—Evidence for a role of Corticosterone", *Hormones and Behavior*, vol. 44, pp. 338-345, 2003.

Corsaro et al., "Enhancing the Efficiency of DNA-Mediated Gene Transfer in Mammalian Cells", *Somatic Cell Genetics*, vol. 7, No. 5, pp. 603-616, 1981.

Cotman et al., "Cell Adhesion Molecules in Neural Plasticity and Pathology: Similar Mechanisms, Distinct Organizations", *Progress in Neurobiology*, vol. 55, pp. 659-669, 1998.

Cremer, et al., "NCAM is essential for axonal growth and fasciculation in the hippocampus", *Mol. Cell Neurosci.*, vol. 8, pp. 323-335, 1997.

D'Mello et al., "Induction of apoptosis in cerebellar granule neurons by low potassium: Inhibition of death by insulin-like growth factor I and cAMP", *Proc. Natl. Acad. Sci. USA*, vol. 90, pp. 10989-10993, Dec. 1993.

Dantzer, et al., "Modulation of social memory in male rats by neurohypophyseal peptides", *Psychopharmacology*, vol. 91, pp. 363-368, 1987.

Defoort et al., "A rational design of synthetic peptide vaccine with a built-in adjuvant", *Int. J. Peptide Protein Res.*, vol. 40, pp. 214-221, 1992.

Delobette et al., "In vitro aggregation facilitates β-amyloid peptide-(25-35)-induced amnesia in the rat", *European J. of Pharmacology*, vol. 319, pp. 1-4, 1997.

Devlin, et al., "Random Peptide Libraries: A Source of Specific Protein Binding Molecules", *Science*, vol. 249, pp. 404-406, Jul. 27, 1990.

Dickson, et al., "Human Muscle Neural Cell Adhesion Molecule (N-CAM): Identification of a Muscle-Specific Sequence in the Extracellular Domain", *Cell*, vol. 50, pp. 1119-1130, Sep. 25, 1987.

Drejer et al., "Selection of a Pure Cerebellar Granule Cell Culture by Kainate Treatment", *Neurochemical Research*, vol. 14, No. 8, pp. 751-754, 1989.

Drijfhout et al., "A new synthetic functionalized antigen carrier", *Int. J. Peptide Protein Res.*, vol. 37, No. 27-32, 1991.

Dryland et al., "Peptide Synthesis. Part 8. A System for Solid-phase Synthesis Under Low Pressure Continuous Flow Conditions", *J. Chem. Soc Perkin Trans. I*, pp. 125-137, 1986.

Eldadah et al., "Ribozyme-Mediated Inhibition of Caspase-3 Protects Cerebellar Granule Cells from Apoptosis Induced by Serum-Potassium Deprivation", *J. Neuroscience*, vol. 20, No. 1, pp. 179-186, Jan. 1, 2000.

Fodor, et al., "Light-Directed, Spatially Addresable Parallel Chemical Synthesis", *Science*, vol. 251, pp. 767-773, Feb. 15, 1991.

Goodwin et al., "A simple procedure for solid-phase synthesis of peptide nucleic acids with N-terminal cysteine", *Bioorganic & Medicinal Chemistry Letters*, vol. 8, pp. 2231-2234, 1998.

Geysen, et al., "Use of peptide synthesis to probe viral antigens for epitopes to a resolution of a single amino acid", *Proc. Natl. Acad. Sci. USA*, vol. 81, pp. 3998-4002, Jul. 1984.

Geysen, et al., "Chemistry of Antibody Binding to a Protein", *Science*, vol. 235, pp. 1184-1190, Mar. 6, 1987.

Geysen, et al., "Strategies for epitope analysis using peptide synthesis", *Journal of Immunological Methods*, vol. 102, pp. 259-274, 1987.

Graham et al., "A New Technique for the Assay of Infectivity of Human Adenovirus 5 DNA", *Virology*, vol. 52, pp. 456-467, 1973.

Hart et al., "Attenuation of FGF signaling in mouse β-cells leads to diabetes", *Nature*, vol. 408, pp. 864-868, Dec. 14, 2000.

Henck et al., "Growth and Development in Rats Given Recombinant Human Epidermal Growth Factor $_{1-48}$ as Neonates", *Toxicological Sciences*, vol. 62, pp. 80-91, 2001.

Hitzeman et al., "Isolation and Characterization of the Yeast 3-Phosphoglycerokinase Gene (PGK) by an Immunological Screening Technique", *J. of Biol. Chem.*, vol. 255, No. 24, pp. 12073-12080, Dec. 25, 1980.

Houghten, et al., "Generation and use of synthetic peptide combinatorial libraries for basic research and drug discovery", *Nature*, vol. 354, pp. 84-86, Nov. 7, 1991.

Jungnickel et al., "Fibroblast growth factor receptor 3 signaling regulates injury-related effects in the peripheral nervous system", *Mol. Cell. Neurosci.*, vol. 25, pp. 21-29, 2004.

Kaufman et al., "Amplification and Expression of Sequences Cotransfected with a Modular Dihydrofolate Reductase Complementary DNA Gene", *J. Mol. Biol.*, vol. 159, pp. 601-621, 1982.

Kimler et al., "Ovulatory delay alters postnatal growth, behavior, and brain structure in rats", Developmental Brain Research, vol. 107, pp. 49-55, 1998.

Klementiev, et al., "A neural cell adhesion molecule-derived peptide reduces neuropathological signs and cognitive impairment induced by Abeta(25-35)", *Neuroscience*, vol. 145, pp. 209-224, 2007.

Kogan et al., "Long-Term Memory Underlying Hippocampus-Dependent Social Recognition in Mice", *Hippocampus*, vol. 10, pp. 47-56, 2000.

Kolkova, et al., "Neural Cell Adhesion Molecule-Stimulated Neurite Outgrowth Depends on Activation of Protein Kinase C and the Ras-Mitogen-Activated Protein Kinase Pathway", *Journal of Neuroscience*, vol. 20(6), pp. 2238-2246, Mar. 15, 2000.

Kruman et al., "Evidence that 4-Hydroxynonenal Mediates Oxidative Stress-Induced Neuronal Apoptosis", *J. of Neurosci.*, vol. 17, No. 13, pp. 5089-5100, Jul. 1, 1997.

Laake et al., "A simple in vitro model of ischemia based on hippocampal slice cultures and propidium iodide fluorescence", *Brain Research Protocols*, vol. 4, pp. 173-184, 1999.

Loyter et al., "Mechanisms of DNA uptake by mammalian cells: Fate of exogenously added DNA monitored by the use of fluorescent dyes", *Proc. Natl. Acad. Sci. USA*, vol. 79, pp. 422-426, Jan. 1982.

Lu et al., "Chemically unambiguous peptide immunogen: preparation, oriented and antigenicity of purified peptide conjugated to the multiple antigen peptide system", *Mol. Immunol.*, vol. 28, No. 6, pp. 623-630, 1991.

Maar et al., "Characterization of Microwell Cultures of Dissociated Brain Tissue for Studies of Cell-Cell Interactions", *J. of Neurosci. Res.*, vol. 47, pp. 163-172, 1997.

Malich et al., "The sensitivity and specificity of the MTS tetrazolium assay for detecting the in vitro cytotoxicity of the 20 chemicals using human cell lines", *Toxicology*, vol. 124, pp. 179-192, 1997.

Matthes et al., "Simultaneous rapid chemical synthesis of over one hundred oligonucleotides on a microscale", *EMBO J.*, vol. 3, No. 4, pp. 801-805, 1984.

Maurice et al., "Amnesia induced in mice by centrally administered β-amyloid peptides involves cholinergic dysfunction", *Brain Research*, vol. 706, pp. 181-193, 1996.

McKnight et al., "Identification and molecular analysis of a third *Aspergillus nidulans* alcohol dehydrogenase gene", *EMBO J.*, vol. 4, No. 8, pp. 2093-2099, 1985.

Merle et al., "Basic Fibroblast Growth Factor Activates Calcium Channels in Neonatal Rat Cardiomyocytes", *J. of Biol. Chem.*, vol. 270, pp. 17361-17367, Jul. 21, 1995.

Miyamoto et al., "Autocrine FGF Signaling is Required for Vascular Smooth Muscle Cell Survival in Vitro", *J. of Cell. Physiology*, vol. 177, pp. 58-67, 1998.

Morris, "Developments of a water-maze procedure for studying spatial learning in a rat", *J. of Neurosci. Methods*, vol. 11, pp. 47-60, 1984.

Neumann et al., "Gene transfer into mouse lyoma cells by electroporation in high electric fields", *EMBO J.*, vol. 1, No. 7, pp. 841-845, 1982.

Ozen et al., "Role of Fibroblast Growth Factor Receptor Signaling in Prostate Cancer Cell Survival", *J. of Natl. Cancer Inst.*, vol. 93, No. 23, pp. 1783-1790, Dec. 5, 2001.

Palmiter et al., "Metallothionein-Human GH Fusion Genes Stimulate Growth of Mice", *Science*, No. 222, pp. 809-814, 1983.

Pigino et al., "Presenilin-1 Mutations Reduce Cytoskeletal Association, Deregulate Neurite Growth, and Potentiate Neuronal Dystrophy and Tau Phosphorylation", *J. of Neurosci.*, vol. 21, No. 3, pp. 834-842, Feb. 1, 2001.

Panicker, et al. "Recent Advances in Peptide-Based Microarray Technologies", *Combinatorial Chemistry & High Throughput Screening*, vol. 7, pp. 547-556, 2004.

Pavia, Michael, "The Chemical Generation of Molecular Diversity", http://www.netsci.org/Science/Combichem/feature01.html, pp. 1-11, May 14, 2010.

Pellois, et al., "Individually addressable parallel peptide synthesis on microchips", *Nature Biotechnology*, vol. 20, pp. 922-926, Sep. 2002.

Povlsen et al., "Intracellular Signaling by the Neural Cell Adhesion Molecule", *Neurochemical Research*, vol. 28, No. 1, pp. 127-141, Jan. 2003.

Powers et al., "Fibroblast growth factors, their receptors and signaling", *Endocrine-Related Cancer*, vol. 7, pp. 165-197, 2000.

Rajagopalan et al., "Use of the 3-nitro-2-pyridine sulfenyl protecting group to introduce $N^8$-branching at lysine during solid-phase peptide synthesis", *Int. J. Peptide Protein Res.*, vol. 45, pp. 173-179, 1995.

Reuss et al., "Fibroblast growth factors and their receptors in the central nervous systems", *Cell Tissue Res.*, vol. 313, pp. 139-157, 2003.

Rønn et al., "The neural cell adhesion molecule in synaptic plasticity and ageing", *Int. J. Devl. Neuroscience*, vol. 18, pp. 193-199, 2000.

Rønn et al., "Neurite Outgrowth Induced by a Synthetic Peptide Ligand of Neural Cell Adhesion Molecule Requires Fibroblast Growth Factor Receptor Activation", *Journal of Neurochemistry*, vol. 75, pp. 665-671, 2000.

Rougon, et al., "New insights into the diversity and function of neuronal immunoglobulin superfamily molecules", *Annu Rev Neurosci.*, vol. 26, pp. 207-238, 2003.

Russell et al., "DNA sequences of two yeast promoter-up mutants", *Nature*, vol. 304, No. 18, pp. 652-654, Aug. 1983.

Saiki et al., "Primer-Directed Enzymatic Amplification of DNA with a Thermostable DNA Polymerase", *Science*, vol. 239, pp. 487-491, 1988.

Sarin et al., "Quantitative Monitoring of Solid-Phase Peptide Synthesis by the Ninhydrin Reaction", *Analytical Biochemistry*, vol. 117, pp. 147-157, 1981.

Scott, et al., "Searching for Peptide Ligands with an Epitope Library", *Science*, vol. 249, pp. 386-390, Jul. 27, 1990.

Secher, et al., "A neural cell adhesion molecule-derived fibroblast growth factor receptor agonist, the FGL-peptide, promotes early postnatal sensorimotor development and enhances social memory retention", *Neuroscience*, vol. 141, pp. 1289-1299, 2006.

Slavin, "Fibroblast Growth Factors: At the Heart of Angiogenesis", *Cell Biology International*, vol. 19, No. 5, pp. 431-444, 1995.

Southern et al., "Transformation of Mammalian Cells to Antibiotic Resistance with a Bacterial Gene Under Control of the SV40 Early Region Promoter", *J. of Molecular and Applied Genetics*, vol. 1, pp. 327-341, 1982.

Stoppini et al., "A simple method for organotypic cultures of nervous tissue", *J. of Neuroscience Methods*, vol. 37, pp. 173-182, 1991.

Subramani et al., Expression of the Mouse Dihydrofolate Reductase Complementary Deoxyribonucleic Acid in Simian Virus 40 Vectors, *Molecular and Cellular Biology*, pp. 854-864, Sep. 1981.

Uttamchandani, et al., "Combinatorial Peptide Microarrays for the Rapid Determination of Kinase Specificity", *Bioorganic & Medicinal Chemistry Letters*, vol. 13, pp. 2997-3000, 2003.

Van Kampen, et al., "AR-R 17779 improves social recognition in rats by activation of nicotinic alpha7 receptors", *Psychopharmacology*, vol. 172, pp. 375-383, 2004.

Vasudevan et al., "Muscarinic acetylcholine receptor produced in recombinant baculovirus infected Sf9 insect cells couples with endogenous G-proteins to activate ion channels", *FEBS Letters*, vol. 311, No. 1, pp. 7-11, Oct. 1992.

Vianna et al., "Learning & Memory. Role of Hippocampal Signaling Pathways in Long-Term Memory Formation of a Nonassociative Learning Task in the Rat", *Learn Mem.*, vol. 7, pp. 333-340, 2000.

Walmod et al., "Automated in Vitro Screening of Teratogens", *Toxicology and Applied Pharmacology*, vol. 181, pp. 1-15, 2002.

Walmod, et al., "Zippers make signals: NCAM-mediated molecular interactions and signal transduction", *Neurochem Res.*, vol. 29, pp. 2015-2035, 2004.

Welzl et al., "Cell Adhesion Molecules: Key Players in Memory Consolidation?", *News Physiol. Sci.*, vol. 18, pp. 147-150, 2003.

Wigler et al., "Biochemical Transfer of Single-Copy Eucaryotic Genes Using Total Cellular DNA as Donor", *Cell*, vol. 14, pp. 725-731, Jul. 1978.

Ye et al., "Increase of Acidic Fibroblast Growth Factor in the Brains of Hamsters Infected with Either 263K or 139H Strains of Scrapie", *J. of Molecular Neuroscience*, vol. 18, pp. 179-188, 2002.

Zhu et al., "Evidendce that FGF receptor signaling is necessary for endoderm-regulated development of precardiac mesoderm", *Mechanisms of Ageing and Development*, vol. 108, pp. 77-85, 1999.

Albrechtsen, Amendment, mailed Nov. 8, 2010 on Application of Albrechtsen, U.S. Appl. No. 10/567,365.

USPTO, Rejection, mailed Aug. 31, 2010 on Application of Albrechtsen, U.S. Appl. No. 10/567,365.

Berezin, Preliminary Amendment, mailed Nov. 16, 2010 on Application of Berezin, U.S. Appl. No. 12/745,129.

Stahlhut et al., Journal of Neuroscience Research, 1997, vol. 48, Issue 2, pp. 112-121.

Banga, A.K. (Editor). Therapeutic peptides and protein formulation. Processing and delivery systems. Technomic Publishing AG, Basel, pp. 81-163 1995.

Berezin, V., Bock, E. and Poulsen, F.M.:The neural cell adhesion molecule. Curr Opin Drug Disc Dev, 2000, 3:605-609.

DeMello S.R., Borodezt K. and Soltoff S.P. (Mar. 1997) Insulin-like growth factor and potassium depolarization maintain neuronal survival by distinct pathways: possible involvement of PI 3-kinase in IGF-1 signaling. J. Neurosci. 17:1548-1560.

Doherty P, Walsh FS. CAM-FGF Receptor Interactions: A Model for Axonal Growth Mol Cell Neurosci. 1996 8:99-111.

Dzhandzhugazyan K, Bock E.Demonstration of (Ca(2+)-Mg2+)-ATPase activity of the neural cell adhesion molecule.FEBS Lett Dec. 27, 1993;336(2) :279-83.

Dzhandzhugazyan K, Bock E.Demonstration of an extracellular ATP-binding site in NCAM: functional implications of nucleotide binding.Biochemistry Dec. 9, 1997;36(49):15381-95.

Eilers A, Whitfield J, Babij C, Rubin LL, Ham J. Role of the Jun kinase pathway in the regulation of c-Jun expression and apoptosis in sympathetic neurons. J Neurosci. Mar. 1, 1998;18(5):1713-24.

Eriksson AE, Cousens LS, Matthews BW.Refinement of the structure of human basic fibroblast growth factor at 1.6 A resolution and analysis of presumed heparin binding sites by selenate substitution. Protein Sci Aug. 1993;2(8):1274-84.

Furka A, Sebestyen F, Asgedom M, Dibo G. General method for rapid synthesis of multicomponent peptide mixtures. Int J Pept Protein Res. Jun. 1991;37(6):487-93.

Hatten ME, Lynch M, Rydel RE, Sanchez J, Joseph-Silverstein J, Moscatelli D, Rifkin DB. In vitro neurite extension by granule neurons is dependent upon astroglial-derived fibroblast growth factor. Dev Biol Feb. 1988;125(2):280-9.

Horstkorte R, Schachner M, Magyar JP, Vorherr T, Schmitz B. The fourth mmunoglobulin-like domain of NCAM contains a carbohydrate recognition domain for oligomannosidic glycans implicated in association with L1 and neurite outgrowth. J Cell Biol. Jun. 1993;121(6):1409-21.

Hulley P, Schachner M, Lubbert H. L1 neural cell adhesion molecule is a survival factor for fetal dopaminergic neurons. J Neurosci Res. Jul. 15, 1998;53(2):129-34.

Jensen PH, Soroka V, Thomsen NK, Ralets I, Berezin V, Bock E, Poulsen FM.Structure and interactions of NCAM modules 1 and 2, basic elements in neural cell adhesion.Nat Struct Biol May 5, 1999 6:486-93.

Kasper C, Rasmussen H, Kastrup JS, Ikemizu S, Jones EY, Berezin V, Bock E, Larsen IK.Structural basis of cell-cell adhesion by NCAM. Nat Struct Biol May 2000;7(5):389-93.

Kiselyov VV, Berezin V, Maar TE, Soroka V, Edvardsen K, Schousboe A, Bock E.The first immunoglobulin-like neural cell adhesion molecule (NCAM) domain is involved in double-reciprocal interaction with the second immunoglobulin-like NCAM domain and in heparin binding.J Biol Chem Apr. 11, 1997;272(15):10125-34.

Lam KS, Salmon SE, Hersh EM, Hruby VJ, Kazmierski WM, Knapp RJ. A new type of synthetic peptide library for identifying ligand-binding activity. Nature. Nov. 7, 1991 354:82-84.

Ranheim TS, Edelman GM, Cunningham BA. Homophilic adhesion mediated by the neural cell adhesion molecule involves multiple immunoglobulin domains. Proc Natl Acad Sci U S A Apr. 30, 1996;93(9):4071-5.

Rao Y, Wu XF, Gariepy J, Rutishauser U, Siu CH. Identification of a peptide sequence involved in homophilic binding in the neural cell adhesion molecule NCAM. J Cell Biol Aug. 1992;118(4):937-49.

Rao Y, Zhao X, Siu CH. Mechanism of homophilic binding mediated by the neural cell adhesion molecule NCAM. Evidence for isologous interaction. J Biol Chem. Nov. 4, 1994;269(44):27540-8.

Retzler C, Gohring W, Rauch U. Analysis of neurocan structures interacting with the neural cell adhesion molecule N-CAM. J Biol Chem. Nov. 1, 1996;271(44):27304-10.

Ronn LC, Bock E, Linnemann D, Jahnsen H. NCAM-antibodies modulate induction of long-term potentiation in rat hippocampal CA1. Brain Res. Apr. 17, 1995;677(1):145-51.

Ronn LC, Olsen M, Ostergaard S, Kiselyov V, Berezin V, Mortensen MT, Lerche MH, Jensen PH, Soroka V, Safell JL, Doherty P, Poulsen FM, Bock E, Holm A, Saffells JL. Identification of a neuritogenic ligand of the neural cell adhesion molecule using a combinatorial library of synthetic peptides. Nat Biotechnol. Oct. 1999;17(10):1000-5.

Ronn LC, Ralets I, Hartz BP, Bech M, Berezin A, Berezin V, Moller A, Bock E. A simple procedure for quantification of neurite outgrowth based on stereological principles. J Neurosci Methods. Jul. 31, 2000;100(1-2):25-32.

Sibanda BL, Blundell TL, Thornton JM. Conformation of beta-hairpins in protein structures. A systematic classification with applications to modelling by homology, electron density fitting and protein engineering. J Mol Biol Apr. 20, 1989;206(4):759-77.

Skaper SD, Floreani M, Negro A, Facci L, Giusti P. Neurtotrophins rescue cerebellar granule neurons from oxidative stress-mediated apoptotic death: selective involvement of phosphatidylinositol 3-kinase and the mitogen-activated protein kinase pathway. J Neurochem. May 1998;70(5):1859-68.

Skladchikova G, Ronn LC, Berezin V, Bock E. Extracellular adenosine triphosphate affects neural cell adhesion molecule (NCAM)-mediated cell adhesion and neurite outgrowth. J Neurosci Res Jul. 15, 1999;57(2):207-18.

Villalba M, Bockaert J, Journot L. Pituitary adenylate cyclase-activating polypeptide (PACAP-38) protects cerebellar granule neurons from apoptosis by activating the mitogen-activated protein kinase (MAP kinase) pathway. J Neurosci. Jan. 1, 1997;17(1):83-90.

Wilmot CM, Thornton JM. Beta-turns and their distortions: a proposed new nomenclature. Protein Eng. May 1990;3(6):479-93.

Yao R, Cooper GM. Requirement for phosphatidylinositol-3 kinase in the prevention of apoptosis by nerve growth factor. Science. Mar. 31, 1995;267(5206):2003-6.

Cambon, K., et al. Post-training administration of a synthetic peptide ligand of the neural cell adhesion molecule, C3d, attenuates long-term expression of contextual fear conditioning. Neuroscience 122 (2003) 183-191.

Soroka, V., et al. Structure and Interactions of NCAM Ig1-2-3 Suggest a Novel Zipper Mechanism for Homophilic Adhesion. Structure, vol. 10, 1291-1301, Oct. 2003.

Pedersen, M.V., et al. Neuritogenic and Survival-Promoting Effects of the P2 Peptide Derived From a Homphilic Binding Sidte in the Neural Cell Adhesion Molecule. Journal of Neuroscience Research 75: 55-65 (2004).

Ditlevsen, D.K., et al. The role of phosphatidylinositol 3-kinase in neural cell adhesion molecule-mediated neuronal differentiation and survival. Journal of Neurochemistry, 2003, 84, 546-556.

Hartz, B.P., et al. A synthetic peptide ligand of NCAM affects exploratory behaviour and memory in rodents. Pharmacology, Biochemistry and Behavior 75 (2003) 861-867.

Jessen, U., et al. Neural Cell Adhesion Molecule-Mediated Neurite Outgrowth Is Repressed by Overexpression of HES-1. Journal of Neuroscience Research 71:1-6 (2003).

Kiselyov, V., et al. Structural Basis for a Direct Interaction between FGFR1 and NCAM and Evidence for a Regulatory Role of ATP. Structure, vol. 11, 691-701, Jun. 2003.

Kiryushko, D., et al. A Synthetic Peptide Ligand of Neural Adhesion Molecule (NCAM), C3d, Promotes Neuritogenesis and Synaptogenesis and Modulates Presynaptic Function in Primary Cultures of Rat Hippocampal Neurons. The Journal of Biological Chemistry, vol. 278, No. 14, Issue of Apr. 4, pp. 12325-12334, 2003.

Rønn, L.C.B., et al. Characterization of a novel NCAM ligand with a stimulatory effect on neurite outgrowth identified by screening a combinatorial peptide library. European Journal of euroscience, vol. 16, pp. 1720-1730, 2002.

Klementiev, B., et al. A peptide agonist of the neural cell adhesion molecule (NCAM), C3, protects against developmental defects induced by a teratogen pyrimethamine. Int. J. Devl Neuroscience 20 (2002) 527-536.

Soroka, V., et al. Induction of Neuronal Differentiation by a Peptide Corresponding to the Homophilic Binding Site of the second Ig Module of the Neural Cell Adhesion Molecule. The Journal of Biological Chemistry, vol. 277, No. 27, Issue of Jul. 5, pp. 24676-24683, 2002.

Rønn, L.C.B., et al. Increased intracellular calcium is required for neurite outgrowth induced by a synthetic peptide ligand of NCAM. FEBS Letters 518 (2002) 60-66.

Jessen, U., et al. The transcription factors CREB and c-Fos Play key roles in NCAM-mediated neuritogenesis in PC12-E2 cells. Journal of Neurochemistry, 2001, 79, 1149-1160.

Berezin, V., Bock, E. NCAM mimetic peptides: Pharmacological and therapeutic potential.

Ming, Yi., et al. "A fibronectin fragment inhibits tumor growth, angiogenesis, and metasis" PNAS, vol. 98, No. 2, Jan. 16, 2001, 620-624.

Frei, T., et al. "Different Extracellular Domains of the Neural Cell Adhesion Molecule (N-CAM) Are Involved in Different Functions" Journal of Cell Biology, Rockefeller University Press. vol. 118, No. 1, Jul. 1992. 177-194.

Kasper, C., et al. "Functional Characterization of NCAM Fibronection Type III Domains: Demonstration of Modulatory Effects of the Proline-Rich Sequence Encoded by Alternatively Spliced Exons a and AAG" Journal of Neuroscience Research, 46:173-186, 1996.

Chan, et al. "Identification, classification, and analysis of beta-bulges in proteins", *Protein Science*, vol. 2, pp. 1574-1589, 1993.

Kiselyov, V.V., et al. "Structure of the second fibronectin type III module of NCAM. Iden tification of a neuritogenic site" European Journal of Neuroscience. vol. 12, No. 11, 2000.

* cited by examiner

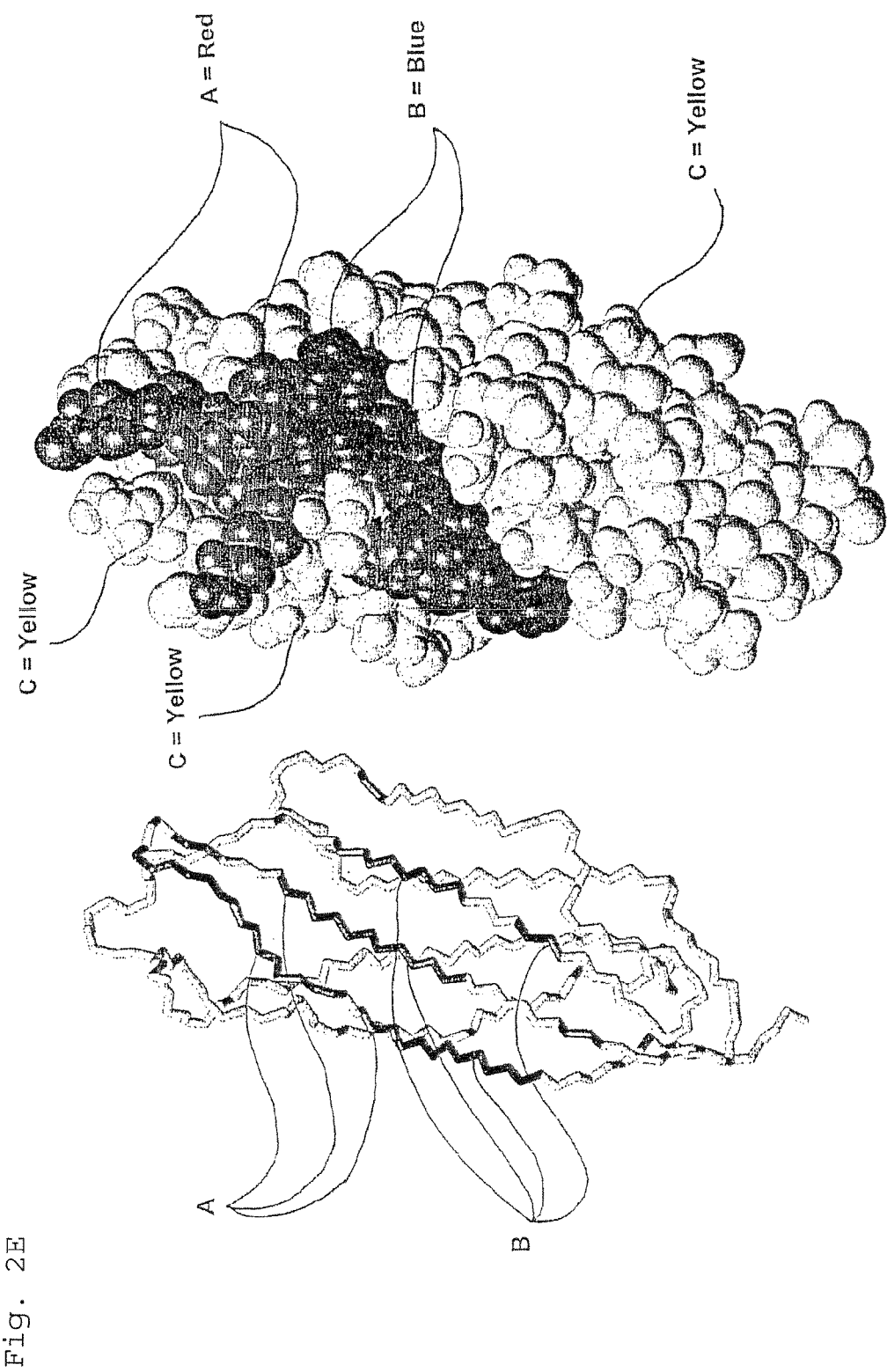

a b c d a b

AENQQGK – NCAM heptamer (blue – A)
|...::||
AMKEDGR – basic FGF heptamer (red – B)

Fig. 9A

Peptides derived from the FG-loop of the third fibronectin type III-module of the neural cell adhesion molecule L1:

- AFNGRGLG
- QAFNGRGLGP
- EVQAFNGRGLGPPAS

Peptides derived form the FG-loop of the first fibronectin type III-module of NCAM:

- ALNGKGLG
- AALNGKGLGE
- RLAALNGKGLGEIS

COMPOUNDS CAPABLE OF AFFECTING DIFFERENTIATION, PROLIFERATION, REGENERATION, PLASTICITY AND SURVIVAL CELLS

The present invention relates to a compound comprising the third Immunoglobulin (Ig3) module, and/or the fourth Immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, capable of interacting with an Fibroblast Growth Factor (FGF) receptor and/or Adenosine-Tri-Phosphate (ATP) and/or L1, and thereby the compounds are capable of inducing differentiation, modulating proliferation, stimulate regeneration, neuronal plasticity and/or survival of cells. Further, the present invention relates to a pharmaceutical composition comprising said compound, a process of producing a pharmaceutical composition and the use of said compound.

BACKGROUND OF THE INVENTION

Cell adhesion molecules (CAMs) constitute a group of proteins mediating adhesion between cells. A major group of CAMs belongs to the immunoglobulin (Ig) superfamily characterised by the presence of immunoglobulin domains. The neural cell adhesion molecule (NCAM) is such a cell adhesion molecule of the Ig superfamily that is particularly abundant in the nervous system. NCAM is expressed on the external membrane of nerve cells. When an NCAM molecule on one cell binds to another NCAM molecule on another cell (homophilic binding), the binding between the two cells is strengthened. NCAM not only binds to NCAM but also to other proteins and/or glycoconjugates found on nerve cells or in the extracellular matrix (heterophilic binding). NCAM also binds ATP. NCAM interactions influence migration of cells, extension of neurites, fasciculation of neurites, cell proliferation, cell survival, and formation of synapses.

NCAM is encoded by a single gene, containing at least 25 exons. Due to alternative splicing of precursor mRNA, a variety of mature mRNA species and thereby protein isoforms of NCAM can be produced. Three major NCAM isoforms are generated by alternative splicing of exons 15 and 18 determining the mode of attachment of NCAM to the plasma membrane and the size of the intracellular NCAM domains, respectively. In the nervous system a glycosylphosphatidyl inositol (GPI) anchored 120 kDa isoform is expressed on the surface of glial cells, a transmembrane 140 kDa isoform is expressed on both neurons and glial cells, whereas a transmembrane 180 kDa isoform is found predominantly on the surface of neurons. The extracellular part of NCAM comprises five Ig-like homology modules (Ig1, Ig2, Ig3, Ig4 and Ig5) and two fibronectin type III modules (F3,1 and F3,2) (Berezin et al., 2000).

Heterophilic ligands of NCAM comprise a variety of heparan sulfate proteoglycans (e.g. agrin) and chondroitin sulfate proteoglycans (e.g. neurocan). NCAM Ig1 and Ig2 are probably the structural determinants of the interaction of NCAM with heparan sulfate proteoglycans since these two modules have been shown to bind heparin (Kiselyov et al. 1997). Reports on whether the core protein or the carbohydrate moieties are responsible for the binding of proteoglycans to NCAM are contradictory, and the contribution of this interaction to NCAM-mediated cellular functions is currently not understood (Retzler et al. 1996). The neural cell adhesion molecule L1 and the fibroblast growth factor (FGF) receptor are other heterophilic ligands of NCAM. The interaction between NCAM and L1 has been shown to be mediated by N-linked oligo-mannosidic glycans carried by L1 and a lectin-like binding site localised in the fourth Ig module of NCAM. Through this binding NCAM has been suggested to participate in a so-called assisted L1-L1 homophilic interaction (Horstkorte et al., 1993) presenting an interesting example of co-operation between two neural CAMs.

Three different models of homophilic binding have been suggested: 1) a binding between the third Ig-like modules (Rao et al., 1992) of two opposing molecules; 2) involvement of all five Ig-like modules in an antiparallel interaction (Ranheim et al., 1996); and 3) a reciprocal binding of the first and second Ig-like modules (Kiselyov et al., 1997). The latter model has recently been confirmed by nuclear magnetic resonance (NMR) analysis (Jensen et al., 1999) and X-ray crystallography (Kasper et al., 2000).

NCAM plays a crucial role during the development of the nervous system and of organs, such as kidney, bowel, heart, gonads, pancreas, and muscles. In the mature nervous system NCAM is important for the plasticity of neuronal connections associated with regeneration, learning and memory. In the peripheral nervous system NCAM is involved in the initiation of outgrowth of nerve fibres and formation of nerve-muscle connections in regeneration after damage including lesions.

In signal transduction NCAM transduces extracellular signals leading to tyrosine phosphorylation, such as for example of the FGF-receptor, and an increase in intracellular calcium concentration.

Doherty and Walsh (1999) describe that NCAM, N-cadherin and L1 stimulate axonal growth by activating the fibroblast growth factor receptor (FGFR) in neurons.

NCAM binding compounds capable of stimulating differentiation and/or neurite outgrowth from cells presenting NCAM are disclosed in WO 00/18801, in which the compounds are used in the treatment for regeneration of NCAM presenting cells.

The identification of one such compound, C3, is described by Rønn et al. (1999). C3 stimulates outgrowth by activating a signalling pathway identical to that activated by homophilic NCAM binding, but it does not bind directly to FGF receptors.

Various factors may cause neuronal cell death. Preventing neuronal cell death in individuals being exposed to risk factors causing cell death may be called maintaining/stimulating or promoting survival of the cells, or it may be called neuroprotection.

When neuronal cells are damaged, e.g. by reduced oxygen supply, the processes of cell death start and lead to cellular dysfunction, "collapse" of the intercellular communication between cells (network), retraction of cell processes and eventually cell death. Preventing neuronal cell death, i.e. stimulating/promoting survival means that the cells are protected from initiation of the processes of cell death.

Survival of nerve cells has been discussed in some references, for example Hulley et al. (1998) disclose that the L1 neural cell adhesion molecule is capable of stimulating survival and differentiation in fetal mid-brain dopaminergic neurons cultured in the presence of the toxin MPP+.

U.S. Pat. No. 6,037,320 describes the identification of a neurotrophic factor, NT-4 and in U.S. Pat. No. 5,767,240 an activity-dependent neurotrophic factor capable of increasing the survival of spinal cord neuronal cells, cerebral cortical cells and hippocampal neurons is revealed.

Further, U.S. Pat. No. 5,567,682 concerns a method of treating the symptoms of Alzheimer's disease by intranasal administration of short chain peptides. The peptides promote neuronal survival by reducing or halting progressive neuronal degeneration.

NCAM has recently been demonstrated to have an ecto-adenosine triphosphatase (ATPase) activity (Dzhandzhugazyan and Bock, 1993 and 1997). The role of this activity in ATP is one of the most abundant neurotransmitters in the nervous system. In a recent study it has been demonstrated that ATP modulates NCAM induced neurite outgrowth, indicating that ATP may be a regulator of the putative NCAM-FGF-receptor signalling pathway (Skladchikova et al., 1999).

However, the inventors of the present invention have surprisingly found that a compound comprising the third Immunoglobulin (Ig3) module, and/or the fourth immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof is capable of inducing differentiation, modulating proliferation, stimulating regeneration, neuronal plasticity and survival of cells through an interaction with the Fibroblast Growth Factor (FGF) receptor and/or adenosine-tri-phosphate (ATP) and/or L1.

SUMMARY OF THE INVENTION

The present invention concerns a compound comprising the third Immunoglobulin (Ig3) module, and/or the fourth Immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, capable of interacting with Fibroblast Growth Factor (FGF) receptor and/or Adenosine-Tri-Phosphate (ATP) and/or L1. In the present context first Fibronectin III module and second Fibronectin III module are equal to the denomination "F3,1 and F3,2" or "FnIII,1 and FnIII,2" or "Fn3,1 and Fn3,2".

In a further aspect the invention concerns a compound comprising the fourth Immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant, capable of interacting with the FGF receptor and/or adenosine-tri-phosphate (ATP) and/or L1.

The compound of the invention is capable of inducing differentiation, modulating proliferation, stimulate regeneration, neuronal plasticity and survival of cells presenting the FGF receptor and/or NCAM ligand presenting cells.

Further, the invention describes a pharmaceutical composition comprising at least one compound of the invention, and a process of producing such a pharmaceutical composition. Also, the use of a compound of the invention is within the scope of the invention as well as a method for treating diseases and conditions with the compound.

FIGURES

FIG. 1. shows the structure of NCAM F3,2 determined by means of $^1$H, $^{15}$N NMR spectros copy. Structure of the second F3 module of NCAM, a) Stereo view of an overlay of the backbone atoms of 30 superimposed structures, b) Ribbon representation of the structure. The structure consists of 7 anti-parallel β-strands arranged in a sandwich of two β-sheets, one containing three strands (ABE) and the other four strands (CDFG).

Figure 2:
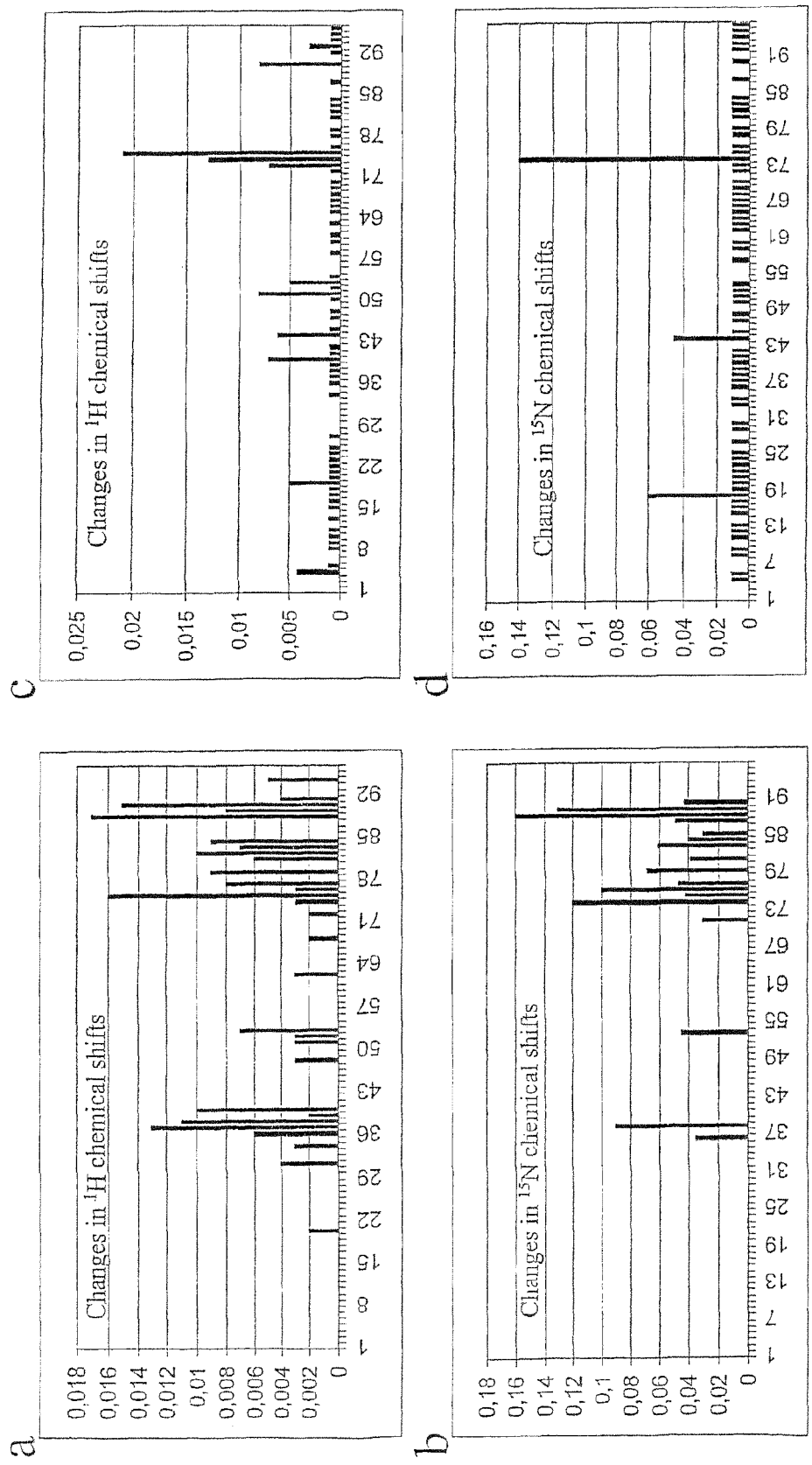

FIG. 2. Demonstration of interaction between the second F3 module of NCAM and the third Ig module of the FGF-receptor or ATP. a-d) Changes in the chemical shifts of $^1$H and $^{15}$N atoms of 0.05 mM $^{15}$N labeled sample of the second F3 module of NCAM after addition of 1 mM unlabeled sample of the third Ig module of the FGF-receptor (a, b) or 5 mM AMP-PCP (c, d). e) Mapping of the residues of the second F3 module of NCAM with changes in the chemical shifts (in the presence of the third Ig module of the FGF-receptor) greater than 0.006 ppm for $^1$H or 0.03 ppm for $^{15}$N atoms, onto the structure of the module. The residues with strong changes in the chemical shifts (greater than 0.01 ppm for $^1$H or 0.1 ppm for $^{15}$N atoms) are colored blue (shown by A) and with weak changes—red (shown by B); all other residues are colored yellow (shown by C). f) Mapping of the residues of the second F3 module perturbed by AMP-PCP (blue color—shown by C) and the residues of the ATP binding Walker motif A (red color—shown by A) and Lys 85 (green color—shown by B) to the structure of the module; all other residues are colored yellow (shown by D). g) A possible arrangement of the complex of the second F3 module of NCAM with ATP.

Figure 3:
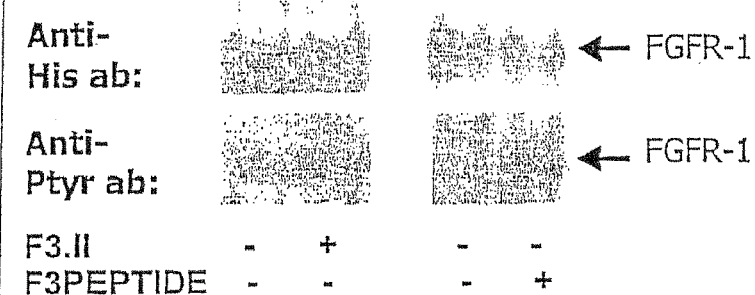
Figure 3:
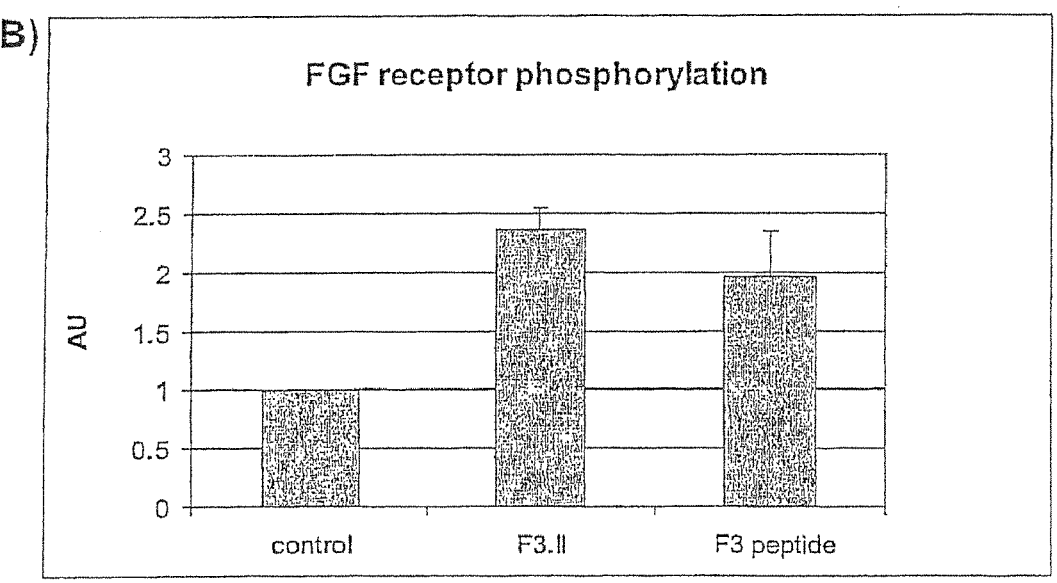

FIG. 3. Effect of the second F3 module, its FGF-receptor binding part (the FG loop peptide) on phosphorylation of the FGF-receptor 1. HEK293 cells, transiently transfected with a His-tagged version of the FGF-receptor 1, were stimulated for 20 min with either 5 µg/ml F3,2 module or 50 µg/ml FG loop peptide. a) The total amount of the FGF-receptor 1 and the amount of the FGF-receptor phosphorylation was estimated by immunoblotting using anti-pentahis (anti-His) and anti-phosphotyrosine (anti-P-tyr) antibodies, respectively. b) Quantification of the FGF-receptor phosphorylation by densitometric analysis of the band intensity. Phosphorylation was estimated relative to the control (untreated cells), which has been normalized to 1.0. Error bar represents one standard deviation (SD). $P<0.05$ by paired t test comparing treated cells with controls. The t test was performed on array of six independent sets of non-normalized data.

Figure 4:
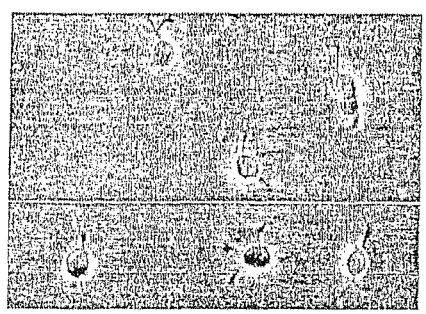
Figure 4:
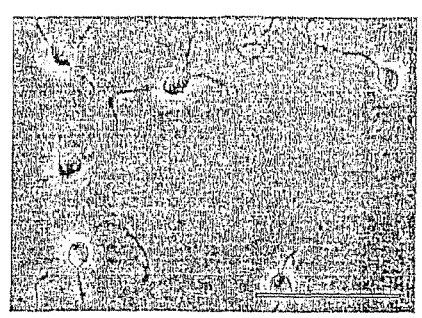
Figure 4:
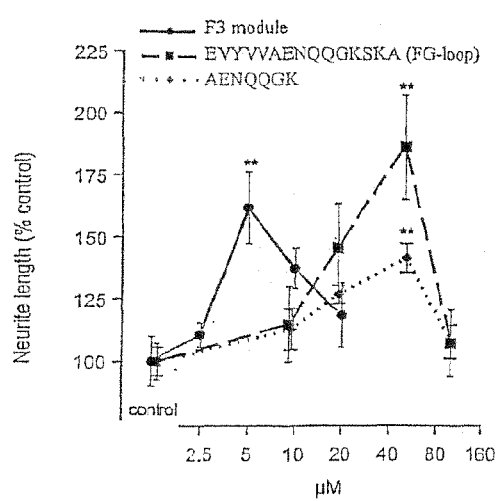
Figure 4:
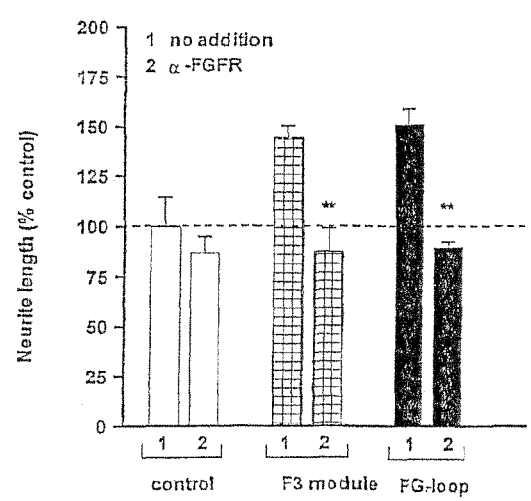

FIG. 4. Effect of the second F3 module and its FGF-receptor binding part (the FG loop peptide) on neurite outgrowth from hippocampal neurons. a) Micrographs of the control (untreated) neurons. b) Micrographs of neurons treated with 5 µM second F3 module. c) Plot of the neurite length versus the concentration of the second F3 module, the FG-loop peptide (SEQ ID NO:1) and a truncated version (SEQ ID NO:5) of the peptide. $p<0.01$ compared to the control (untreated cells) d) Effect of an anti-FGF-receptor antibody on neurite outgrowth induced by 5 µM second F3 module or 50 µM GF loop peptide. $p<0.01$ compared to the cultures treated only with the F3 module of FG-loop peptide (without a-FGFR).

Figure 5:
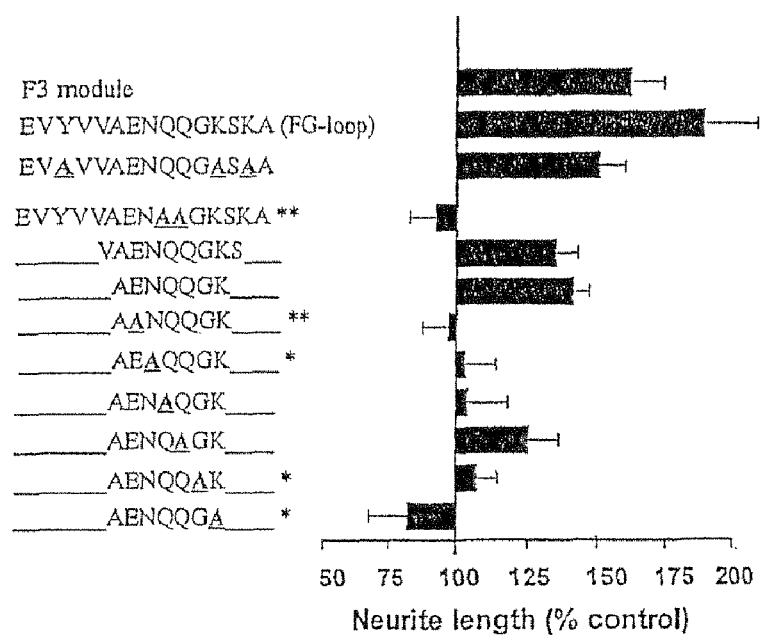
Figure 5:
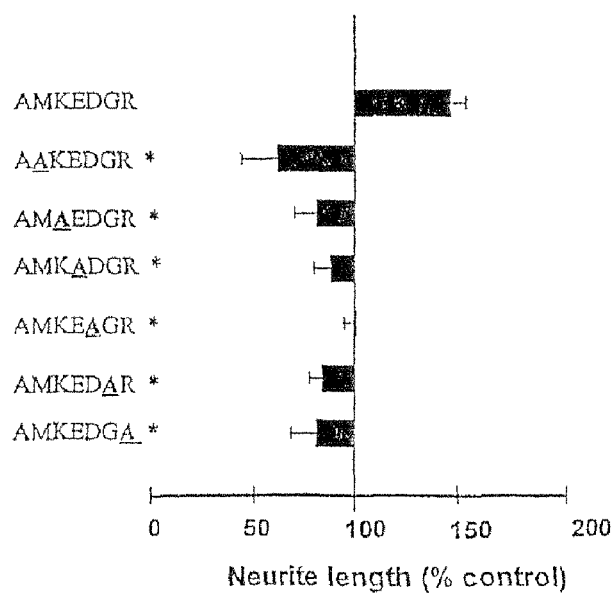

FIG. 5. Effect of various modifications of the FG loop peptide and a peptide derived from basic FGF on their peptides potency to stimulate neurite outgrowth from hippocampal neurons. Concentration of the various peptides was 50 µM. a) Effect of truncations and substitutions of the various amino acids with Ala in the FG loop peptide or truncated versions of the peptide. The peptides with specified sequence are in order from top-to-bottom, SEQ ID NOs: 1, 2, 207, 3, 5, 208, 209, 210, 6, 211 and 212. *$p<0.05$ compared to the cultures treated with the non-mutated peptide EVYVVAEN-QQGKSKA (SEQ ID NO:1), **$p<0.01$ compared to the cultures treated with the non-mutated peptide EVYVVAEN-QQGKSKA (SEQ ID NO:1). b) effect of substitution of the various amino acids with Ala in a peptide derived from basic FGF. The firs peptide is the non-mutated peptide AMKEDGR (SEQ ID NO:7), and the mutated peptides are in order from top-to-bottom, SEQ ID NOs:213, 214, 215, 216, 217 and 218. *p<0.05 compared to the cultures treated with the non-mutated peptide (AMKEDGR) (SEQ ID NO:7).

FIG. 6. Sequential and structural similarity between heptameric peptides derived from the FGF-receptor binding part of NCAM (AENQQGK, SEQ ID NO:5) and basic FGF (AMKEDGR SEQ ID NO:7). a) Sequential alignment of the heptamers, in which signs "?", " ", ":", and "?" indicate the level of similarity in a decreasing order from strong to low similarity. b) structural alignment of the backbone atoms of the heptamers from NCAM (blue color—shown by A) and basic FGF (red color—shown by B).

Figure 7:
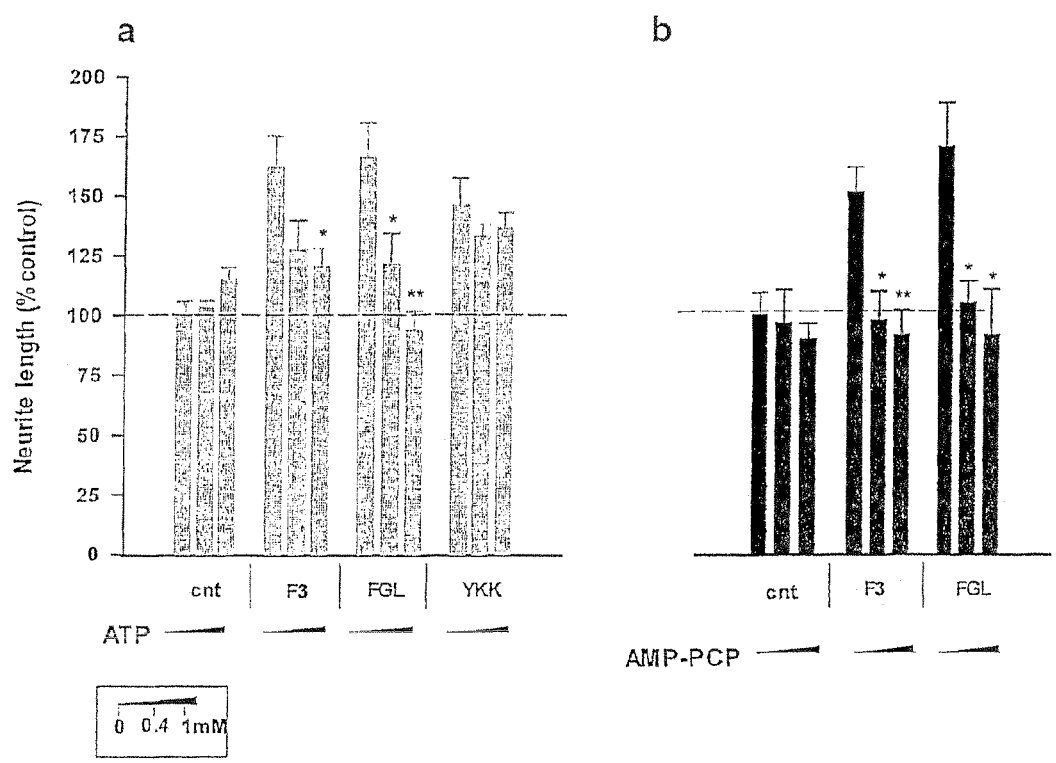

FIG. 7. Effect of ATP (a) and AMP-PCP (b) on the potency of the second F3 module, the FG loop peptide and a modified version of the peptide to stimulate neurite outgrowth from hippocampal neurons. Neurons were stimulated with either 5 μM second F3 module or 50 μm peptide in the presence of various concentrations of ATP or AMP-PCP (0, 0.4, 1.0 mM). "cnt" stands for control, "F3"—the second F3 module, "FGL"—the FG loop peptide, and "YKK"—the FGL peptide in which Tyr 74, Lys 83 and Lys 85 were substituted for Ala. a) *p<0.05 and **p<0.01 compared to the cultures treated with F3 or FGL in the absence of ATP. b) *p<0.05 and **p<0.01 compared to the cultures treated with F3 or FGL in the absence of AMP-PCP.

Figure 8:
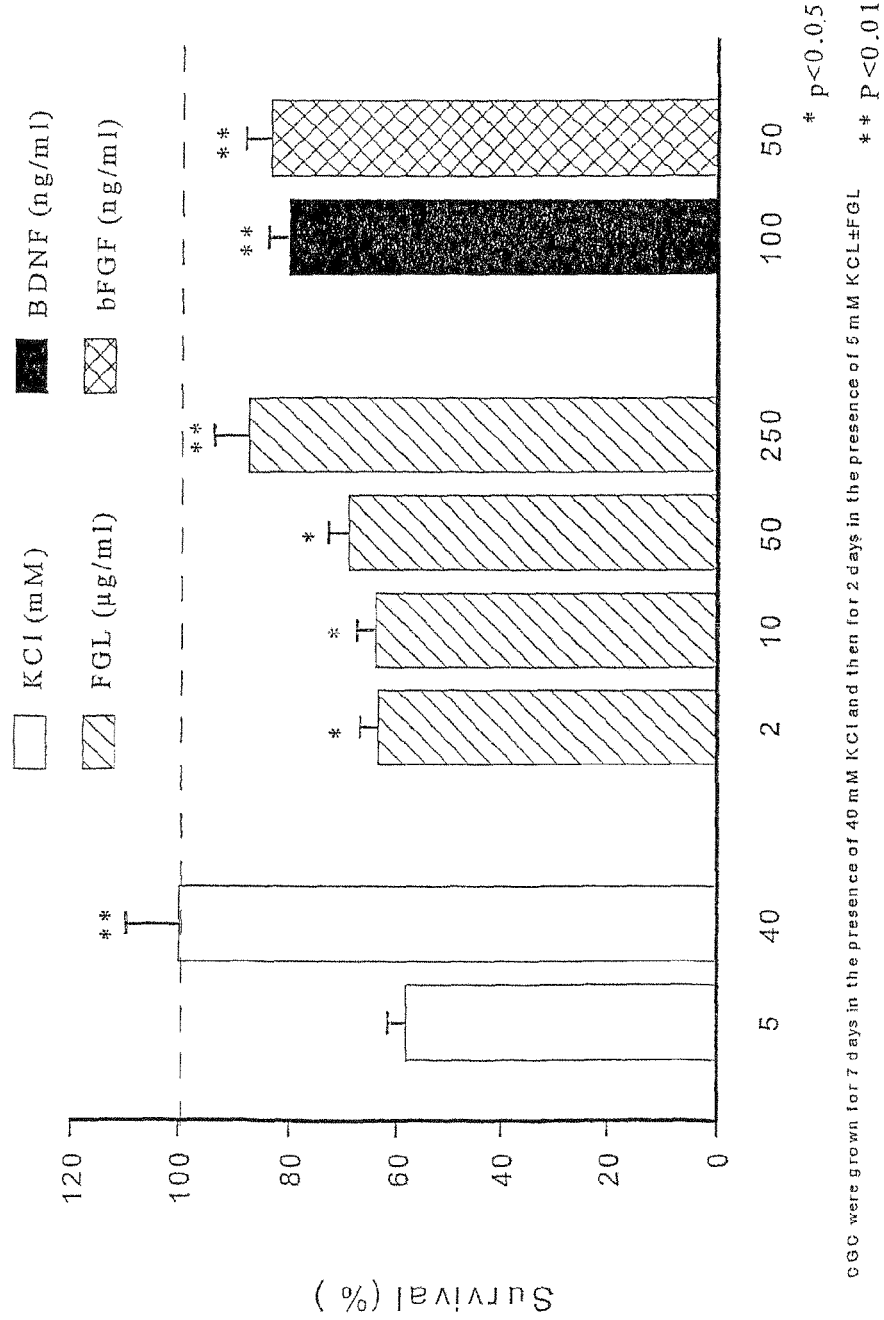

FIG. 8. Cerebellar granule neurons from seven days old rats were grown in the presence of 40 mM potassium. The cells were subsequently transferred to serum-free medium containing only five mM potassium and grown for two days in serum-free medium supplemented with various concentrations of he FGL-peptide (see FIG. 8). Subsequently, the number of cells were determined and the amount of cells surviving in the presence of high-concentration of potassium was set at 100%. As can be seen approx. Only 60% survived in the presence of brains-derived neurotrophic factor or basic fibroblast growth factor. When FGL was added in a sode-range of 2-250 microgram per ml statistically significant survival was observed up to 90% of the positive control at a dose of 250 microgram per ml of the monomeric form of the FGL peptide.

FIG. 9a. Peptides derived from the FG-loops of the neural cell adhesion molecules L1 and NCAM (third F3-module of L1 and the first F3 module of NCAM) were prepared in different lengths, see FIG. 9a, and their effect on neurite outgrowth from primary hippocampal neurons were tested adding the various peptides in a concentration of 25 microM.

Figure 9B:
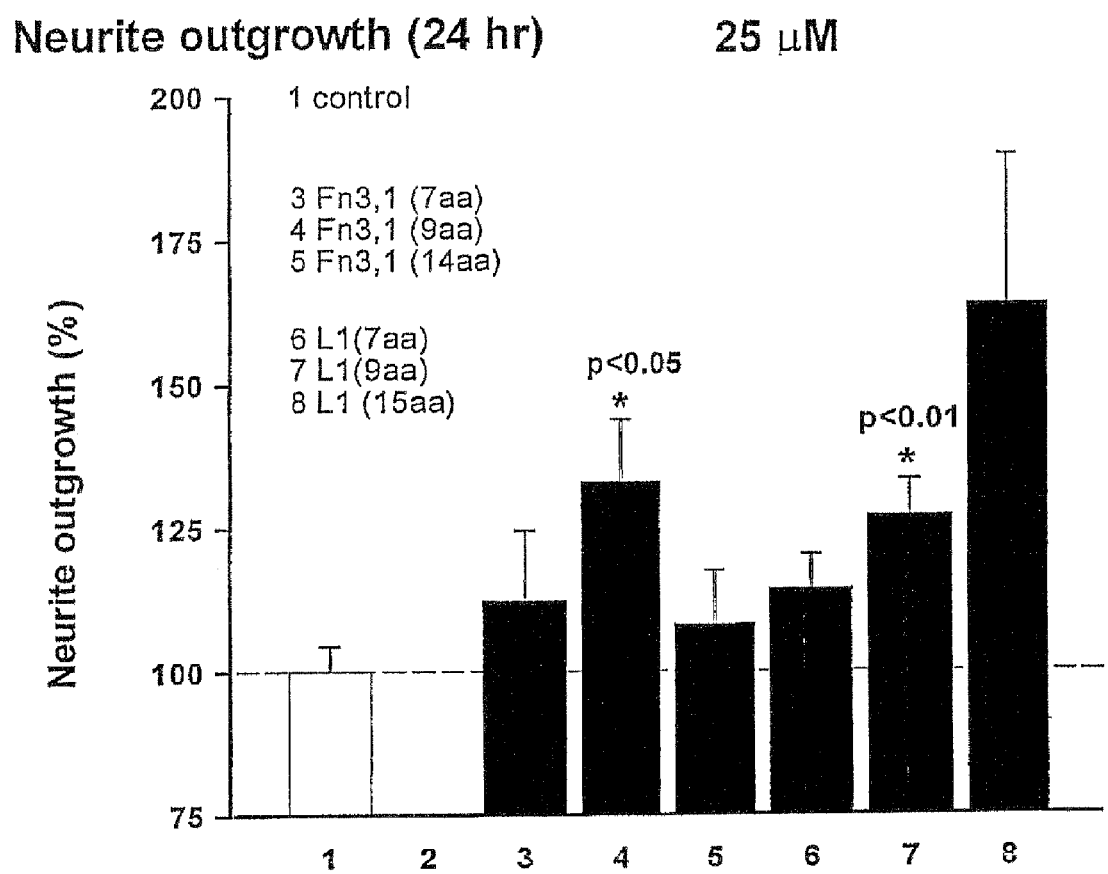

FIG. 9b. The NCAM peptides are referred to as FN3,1 and the L1 peptides are referred to as L1. The variants indicated in FIG. 9a are indicated by the number of amino acids in each peptide. As can be seen from the figure, the peptides had a stimulatory effect on neurite outgrowth reaching statistically significance for the nine amino acid variant of the Fgloop fo first fibronectin type III module of NCAM and the nine amino acid variant of the FG-loop of the third fibronectin type III-module of L1.

DETAILED DESCRIPTION OF THE INVENTION

The compound according to the invention relates to the induction of differentiation, modulation of proliferation, stimulation of regeneration, neuronal plasticity and survival of cells.

By the term FGL peptide is meant FG loop peptide of NCAM, which is an FGF receptor binding site of NCAM corresponding to SEQ ID NO: 1.

By the term "modulation" is meant a change, for example either an inhibition or a stimulation.

In the present context the term "interacting" refers to the direct or indirect contact between a compound of the invention and the FGF receptor, preferably a direct interaction. The term "direct interaction" means that the compound in question binds directly to the receptor.

By the term "cells presenting the FGF receptor" is meant cells expressing the FGF receptor on the external membrane of the cells, these cells are for example neurons, glial cells, all types of muscle cells, neuroendocrine cells, gonadal cells and kidney cells, endothelial cells and fibroblasts.

By the term "cells presenting an NCAM ligand" is meant cells expressing a receptor or ligand whereto NCAM and/or parts of NCAM may bind (i.e.: so-called counter-receptor). Examples of NCAM ligands are the FGF (fibroblast growth factor) receptor, L1 or glyco-conjugates or glucose-aminoglycans, such as heparin, heparan sulphateproteoglycans, and chondroitin sulphate proteoglycans and ATP.

In the present context the wording "stimulate/promote survival" is used synonymously with the wording "preventing cell death" or "neuroprotection". By stimulating/promoting survival it is possible to prevent diseases or prevent further degeneration of the nervous system in individuals suffering from a degenerative disorder.

"Survival" refers to the process, wherein a cell has been traumatised and would under normal circumstances, with a high probability die, if not the compound of the invention was used to prevent said cell from degenerating, and thus promoting or stimulating survival of said traumatised cell.

"Neuronal plasticity" refers to the capability of remodelling neuronal connections.

Peripheral nerve cells possess to a limited extent a potential to regenerate and re-establish functional connections with their targets after various injuries. However, functional recovery is rarely complete and peripheral nerve cell damage remains a considerable problem. In the central nervous system, the potential for regeneration is even more limited. Therefore, the identification of substances with the ability to prevent neuronal cell death in the peripheral and the central nervous system is significant and of great commercial value.

Accordingly, the present invention relates to the finding that a compound comprising the third Immunoglobulin (Ig3) module, and/or the fourth Immunoglobulin (Ig4) module, and/or the fifth Immunoglobulin (Ig5) module, and/or the first Fibronectin III (F3,1) module, and/or the second Fibronectin III (F3,2) module of neural cell adhesion molecule (NCAM), or a fragment, or a variant, is capable of interacting with the Fibroblast Growth Factor (FGF) receptor and or Adenosine-Tri-Phosphate (ATP) and/or L1.

In the present context the NCAM molecule referred to is NCAM having the sequence shown in database SWISSPROT, accession No: P13591

In this sequence the position of the domains mentioned herein are as follows:

| | |
|---|---|
| Ig3: | 203-308 |
| Ig4: | 309-404 |
| Ig5: | 405-500 |
| F3,1: | 501-601 |
| F3,2: | 602-695 |

Further the invention concerns the finding that a compound comprising the fourth Immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, is capable of interacting with the FGF receptor and/or Adenosine-Tri-Phosphate (ATP) and/or L1, such as a compound comprising the fourth Immunoglobulin (Ig4) module, and/or the first Fibronectin III (Fn3,1) module, and/or the second Fibronectin III (Fn3,2) module of neural cell adhesion molecule (NCAM), or a fragment, or a variant thereof, is capable of interacting with the FGF receptor and/or Adenosine-Tri-Phosphate (ATP) and/or L1, or such as a compound comprising the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, is capable of interacting with the FGF receptor and/or Adenosine-Tri-Phosphate (ATP) and/or L1, such as a compound comprising the first Fibronectin III (Fn3,1) module, and/or the second Fibronectin III (Fn3,2) module of neural cell adhesion molecule (NCAM), or a fragment, or a variant thereof, is capable of interacting with the FGF receptor and/or Adenosine-Tri-Phosphate (ATP) and/or L1.

In the present context the "fragment thereof" is to be understood as being any part of the NCAM molecule capable of interacting with an FGF-receptor and/or ATP and/or L1 and through said binding modulate proliferation, and/or induce differentiation, and/or stimulate regeneration, neuronal plasticity and/or survival of cells. The "variant thereof" is to be understood as being any peptide sequence capable of interacting with FGF-receptors and/or ATP and/or L1, and via said binding induce differentiation, modulate proliferation, stimulate regeneration, neuronal plasticity and survival of cells. Thus, fragment or variant may be defined as i) Fragments/variants comprising an amino acid sequence capable of being recognised by an antibody also capable of recognising the predetermined NCAM amino acid sequence, and/or ii) Fragments/variants comprising an amino acid sequence capable of binding to a receptor moiety also capable of binding the predetermined NCAM amino acid sequence, and/or iii) Fragments/variants having at least a substantially similar binding affinity to at least one FGF receptor and/or ATP and/or L1 as said predetermined NCAM amino acid sequence.

In the present context the term "functional equivalent" means a variant as defined above.

The binding affinity of the compound according to the invention preferably has a binding affinity (Kd value) to NCAM and/or the NCAM ligand in the range of $10^{-3}$ to $10^{-10}$ M, such as preferably in the range of $10^{-4}$ to $10^{-8}$ M. According to the present invention the binding affinity is determined by one of the following assays of surface plasmon resonance analysis or nuclear magnetic resonance spectroscopy.

In the present context, a variant of the NCAM domains mentioned above is to be understood as being any compound interacting with any cell presenting a FGF receptor or an NCAM ligand, and/or L1 and through said interaction modulates proliferation, and/or induce differentiation, and/or stimulate regeneration, neuronal plasticity and/or survival of FGF receptor presenting cells, i.e. functional variants. Variants may be peptides, peptide derivatives, antibodies and non-peptide compounds such as small organic compounds, sugars and fats, as well as peptido-mimetics. In a preferred embodiment the variant is a peptide as discussed above.

In one embodiment variants may be understood to exhibit amino acid sequences gradually differing from the preferred predetermined sequence, as the number and scope of insertions, deletions and substitutions including conservative substitutions increase. This difference is measured as a reduction in homology between the predetermined sequence and the variant.

The peptides may be modified, for example by substitution of one or more of the amino acid residues. Both L-amino acids and D-amino acids may be used. Other modification may comprise derivatives such as esters, sugars, etc. Examples are methyl and acetyl esters. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be protein moieties, such as bovine serum albumin (BSA), or lipophilic dendrimers, or micelle-like carriers formed by lipophilic derivatives, or starburst (star-like) carbon chain polymer conjugates.

Variants of the fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It is clear from the above outline that the same equivalent or fragment thereof may comprise more than one conservative amino acid substitution from more than one group of conservative amino acids as defined herein above.

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The addition or deletion of an amino acid may be an addition or deletion of from 2 to preferably 10 amino acids, such as from 2 to 8 amino acids, for example from 2 to 6 amino acids, such as from 2 to 4 amino acids. However, additions of more than 10 amino acids, such as additions from 2 to 10 amino acids, are also comprised within the present invention. In the multimeric forms additions/deletions may be made individually in each monomer of the multimer.

The invention also concerns non-peptide variants of the compounds disclosed herein. In particular, such variants should be understood to be compounds which bind to or in other ways interact with a Fibroblast Growth Factor (FGF) receptor and/or Adenosine-Tri-Phosphate (ATP) and/or L1 and thereby stimulating FGF receptor signalling and/or modulating proliferation and/or inducing differentiation and/or stimulating regeneration, neuronal plasticity and/or survival of cells presenting an FGF receptor.

It will thus be understood that the invention concerns a compound comprising at least one fragment capable of binding at least one receptor, or a variant thereof including any variants and functional equivalents of such at least one fragment.

A functional equivalent obtained by substitution may well exhibit some form or degree of native NCAM activity, and yet be less homologous, if residues containing functionally similar amino acid side chains are substituted. Functionally similar in the present respect refers to dominant characteristics of the side chains such as hydrophobic, basic, neutral or acidic, or the presence or absence of steric bulk. Accordingly, in one embodiment of the invention, the degree of identity between i) a given functional equivalent capable of effect and ii) a preferred predetermined fragment, is not a principal measure of the fragment as a variant or functional equivalent of a preferred predetermined peptide fragment according to the present invention.

Fragments sharing at least some homology with a preferred predetermined fragment of at least 3 amino acids, more preferably at least 5 amino acids, are to be considered as falling within the scope of the present invention when they are at least about 25 percent homologous with the preferred predetermined NCAM peptide, or fragment thereof, such as at least about 30 percent homologous, for example at least about 40 percent homologous, such as at least about 50 percent homologous, for example at least about 55 percent homologous, such as at least about 60 percent homologous, for example at least about 65 percent homologous, such as at least about 70 percent homologous, such as at least about 75 percent homologous, for example at least about 80 percent homologous, such as at least about 85 percent homologous.

Sequence identity can be measured using sequence analysis software (for example, the Sequence Analysis Software Package of the Genetics Computer Group, University of Wisconsin Biotechnology Centre, 1710 University Avenue, Madison, Wis. 53705), with the default parameters as specified therein.

Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a polypeptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free aminogroup, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues DAP and DAPA, 4Hyp In one aspect of the invention the compound comprises the first Fibronectin III (F3,1) module of NCAM, or a fragment, or a variant thereof.

More particularly the invention relates to a compound comprising the first Fibronectin III (F3,1) module of neural cell adhesion molecule (NCAM), or a fragment, or a variant thereof capable of interacting with the FGF receptor.

Thus, in one preferred embodiment of the invention the compound comprises an amino acid sequence of the formula

L1-A-L2-B-L3-C-L4 wherein one of A, B, C is selected from a basic amino acid,
one of A, B, C is selected from a hydrophobic amino acid,
one of A, B, C is glycine, and
L1, L2, L3, L4 may be selected from a chemical bond or an amino acid sequence having n amino acid residues, wherein n is an integer of from 0 to 5.

In yet another embodiment B is glycine, A is a basic amino acid residue, and C is a hydrophobic amino acid residue.

Further, in another embodiment A is lysine (K) or arginine (R), and C is leucine (L) or alanine (A).

In another embodiment the compound of the invention comprises the sequence NGKGL (Aspargine, Glycine, Lysine, Glycine, Leucine), NGKGA, NGRGL and/or NGRGA. The sequence NGRGL is for example found in L1 and the sequence NGKGL is for example found in F3,1 of NCAM.

The invention further discloses that F3,2 is a ligand of the FGF receptor and is capable of interacting with cells presenting the FGF receptor. Thus, in another aspect of the invention the compound comprises a peptide homologous to the FG loop of the second FnIII module of the NCAM molecule, or a fragment, or a variant thereof.

A fragment comprising the FG loop of the F3,2 module of NCAM is particularly preferred. However, the invention is not limited to fragments of the F3,2 module comprising the FG loop. Deletions of such fragments generating functionally equivalent fragments comprising less than the FG loop are also comprised within the present invention. Functionally equivalent peptides and fragments thereof according to the present invention, may comprise less or more amino acid residues than the FG loop of the F3,2 module capable of binding to cells presenting an FGF receptor and/or NCAM ligands.

All functional equivalents of F3,2 peptides are included within the scope of this invention, regardless of the degree of homology that they show to a predetermined sequence of the F3,2 peptide or FG loop. The reason for this is that some parts of the binding regions are most likely readily mutatable, or capable of being peptide deleted, without any significant effect on the binding activity of the resulting fragment.

Such a peptide, fragment or variant may be a compound comprising an amino acid sequence of the formula

L1-A-L2-B-L3-C-L4-D-L5 wherein one of A, B, C, D is selected from a basic amino acid residue,
one of A, B, C, D is selected from a hydrophobic amino acid residue,
one of A, B, C, D is selected from an acidic amino acid residue,
one of A, B, C, D is glycine, and
L1, L2, L3, L4 and L5 may be selected from a chemical bond or an amino acid sequence having n amino acid residues, wherein n is an integer of from 0 to 5.

In particular a peptide, fragment or variant may be a compound comprising an amino acid sequence of the formula A-B-L3-L4-C-L4 wherein A is a hydrophobic amino acid residue,
B is an acidic amino acid residue,
L3 is one or more hydrophilic amino acid residue(s),
L4 is an amino acid sequence as defined above for L4, and
C is glycine.

In a preferred embodiment the compound comprise an amino acid sequence with the formula

AENQ-L4-G (SEQ ID NO:205), wherein A, E, N, Q, and G are the one-letter notation for amino acid residues, and L4 may be selected from a chemical bond or an amino acid sequence having n amino acid residues, wherein n is an integer of from 0 to 5.

In another embodiment a peptide, fragment or variant according to the invention may comprise a peptide homologous to the FG loop of the Fn3,2 module of the NCAM molecule, or a fragment, or a variant thereof. In one embodiment of the invention the peptide comprises a sequence having the amino acid residue motif A-E-N-Q-X-X-K, wherein X may be any amino acid residue. X may for example be selected individually from Glutamine (Q), Alanine (A), Glycine (G) and/or Asparagine (N).

In particular a peptide, fragment or variant may be a compound comprising an amino acid sequence of the formula A-L2-B-L3-L4-C-L4 wherein A is a hydrophobic amino acid residue,
L2 may be selected from a chemical bond or an amino acid sequence having n amino acid residues, wherein n is an integer of from 0 to 5
B is a basic amino acid residue,
L3 is one or more hydrophilic amino acid residue(s),
L4 may be selected from a chemical bond or an amino acid sequence having n amino acid residues, wherein n is an integer of from 0 to 5, and
C is glycine.

In a preferred embodiment the compound comprise an amino acid sequence with the formula

AM-B-L3-L4-G, wherein A, M, and G are the one-letter notation for amino acid residues, L3 is one or more hydrophilic amino acid residue(s), and L4 may be selected from a chemical bond or an amino acid sequence having n amino acid residues, wherein n is an integer of from 0 to 5.

Examples may be the following sequence: AMKEDGR (SEQ ID NO: 7)

In yet another aspect of the invention the compound is capable of binding adenosine-tri-phosphate (ATP). Without being bound by theory it is speculated that release of ATP from the synapse may effect the coupling between NCAM and the FGF-receptor and therefore regulate the axonal growth in the area of a newly formed synaptic contact, i.e. that ATP indirectly effects the plasticity in the area of synaptic contact.

In one such embodiment the compound comprises a sequence of the formula

L1-A-L2-B-L3-C-L4-D-L5-E-L6, wherein at least one of L1, L2, L3, or L4 comprises the amino acid residue Y and one of the other comprises the amino acid residue K, and L5 and/or L6 individually is K, and A, B, C, D, E is any amino acid, with the proviso, that the distance between Y and K is at least 5 amino acids, such as at least 7 amino acid residues, such as at least 9 amino acid residues, such as at least 11 amino acid residues.

It is preferred that the amino acid Y is in closer proximity to the N-terminal than the amino acid K.

In a further embodiment of the invention the compound comprises a sequence of the formula A-Xaa-B-C-C, wherein A is tyrosine (Y),
B is glycine (G),
C is lysine (K), and
Xaa is any amino acid In a preferred embodiment the compound according to the invention comprises at least one peptide comprising the sequence

| | |
|---|---|
| EVYVVAENQQGKSKA, | (SEQ ID NO 1) |
| EVAVVAENQQGASAA, | (SEQ ID NO 2) |
| VAENQQGKS, | (SEQ ID NO 3) |
| AENQQGKS, | (SEQ ID NO 4) |
| AENQQGK, | (SEQ ID NO 5) |
| AENQAGK, | (SEQ ID NO 6) |
| AMKEDGR, | (SEQ ID NO 7) |
| ALNGKGLG, | (SEQ ID NO 8) |
| AFNGRGLG, | (SEQ ID NO 9) |
| LNGKGLG, | (SEQ ID NO 10) |
| LNGKGL, | (SEQ ID NO 11) |
| ALNGKG, | (SEQ ID NO 12) |
| LNGNALGE, | (SEQ ID NO 13) |
| LNGKALG, | (SEQ ID NO 14) |
| ALNGKAL, | (SEQ ID NO 15) |
| ALNLKGLGD, | (SEQ ID NO 16) |
| LNGKELG, | (SEQ ID NO 17) |
| LTGKGLAE, | (SEQ ID NO 18) |
| LKGKGLEE, | (SEQ ID NO 19) |
| LNSKGLVE, | (SEQ ID NO 20) |
| LNGKALVE, | (SEQ ID NO 21) |
| LAAKGLGE, | (SEQ ID NO 22) |
| LDGKGL, | (SEQ ID NO 23) |
| KGLGE, | (SEQ ID NO 24) |
| DGKSLGE, | (SEQ ID NO 25) |
| NGKGL, | (SEQ ID NO 26) |
| NGRGL, | (SEQ ID NO 27) |
| QAFNGRGLGP, | (SEQ ID NO 28) |
| EVQAFNGRGLGPPAS, | (SEQ ID NO 29) |
| AALNGKGLGE, | (SEQ ID NO 30) |
| RLAALNGKGLGEIS, | (SEQ ID NO 31) |
| ALNGKGAP, | (SEQ ID NO 32) |
| VALNGKGAPR, | (SEQ ID NO 33) |
| MYVALNGKGAPRRQ, | (SEQ ID NO 34) |
| LNGRG, | (SEQ ID NO 35) |
| LNGKG, | (SEQ ID NO 36) |
| MYVALNGKGAPRRGQ, | (SEQ ID NO 37) |
| MFLALDRRGGPRPGG, | (SEQ ID NO 38) |
| MFLALDSQGIPRQGQ, | (SEQ ID NO 39) |
| MFVALNQKGIPVRG, | (SEQ ID NO 40) |
| MFVALNQKGIPVKG, | (SEQ ID NO 41) |
| MFVALNQKGLPVKG, | (SEQ ID NO 42) |
| WYVSVNGKGRPRRG, | (SEQ ID NO 43) |
| YYVALNKDGTPREG, | (SEQ ID NO 44) |
| YYVALNKDGSPREG, | (SEQ ID NO 45) |
| YFVALNKDGTPRDG, | (SEQ ID NO 46) |
| WYVALNKRGKAKRG, | (SEQ ID NO 47) |
| WYLGLNKEGEIMKG, | (SEQ ID NO 48) |
| WFLGLNKEGQIMKG, | (SEQ ID NO 49) |
| TYIALSKYGRVKRG, | (SEQ ID NO 50) |
| WFLGLNKEGQAMKG, | (SEQ ID NO 51) |
| WFLGLNKEGQVMKG, | (SEQ ID NO 52) |
| WYLGLDKEGQVMKG, | (SEQ ID NO 53) |
| WYLGLDKEGRVMKG, | (SEQ ID NO 54) |
| WYVALKRTGQYKLG, | (SEQ ID NO 55) |
| WFVGLKKNGSCKRG, | (SEQ ID NO 56) |
| ANRYLAMKEDGRLLAS, | (SEQ ID NO 57) |
| TGQYLAMDTEGLLYGS, | (SEQ ID NO 58) |
| TGQYLAMDTDGLLYGS, | (SEQ ID NO 59) |
| TGQYLAMDTSGLLYGS, | (SEQ ID NO 60) |
| TGQFLAMDTDGLLYGS, | (SEQ ID NO 61) |
| SRFFVAMSSKGKLYGS, | (SEQ ID NO 62) |
| SRFFVAMSSRGKLFGV, | (SEQ ID NO 63) |
| SRFFVAMSSRGRLYGS, | (SEQ ID NO 64) |
| SGLFVAMNSKGKLYGS, | (SEQ ID NO 65) |
| SNKFLAMSKKGKLHAS, | (SEQ ID NO 66) |
| SALFVAMNSKGRLYAT, | (SEQ ID NO 67) |
| SALFIAMNSKGRLYTT, | (SEQ ID NO 68) |
| SGRYLAMNKRGRLYAS, | (SEQ ID NO 69) |
| SEYYLAMNKEGKLYAK, | (SEQ ID NO 70) |
| SEYYLAMNKQGLYAK, | (SEQ ID NO 71) |

-continued

| | |
|---|---|
| SEFYLAMNKEGKLYAK, | (SEQ ID NO 72) |
| SGLYLGMNEKGELYGS, | (SEQ ID NO 73) |
| SGLYLGMNDKGELYGS, | (SEQ ID NO 74) |
| SGLYLGMNERGELYGS, | (SEQ ID NO 75) |
| SGLYLGMNERGELFGS, | (SEQ ID NO 76) |
| SNYYLAMNKKGKLYGS, | (SEQ ID NO 77) |
| SGFYVAMNRRGRLYGS, | (SEQ ID NO 78) |
| TGLYIAMNGEGYLYPS, | (SEQ ID NO 79) |
| ASLYVAMNGEGYLYSS, | (SEQ ID NO 80) |
| TKLYLAMNSEGYLYTS, | (SEQ ID NO 81) |
| TGLYICMNKKGKLIAKS, | (SEQ ID NO 82) |
| LGHYMAMNAEGLLYSS, | (SEQ ID NO 83) |
| TEFYLCMNRKGKLVGK, | (SEQ ID NO 84) |
| SVRYLCMGADGKMQGL, | (SEQ ID NO 85) |
| WFVGLKKNGS CKRG, | (SEQ ID NO 86) |
| WYVALKRTGQ YKLG, | (SEQ ID NO 87) |
| WYVSVNGKGR PRRG, | (SEQ ID NO 88) |
| GMFIALSKNG KTKKG, | (SEQ ID NO 89) |
| GMFMALSKNG RTKKG, | (SEQ ID NO 90) |
| GMFIALSKNG KAKKG, | (SEQ ID NO 91) |
| WYVALNKRGK AKRG, | (SEQ ID NO 92) |
| TYIALSKYGR VKRG, | (SEQ ID NO 93) |
| MFVALNQKGI PVRG, | (SEQ ID NO 94) |
| MFVALNQKGI PVKG, | (SEQ ID NO 95) |
| MFVALNQKGL PVKG, | (SEQ ID NO 96) |
| WYMAFTRKGR PRKG, | (SEQ ID NO 97) |
| YYVALNKDGT PREG, | (SEQ ID NO 98) |
| MYVALNGKGA PRRGQ, | (SEQ ID NO 99) |
| WYLGLDKEGQ VMKG, | (SEQ ID NO 100) |
| WYLGLDKEGR VMKG, | (SEQ ID NO 101) |
| WFLGLNKEGQ IMKG, | (SEQ ID NO 102) |
| WYLGLNKEGE IMKG, | (SEQ ID NO 103) |
| WFLGLNKEGQ AMKG, | (SEQ ID NO 104) |
| WFLGLNKEGQ VMKG, | (SEQ ID NO 105) |
| YYVALNKDGS PREG, | (SEQ ID NO 106) |
| WFMAFTRQGR PRQ, | (SEQ ID NO 107) |
| WFVGLKKNGS CKRG, | (SEQ ID NO 108) |
| WYVGFTKKGR PRKG, | (SEQ ID NO 109) |
| YFVALNKDGT PRDG, | (SEQ ID NO 110) |
| MFLALDRRGG PRPGG, | (SEQ ID NO 111) |
| MFLALDSQGI PRQGQ, | (SEQ ID NO 112) |
| TGQYLAMDTE GLLYGS, | (SEQ ID NO 113) |
| TGQYLAMDTD GLLYGS, | (SEQ ID NO 114) |
| TGQYLAMDTS GLLYGS, | (SEQ ID NO 115) |
| TGQFLAMDTD GLLYGS, | (SEQ ID NO 116) |
| ANRYLAMKED GRLLAS, | (SEQ ID NO 117) |
| SGRYLAMNKR GRLYAS, | (SEQ ID NO 118) |
| SRFFVAMSSK GKLYGS, | (SEQ ID NO 119) |
| SRFFVAMSSR GKLFGV, | (SEQ ID NO 120) |
| SRFFVAMSSR GRLYGS, | (SEQ ID NO 121) |
| SGLFVAMNSK GKLYGS, | (SEQ ID NO 122) |
| SNKFLAMSKK GKLHAS, | (SEQ ID NO 123) |
| SALFVAMNSK GRLYAT, | (SEQ ID NO 124) |
| SALFIAMNSK GRLYTT, | (SEQ ID NO 125) |
| SEYYLAMNKE GKLYAK, | (SEQ ID NO 126) |
| SEYYLAMNKQ GLYAK, | (SEQ ID NO 127) |
| SEFYLAMNKE GKLYAK, | (SEQ ID NO 128) |
| TGLYICMNKK GKLIAKS, | (SEQ ID NO 129) |
| SGLYLGMNEK GELYGS, | (SEQ ID NO 130) |
| SNYYLAMNKK GKLYGS, | (SEQ ID NO 131) |
| LGHYMAMNAE GLLYSS, | (SEQ ID NO 132) |
| ASLYVAMNGE GYLYSS, | (SEQ ID NO 133) |
| TKLYLAMNSE GYLYTS, | (SEQ ID NO 134) |
| TGLYIAMNGE GYLYPS, | (SEQ ID NO 135) |
| SVRYLCMSAD GKIYG, | (SEQ ID NO 136) |
| SGLYLGMNER GELYGS, | (SEQ ID NO 137) |
| SGLYLGMNER GELFGS, | (SEQ ID NO 138) |
| SEKYICMNKR GKLIG, | (SEQ ID NO 139) |
| TEFYLCMNRK GKLVGK, | (SEQ ID NO 140) |
| SVRYLCMGAD GKMQGL, | (SEQ ID NO 141) |
| SGLYLGMNDK GELYGS, | (SEQ ID NO 142) |
| TSRFLCQRPD GALYG, | (SEQ ID NO 143) |
| ASRFLCQQPD GALYG, | (SEQ ID NO 144) |
| SGFYVAMNRR GRLYGS, | (SEQ ID NO 145) |
| SRRYLCMDFR GNIFGS, | (SEQ ID NO 146) |
| TRRFLCMDLH GNIFGS, | (SEQ ID NO 147) |
| GLKKNGSC, | (SEQ ID NO 148) |
| ALKRTGQY, | (SEQ ID NO 149) |
| SVNGKGRP, | (SEQ ID NO 150) |
| IALSKNGKT, | (SEQ ID NO 151) |
| MALSKNGRT, | (SEQ ID NO 152) |

-continued

| | | |
|---|---|---|
| IALSKNGKA, | (SEQ ID NO 153) | |
| ALNKRGKA, | (SEQ ID NO 154) | |
| ALSKYGRV, | (SEQ ID NO 155) | |
| ALNQKGIP, | (SEQ ID NO 156) | |
| ALNQKGLP, | (SEQ ID NO 157) | |
| AFTRKGRP, | (SEQ ID NO 158) | |
| ALNKDGTP, | (SEQ ID NO 159) | |
| ALNGKGAPR, | (SEQ ID NO 160) | |
| GLDKEGQV, | (SEQ ID NO 161) | |
| GLDKEGRV, | (SEQ ID NO 162) | |
| GLNKEGQI, | (SEQ ID NO 163) | |
| GLNKEGEI, | (SEQ ID NO 164) | |
| GLNKEGQA, | (SEQ ID NO 165) | |
| GLNKEGQV, | (SEQ ID NO 166) | |
| ALNKDGSP, | (SEQ ID NO 167) | |
| AFTRQGR, | (SEQ ID NO 168) | |
| GLKKNGSC, | (SEQ ID NO 169) | |
| GFTKKGRP, | (SEQ ID NO 170) | |
| ALNKDGTP, | (SEQ ID NO 171) | |
| ALDRRGGPR, | (SEQ ID NO 172) | |
| ALDSQGIPR, | (SEQ ID NO 173) | |
| AMDTDGL, | (SEQ ID NO 174) | |
| AMDTEGL, | (SEQ ID NO 175) | |
| AMDTSGL, | (SEQ ID NO 176) | |
| AMKEDGR, | (SEQ ID NO 177) | |
| AMNKRGR, | (SEQ ID NO 178) | |
| AMSSKGK, | (SEQ ID NO 179) | |
| AMSSRGK, | (SEQ ID NO 180) | |
| AMNSKGK, | (SEQ ID NO 181) | |
| AMSKKGK, | (SEQ ID NO 182) | |
| AMNSKGR, | (SEQ ID NO 183) | |
| AMNKEGK, | (SEQ ID NO 184) | |
| AMNKEGK, | (SEQ ID NO 185) | |
| AMNKQGL, | (SEQ ID NO 186) | |
| CMNKKGK, | (SEQ ID NO 187) | |
| GMNEKGE, | (SEQ ID NO 188) | |
| AMNKKGK, | (SEQ ID NO 189) | |
| AMNAEGL, | (SEQ ID NO 190) | |
| AMNGEGY, | (SEQ ID NO 191) | |
| AMNSEGY, | (SEQ ID NO 192) | |
| AMNGEGY, | (SEQ ID NO 193) | |
| CMSADGK, | (SEQ ID NO 194) | |
| GMNERGE, | (SEQ ID NO 195) | |
| CMNKRGK, | (SEQ ID NO 196) | |
| CMNRKGK, | (SEQ ID NO 197) | |
| CMGADGK, | (SEQ ID NO 198) | |
| GMNDKGE, | (SEQ ID NO 199) | |
| LCQRPDG, | (SEQ ID NO 200) | |
| LCQQPDG, | (SEQ ID NO 201) | |
| AMNRRGR, | (SEQ ID NO 202) | |
| CMDFRGN, and/or | (SEQ ID NO 203) | |
| CMDLHGN | (SEQ ID NO 204) | |

The sequences listed above may be part of naturally occurring proteins, for example the peptide having the sequence of AMKEDGR (SEQ ID NO 7) is found in the Fibroblast Growth factor 2 (FGF 2).

In one embodiment of the invention the sequences 86-206 are homologue sequences to the FGL peptide (FG loop peptide) in the F3,I and F3,II domains.

By the term "homologue" is meant a sequence which is structurally and/or functionally identical with the FGL peptide of the invention. Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

In one embodiment of the invention the compound is capable of interacting with the Fibroblast Growth Factor (FGF) receptor. A variety of FGF receptors exist. It is preferred that the FGF receptor may be selected from FGF receptor I, FGF receptor II, FGF receptor III, FGF receptor IV. In a more preferred embodiment the FGF receptor I signalling is stimulated.

In a preferred embodiment of the invention the interaction of the present compound with the FGF receptor is resulting in the stimulation of FGF receptor signalling. When the compound of the invention interacts with the FGF receptor a cascade of chemical events and physiological changes occurs. The interaction of the present compound with the FGF receptor causes presumably conformational changes or clustering of the receptor by which chemical signals are created and propagated from the site of interaction to the inside of the cell. The signals are said to be transduced from the outside to the inside of the cell, the latter resulting in a physiological response of the cell.

According to the invention the FGF receptor signalling is measured as phosphorylation of the FGF receptor when a predetermined concentration of the compound is applied to cells expressing the FGF receptor. The degree of phoshorylation is at least 20% above the control value, such as at least 20-200%, for example at least 50-200%.

When testing the present compound with respect to for example measuring signalling the concentration of the said compound may be between 0.1-1000 µM, 1-1000 µM, for example 1-200 µM, for example 10-200 µM, such as 20-180

μM, for example 30-160 μM, such as 4-140 μM, for example 50-130 μM, such as 60-120 μM, for example 70-110 μM, such as 80-100 μM.

The amino acid sequence of the compound of the invention may be of any suitable length, in that the length of the amino acid sequence is dictated by the functionality of the peptide and the formulation of the compound into a pharmaceutical composition. Thus, the compound normally comprises amino acid residues in the range of from 3-100 amino acid residues, such as from 10-90 amino acid residues, for example from 15-85 amino acid residues, such as from 20-80 amino acid residues, for example from 25-75 amino acid residues, such as from 30-70 amino acid residues, for example from 35-65 amino acid residues, such as from 40-60 amino acid residues, for example from 45-55 amino acid residues.

In another aspect the compound comprises amino acid residues in the range of from 3 to 20 amino acid residues, such as from 3-19 amino acid residues, for example from 3-18 amino acid residues, such as from 3-17 amino acid residues, for example from 3-16 amino acid residues, such as from 3-15 amino acid residues, for example from 3-14 amino acid residues, such as from 3-13 amino acid residues.

The peptides of the invention may serve as tools for identifying a motif in peptide ligands expected to bind to the FGF receptor and/or ATP. Such peptide ligands may be found through a peptide and/or a non-peptide library. Any peptide sequence comprising said peptides capable of binding the FGF receptor and/or ATP and/or L1 are part of the present invention.

These mentioned compounds and compositions can be used to treat conditions affecting the peripheral and/or the central nervous system and/or muscles and other tissues expressing FGF receptors or NCAM ligands as well as other conditions in which a stimulation of FGF receptor function or the function of other NCAM ligand is beneficial.

Putative artificial ligands may be selected and identified from peptide or non-peptide libraries. Any peptide or non-peptide library may be used. Synthetic peptide and non-peptide libraries as well as libraries containing fragmented natural occurring proteins, may be used in the search for useful peptides. Any kind of libraries comprising non-peptide compounds may similarly be used.

Peptides characterised by a certain sequence of amino acids may be a variant of a certain area of a protein. Naturally occurring proteins consist of L-amino acid residues. However, artificial peptides may also consist of or comprise D-amino acid residues. By combinatorial chemistry, mixtures of beads carrying peptides of equal length can be constructed, in which each bead carries peptides of a unique sequence (Lam et al., 1991). Such a mixture of peptides on beads is called a peptide library.

In the present invention, peptides, fragments or variants may be identified by screening synthetic random peptide libraries comprising resin-bound peptides with purified recombinant NCAM or recombinant FGF receptor or recombinant L1 or other NCAM ligands. The synthesis of the resin-bound one-bead one-peptide library may be performed using the portioning, mix procedure of Furka, À., Sebestyyén, F., Asgedom, M. And Dibó, G. (1991) Int. J. Pep. Prot. Res. 37, 487-493) optionally modified as known to the person skilled in the art. It is to be understood that the method chosen for identification and selection of interesting peptides is not critical for the identification of a putative motif.

Libraries of small organic compounds may be screened to identify FGF receptor ligands or L1 ligands or other NCAM counter-receptor ligands capable of interacting with Fibroblast Growth Factor (FGF) receptor and/or Adenosine-Tri-Phosphate (ATP) and/or L1. Such libraries or their construction are commonly known and the screening for useful ligands may follow the methods for screening disclosed in the present specification, or in ways obvious to the skilled person.

The compound of the present invention may preferably be in the form of an oligomer (multimer) of monomers, wherein each monomer is as defined for the compound above. Particularly, multimeric peptides such as dendrimers may form conformational determinants or clusters due to the presence of multiple flexible peptide monomers. In one embodiment the compound is a dimer. In a more preferred embodiment the compound is a dendrimer, such as four peptides linked to a lysine backbone, or coupled to a polymer carrier, for example a protein carrier, such as BSA. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be lipophilic dendrimers, or micelle-like carriers formed by lipophilic derivatives, or starburst (star-like) carbon chain polymer conjugates.

The compound preferably comprises monomers independently capable of stimulating FGF receptor signalling and/or modulating proliferation and/or differentiation, regeneration, survival and/or neuronal plasticity of cells presenting an FGF receptor and/or NCAM ligand/counterreceptor and/or L1.

The individual monomers may be homologous, i.e. identical to one another, or the individual monomers may be heterologous, i.e. different from one another. The latter type of monomers may comprise at least two different monomers. In general dimers and multimers may comprise two or more identical monomers, or two or more monomers different from one another.

Pharmaceutical Composition

The invention also relates to a pharmaceutical composition comprising one or more of the compounds defined above comprising the third Immunoglobulin (Ig3) module, and/or the fourth Immunoglobulin (Ig4) module, and/or the fifth Immunoglobulin (Ig5) module, and/or the first Fibronectin III (Fn3,1) module, and/or the second Fibronectin III (Fn3,2) module of neural cell adhesion molecule (NCAM), or a fragment, or a variant thereof, wherein the compound is capable of interacting with an Fibroblast Growth Factor (FGF) receptor and/or Adenosine-Tri-Phosphate (ATP) and/or L1.

In the present context the term "pharmaceutical composition" is used synonymously with the term "medicament".

In one embodiment the pharmaceutical composition comprises the NCAM F3,2 module, or a fragment thereof, or a variant thereof. In another embodiment the composition comprises the NCAM F3,1 module, or a fragment thereof, or a variant thereof.

The compositions are preferably formulated as multimers or dimers as discussed above.

The invention further concerns a pharmaceutical composition capable of stimulating FGF receptor signalling and/or modulating proliferation and/or inducing differentiation and/or stimulating regeneration, neuronal plasticity and/or survival of cells presenting an FGF receptor.

The pharmaceutical composition may in one aspect prevent death of cells in vitro or in vivo, wherein the composition is administered to a subject, in vitro or in vivo in an effective amount of one or more of the compounds described above or a composition as described below, so as to prevent cell death of FGF receptor presenting cells and/or L1 presenting cells in several tissues and organs as discussed herein.

The medicament of the invention comprises an effective amount of one or more of the compounds as defined above, or a composition as defined above in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For most indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, modulating proliferation, stimulate regeneration, neuronal plasticity and survival of FGF receptor presenting cells or L1 presenting cells or other NCAM ligand presenting cells in vitro or in vivo, the treatment involving administering an effective amount of one or more compounds as defined above.

Another strategy for administration is to implant or inject cells capable of expressing and secreting the compound in question. Thereby the compound may be produced at the location where it is going to act.

Treatment

In a further aspect, the present invention relates to said peptides, fragments, or variants thereof for use in the modulation of proliferation and/or induction of differentiation and/or stimulation of regeneration, neuronal plasticity and/or survival of cells presenting an FGF receptor. The use is for the treatment for preventing diseases and conditions of the central and peripheral nervous system, and of the muscles or of various organs.

Treatment by the use of the compounds/compositions according to the invention is in one embodiment useful for inducing differentiation, modulating proliferation, stimulate regeneration, neuronal plasticity and survival of cells being implanted or transplanted. This is particularly useful when using compounds having a long term effect.

In further embodiment the treatment may be for stimulation of survival of cells which are at risk of dying due to a variety of factors, such as traumas and injuries, acute diseases, chronic diseases and/or disorders, in particular degenerative diseases normally leading to cell death, other external factors, such as medical and/or surgical treatments and/or diagnostic methods that may cause formation of free radicals or otherwise have cytotoxic effects, such as X-rays and chemotherapy. In relation to chemotherapy the NCAM binding compounds according to the invention are useful in cancer treatment of all cancer cells presenting NCAM ligands.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

Furthermore, the compound and/or pharmaceutical composition may be for preventing cell death of heart muscle cells, such as after acute myocardial infarction, in order to induce angiogenesis. Furthermore, in one embodiment the compound and/or pharmaceutical composition is for the stimulation of the survival of heart muscle cells, such as survival after acute myocardial infarction. In another aspect the compound and/or pharmaceutical composition is for revascularisation, such as after injuries.

It is also within the scope of the invention to use the compound and/or pharmaceutical composition for the promotion of wound-healing. The present compounds are capable of stimulating angiogenesis and thereby promote the wound healing process.

The invention further discloses the use of the compound and/or pharmaceutical composition in the treatment of cancer. NCAM regulates motility and inhibits cancer cells from spreading.

In yet a further embodiment the use of the compound and/or pharmaceutical composition is for the stimulation of the ability to learn and/or of the short and/or long term memory.

In particular the compound and/or pharmaceutical composition of the invention may be used in the treatment of clinical conditions, such as Neoplasms such as malignant neoplasms, benign neoplasms, carcinoma in situ and neoplasms of uncertain behavior, diseases of endocrine glands, such as diabetes mellitus, psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nervesystem and sense organs, cognitive anomalies, inflammatory disease of the central nervous system, such as meningitis, encephalitis, Cerebral degenerations such as Alzheimer's disease, Pick's disease, senile degeneration of brain, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the ear and mastoid process, chronic rheumatic heart disease, ischaemic heart disease, arrhythmia, diseases in the pulmonary system, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide. Thus, in a further aspect, the present invention relates to a prosthetic nerve guide, characterised in that it comprises one or more of the compounds or the pharmaceutical composition as defined above. Nerve guides are known in the art.

Another aspect of the invention relates to the use of a compound as defined above. In particular the use of a compound according to the invention is for the production of a pharmaceutical composition. The pharmaceutical composition is preferably for the treatment or prophylaxis of any of the diseases and conditions mentioned above.

In yet a further aspect the invention relates to a method of treating a disease or condition as discussed above by administering a compound as defined herein.

Experimental

The following are non-limiting examples illustrating the present invention.

Materials and Methods

Methods

The $^{15}$N-labelled and unlabelled protein corresponding to aminoacids 612-705 of rat NCAM (swissprot p13596) was produced in yeast P. pastoris. The expression product contains two N-terminal residues, A and G, from the vector and is sequentially numbered from 1 to 96. 2 mM unlabelled and 1 mM $^{15}$N-labelled protein (in 30 mM NaCl, 10 mM sodium phosphate buffer, pH 7.27) were used. The $^{1}$H and $^{15}$N resonances were assigned from spectra of DQF-COSY, TOCSY, $^{15}$N TOCSY-HSQC NMR experiments. All data were acquired at 298 K. The NOE constraints were derived from 80/200 ms NOESY and 125 ms $^{15}$N-NOESY-HSQC spectra with upper bounds of 2.7. 3.3 and 6.0 Å increased by 0.5 Å if the constraint included a methyl group. 40 φ angles restraints with bounds of −120±40° and −57±40° (derived from the $^{3}J_{HNH\alpha}$ coupling constants) and 4 $\chi^{1}$ angles (for valines) were applied. 96 structures were generated with a distance geometry/simulated annealing protocol using the X-PLOR program. After inspection of hydrogen bond energies, 80 hydrogen bond restraints were applied with upper bounds of 2 Å and 3 Å for the NH—O and N—O distances, respectively. All the structures had NOE violations of less than 0.3 Å, and rms deviations from idealized geometry for bond lengths and angles of less than 0.01 Å and 20°, respectively.

HEK293 Cell Culture and Transfection

Cells were grown in DMEM 1965 with 10% FCS, 100 U/ml penicillin, 100 µg/ml streptomycin and 58.4 g/l Glutamax. ~0.8*10$^{6}$ cells were plated in 60 mm plates and cultured for 24 hrs before being transfected using LipofectAMIN PLUS™ reagent kit according to manufacturers instructions (Gibco BRL) with 0.2 µg PcDNA3.1(+) plasmid encoding a his-tagged (C-terminal hexa-histidine) version of FGFR-1. Cells were grown another 24 hrs in full medium, and then shifted to starving media (DMEM 1965 with 0.5% FCS) overnight.

Stimulation, Purification and Western Blot Analysis

FGFR-1 transfected cells, incubated with 50 µg/ml NCAM derived recombinant fIII.2 or FG-loop for 20 minutes or non-stimulated, were lysed in 8M urea in PBS with 1 mM orthovanadate. The FGFR-1 was purified from total lysate via the His-tag moiety on an IMAC column. Equal amounts of lysate were loaded on Ni$^{2+}$/NTA-sepharose (Qiagen), washed in lysis buffer with 10 mM imidazole, and his-tagged FGFR-1 was eluted in lysis buffer with 250 mM imidazole. Samples were added SDS-PAGE sample buffer and analysed by western blotting using anti-pentahis ab (#34660 Qiagen) or anti-phosphotyrosine ab (PY20) (#11120 Transduction Laboratories). Bands were visualised by chemilumiscense and density was measured using a GeneGnome from SynGene with a 16 bit camera.

Neurons were grown on Permanox plastic (Nunc, Denmark) for 24 h at a density 6250 cells/cm$^{2}$, at 37° C., 5% CO$_{2}$ in Neurobasal medium containing 20 mM Hepes, 100 U/ml penicillin, 100 µg/ml streptomycin, 0.4% BSA supplemented with B27 (Gibco BRL, USA). After 24 h, cells were fixed with paraformaldehyde, stained with Coomassie Brilliant Blue R250 and analyzed.

To study the structural and functional properties of the second F3 module of NCAM as well as a possible interaction with the FGF-receptor, the recombinant proteins of the second F3 module of NCAM and the second and third Ig modules of the FGF-receptor were produced in the yeast expression system of P. pastoris. This expression system was selected because P. pastoris is capable of protein folding and processing similar to higher eukaryotes, and the protein secreted into the medium can be purified easily.

Example 1

Structure of the Second F3 Module of NCAM

The three-dimensional structure of the module was derived from 1434 experimentally determined restraints (15 restraints per residue): 1322 structurally significant nuclear Overhauser enhancement (NOE) distance restraints (as determined by means of the program DIANA), 44 dihedral angle restraints (40 φ and 4 $\chi$1), and 68 hydrogen bond restraints. An overlay of 30 superimposed structures for the backbone atoms is shown in FIG. 1a. The global root mean square (rms) deviation (rmsd) from the average of the 30 superimposed structures is 0.25 Å for the backbone atoms and 0.68 Å for the heavy atoms. A ribbon representation of the structure labeling the seven β-strands is shown in FIG. 1b. The summary of the NOE statistics, energy terms and deviations from the idealized geometry is shown in Table 1.

TABLE 1

| a) Structural statistics | | | |
|---|---|---|---|
| $^{1}$Number of restraints | 1434: | $^{3}$Structural precision: | |
| Long range NOE restraints | 717 | Rms deviation for backbone atoms | 0.25 Å |
| Medium range NOE restraints | 122 | Rms deviation for heavy atoms | 0.68 Å |
| Sequential NOE restraints | 364 | Rms deviations from idealized geometry: | |
| Intra NOE restraints | 119 | bonds | 0.0027 ± 0.0000 Å |
| Dihedral angle restraints | 44 | bond angles | 1.4558 ± 0.0075° |
| Hydrogen bond restraints | 80 | improper bond angles | 0.8674 ± 0.0198° |

TABLE 1-continued a) Structural statistics

[2]Energies (kcal/mol):

| | | | |
|---|---|---|---|
| Bonds | 2.23 ± 0.05 | no restraints | 5.02 ± 0.36 |
| Bond angles | 191.2 ± 0.8 | dihedral angle restraints | 0.004 ± 0.005 |
| hydrogen bonds | −157.5 ± 7.1 | van der Waals | −395.9 ± 7.2 |
| Dihedral bond angles | 494.2 ± 11.4 | improper bond angles | 24.9 ± 2.2 |
| Overall | 164 ± 11.4 | | |

[1]Number of non-redundant restraints.
[2]The energies were calculated using CHARMM force field with force constants for NOE's of 10 kcal mol$^{-1}$ Å$^{-2}$ and for dihedral constraints of 200 kcal mol$^{-1}$ rad$^{-2}$.
[3]Rms deviations from the average for residues 3-96 in 30 structures. Residues 1-2 are extra residues from the vector DNA.

The structure consists of seven antiparallel β-strands arranged in a sandwich of two β sheets, one containing three strands (ABE) and the other four strands (GFCD). Both of the β sheets have a right-handed twist. The triple-stranded β sheet consists of residues Lys 7-Gly 13 (A), Ser 18-Ile 24 (B), His 59-Lys 63 (E), and the four-stranded β sheet consists of residues Ile 33-Ala 42 (C), Ile 51, Arg 52 (D), Glu 70-Asn 79 (F) and Gly 82-Arg 92 (G). Identification of the elements of the secondary structure was performed using the programs PROCHECK and MOLMOL. There are two wide type β-bulges (Chan et al., 1993) involving residues Lys 85, Ala 86 and Val 76 (G and F β-stands), and residues Ala 77 and His 35, Tyr 36 (F and C β-strands). The two β-bulges contribute to the right-handed twist conformation of the four-stranded β-sheet. The β-hairpins formed by the A and B β-strands, and the G and F β-strands are well defined. The β-hairpin between the A and B strands corresponds to a 4:6 type I turn with the average φ, ψ values for Glu 14 (i+1 residue) being −64±1°, 12±2°, and for Asp 15 (i+2 residue) −80±1°, 24±2°; whereas the β-hairpin between the G and F strands corresponds to a tight 2:2 type I turn with the average φ, ψ values for Gln 80 (i+1 residue) −38±3°, −42±40, and for Gln 81 (i+2 residue) −107±13°, 28±30° (Sibanda et al., 1989; Wilmont and Thornton, 1990). The loops between the D-E and E-F strands appear to be distorted type II turns with the average φ, ψ values for i+1 residues being −70±8°, 93±17° (Ser 55, D-E loop), −73±20°, 154±3° (Trp 67, E-F loop), and the average φ, ψ values for i+2 residues being 109±9°, 57±8° (Gly 56, D-E loop), 46±3°, 48±2° (Asn 68, E-F loop). The hydrophobic core, which is enclosed by the two β-sheets, consists of residues Leu 8, Met 12, Ile 19, Val 21, Leu 23, Ile 33, Tyr 36, Val 38, Tyr 40, Ala 42, Ile 51, Leu 53, Val 60, Leu 62, Leu 65, Tyr 71, Val 73, Val 75, Ala 77, Ala 87, Phe 89, Phe 91, and Thr 93. Interestingly, the two tryptophans Trp 47 and Trp 67, located in the C-D and E-F loops, respectively, and Tyr 74 (F strand) are exposed on the surface of the module, and they are not part of the hydrophobic core.

All of the 30 structures conform to the commonly applied acceptance criteria: no violations larger than 0.5 Å for NOE restraints and larger than 5° for dihedral angle restraints, root mean square deviations from idealized geometry for bond lengths and bond angles less than 0.01 Å and 2°, respectively. The quality of each structure was assessed using the program WHAT IF. The average Z-scores for the set of 30 structures are: −1.42±0.17 for the $2^{nd}$ generation packing quality, −1.94±0.27 for the Ramachandran plot, −1.53±0.34 for the $\chi_1/\chi_2$ plot, and −2.10±0.20 for the backbone conformation. The quality of the 30 structures was further analyzed using the program PROCHECK. All of the analyzed main-chain and side-chain parameters were found to be within the normal ranges when compared to the X-ray structures of 2.0 Å resolution. The number of residues in the most favored region of the Ramachandran plot is 75.3%. NOE violations were analyzed using the program AQUA. The maximum NOE violation is 0.25 Å, and the rms NOE violation is 0.0189±0.00067 Å.

Example 2

The Second F3 Module of NCAM Binds to the FGF-Receptor and ATP

Given the assignment of the NMR spectra of the module and its known three-dimensional structure, it is possible to locate the residues that form the binding site on the surface of the module. In the $^{15}$N-HSQC spectrum of the $^{15}$N-labeled protein, a signal for each amino acid with both a peptide nitrogen and proton can be observed. The changes in the chemical shifts of the signals provide a method for the identification of residues in a protein that are perturbed by the binding of another molecule. To the 0.05 mM $^{15}$N-labeled sample of the second F3 module of NCAM, 1 mM unlabeled the second or third Ig modules of the FGF-receptor, or 5 mM AMP-PCP (an non-hydrolysable analogue of ATP) were added. No significant changes of the chemical shifts were found in the presence of the second Ig module of the FGF-receptor (data not shown). The recorded changes of the chemical shifts in the presence of the third Ig module of the FGF-receptor or ATP are shown in FIG. 2a-d. The changes in $^1$H and $^{15}$N chemical shifts in the presence of the third Ig module of the FGF-receptor were mapped onto the structure of the module (FIG. 2e), using a cutoff of 0.006 p.p.m. and 0.03 p.p.m. for the perturbed $^1$H and $^{15}$N chemical shifts, respectively.

The residues of the F3 module that experienced significant perturbation by the third Ig module of the FGF-receptor were Tyr 36, Leu 37, Val 38, Tyr 40, Leu 53, Tyr 71, Tyr 74, Val 75, Val 76, Ala 77, Asn 79, Gln 81, Gly 82, Lys 83, Ser 84, Lys 85, Ala 87, His 88, Phe 89, Val 90 (FIGS. 2a,b). The changes of the chemical shifts of these residues demonstrate that the presence of the third Ig module of the FGF-receptor close to the second F3 module of NCAM alters the chemical environment at the perturbed residues of the F3 module. The perturbed residues are located in one well defined and coherent patch on the surface of the module, indicating that the perturbed residues are either a part or in the vicinity of the binding site for the interaction between the second F3 module of NCAM and the third Ig module of the FGF-receptor (FIG. 2E). The surface area of the perturbed residues is approximately 2600 Å$^2$, which is significantly larger than the 1000 Å$^2$ minimal area generally considered to be required for a biologically specific interaction. However, the surface area of the binding site is likely to be smaller, since some of the perturbed residues probably are just located close to the site.

Figure 2F:
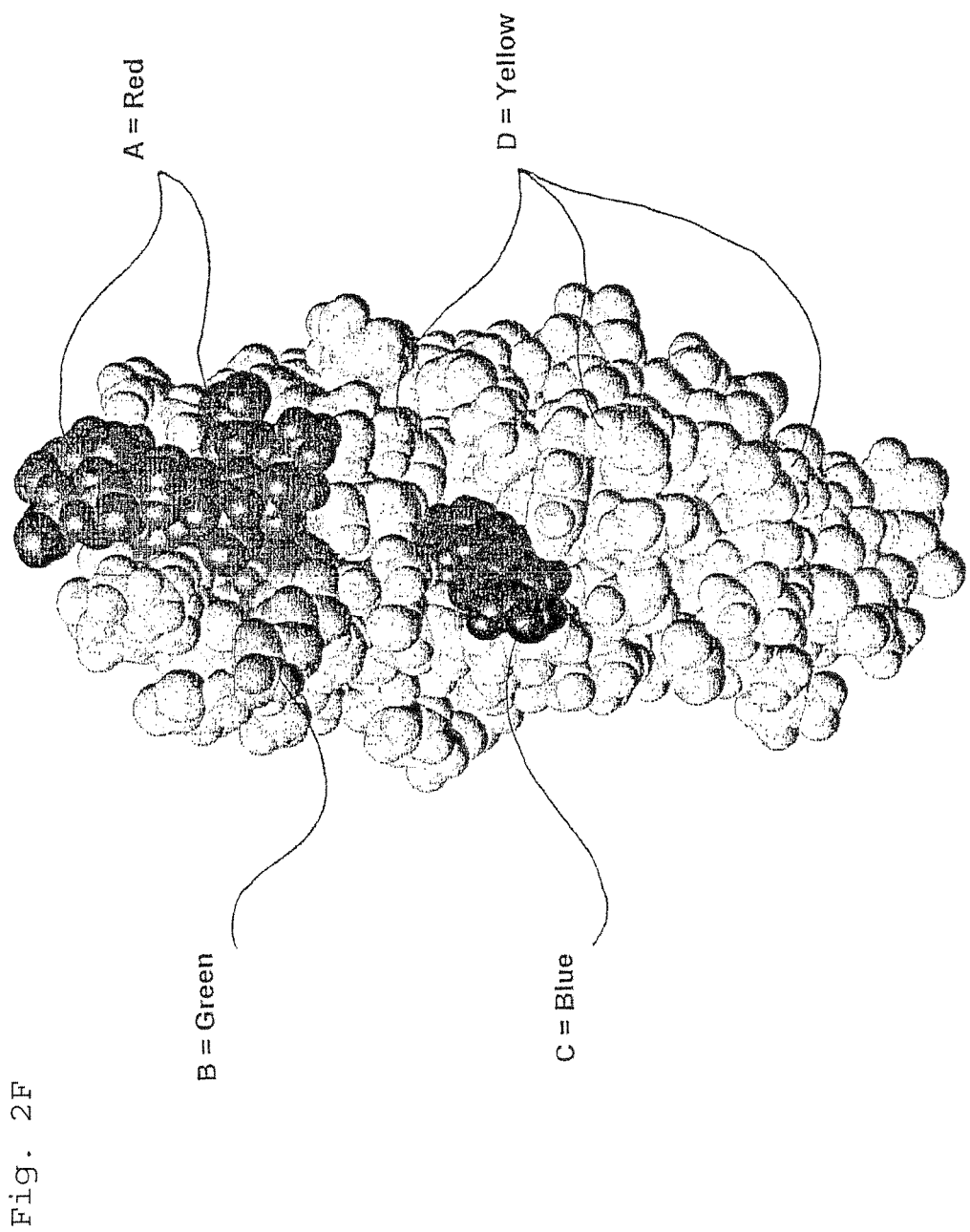
Figure 2G:
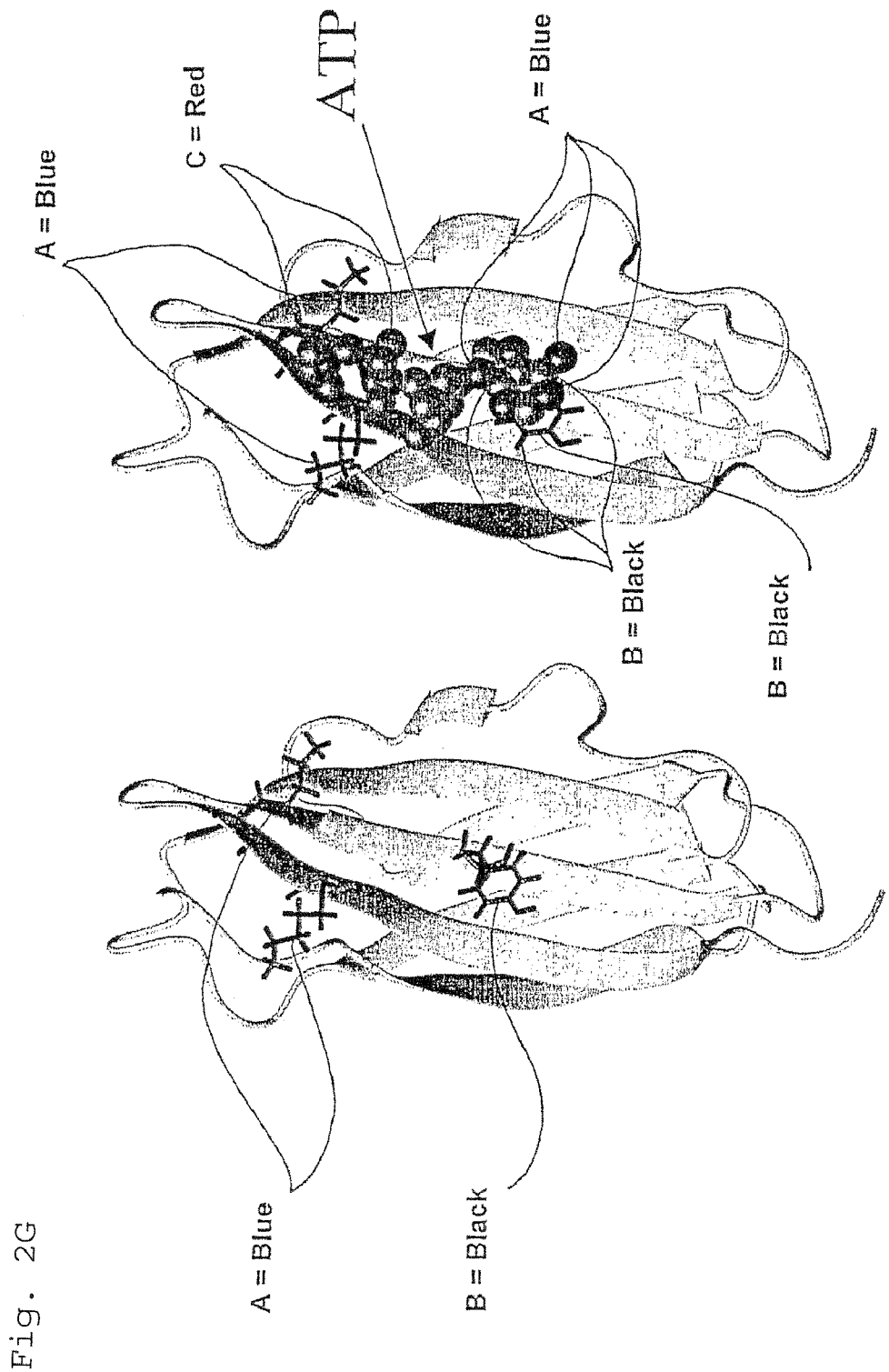

The residues of the F3 module perturbed by AMP-PCP were Tyr 74 and Val 75 (FIG. 2c-d). The side chain of Tyr 74 is exposed on the surface of the module and is located in the close vicinity of the ATP-binding consensus sequence of the module: Ala 77-Glu-Asn-Gln-Gln-Gly-Lys-Ser 84 and Lys 85 (FIG. 2f). Both Lys 83 and Lys 85 are exposed on the surface of the module and it is possible that the positively charged side chains of Lys 83 and Lys 85 interact with the negatively charged triphosphate moiety of ATP, whereas the side chain of Tyr 74 is involved in hydrophobic interaction with the adenosine moiety of ATP. A possible arrangement of the complex of ATP and the second F3 module is depicted in FIG. 2g. The residues perturbed by ATP (Tyr 74 and Val 75) were also perturbed by the third Ig module of the FGF-receptor, indicating that the ATP binding site and the FGF-receptor binding site are overlapping.

Example 3

The FGF-Receptor is Activated by the Second F3 Module of NCAM and by the FGL Peptide Since the above NMR experiments demonstrate binding of the second F3 module of NCAM to the FGF-receptor, it was of interest to test if this binding can induce FGF-receptor activation in living cells. Therefore, HEK293 cells were grown for 24 h on plastic plates, and subsequently transfected with a His-tagged version of the FGF-receptor 1 and cultured for another 24 h. After incubation of the cells for 20 min with the below described compounds, cells were lysed in 8M urea and the FGF-receptor was purified from the total lysate via the His-tag moiety. The purified FGF-receptor 1 was then analyzed by immunoblotting using antibodies either to the His-tag or phosphotyrosine. FGF-receptor activation was estimated by the level of the FGF-receptor phosphorylation.

From FIG. 3, it appears that addition of 5 µM second F3 module of NCAM increased FGF-receptor phosphorylation by approx. 150% compared to control cells. Most of the residues of the second F3 module of NCAM perturbed by the third Ig module of the FGF-receptor are located in the F, G β-strands and the FG turn region of the NCAM module. We therefore tested whether a synthetic peptide spanning these residues could variant the second F3 module in its ability to activate the FGF-receptor. Indeed, addition of a peptide corresponding to residues Glu 72-Ala 86 (termed the FG loop peptide) at a concentration of 25 µM also activated the FGF-receptor, increasing phosphorylation by approx. 100%, thus supporting the notion that these residues of the second F3 module are involved in the binding to the FGF-receptor (FIG. 3).

Thus, the present data demonstrate that binding of the second F3 module of NCAM to the FGF-receptor results in the activation of the latter.

Example 4

Activation of the FGF-Receptor by the Second F3 Module of NCAM Stimulates Neurite Growth Because the second F3 module of NCAM and its FGF-receptor binding part (the FG loop peptide) activate the FGF-receptor, it may be expected that the F3 module and the FG loop peptide are capable of mimicking a characteristic function of NCAM stimulation: neuronal differentiation as reflected by neuritogenesis. To test this assumption, dissociated neurons from embryonic rat hippocampus were seeded on plastic and allowed to grow for 24 h in the presence of the below described compounds. Thereafter, cells were fixed with paraformaldehyde, stained with Coomassie Brilliant Blue R250 and the length of neurites was measured using a stereological approach (Rønn et al., 2000).

As can be seen from the phase-contrast pictures (FIGS. 4a,b), addition of the second F3 module of NCAM at a 5 µM concentration substantially increased the length of neurites per cell as compared to the control, non-stimulated neurons. The effect was quantified in a dose-response study (FIG. 4c) demonstrating that the F3 module, the FG loop peptide and a truncated version of the peptide (Ala 77-Lys 83) all induced neurite outgrowth, with a bell-shaped dose-response curve typical of growth factor induced neuritogenesis (Hatten et al., 1988). The potency of the peptides was lower than that of the module, as reflected by the fact that a 10 times higher concentration was required for maximum effect, and the truncated form was less efficient than the extended form. The stimulatory effect of the second F3 module and the FG loop peptide could be abrogated by an inhibitor of NCAM-stimulated neurite outgrowth, an antibody against the FGF-receptor. The effect of the antibody under control conditions and on neurite outgrowth induced by the second F3 module or the FG loop, is shown in FIG. 4d. In the latter case, a complete inhibition was achieved, further supporting the notion that the module and the FG loop peptide interact with the FGF-receptor.

Figures 6A, 6B:
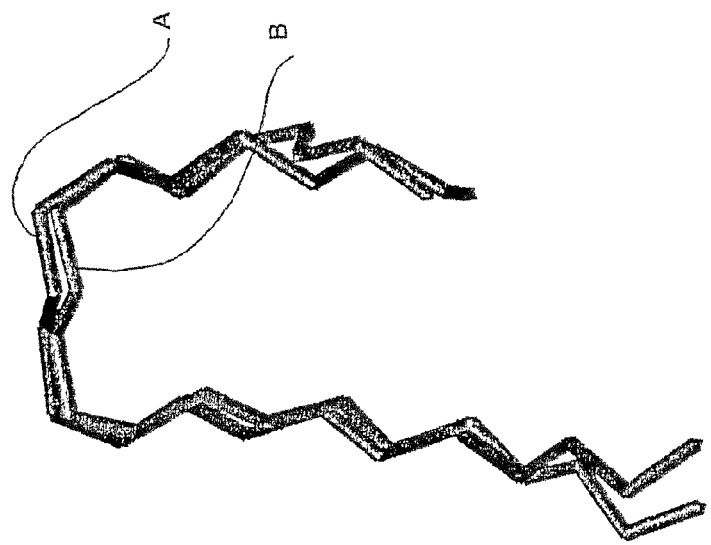

To determine the functionally important amino acids of the FG loop peptide, the peptide was analyzed by truncations and alanine substitutions of various amino acids. Two truncated versions (from the N— and C-terminal) of the FG loop peptide were produced: the nonamer Val 76-Ser 84 and the heptamer Ala 77-Lys 83. Even though the truncated peptides were substantially shorter than the FG loop peptide, they both retained approximately 50% of the stimulatory effect as compared to the entire FG loop peptide (FIG. 5a), indicating that the turn region between the F and G β-strands (Gln 80, Gln 81) and a few adjacent amino acids from both sides of the turn are important for the interaction between the FGF-receptor and the second F3 module of NCAM. The heptameric peptide was subsequently analyzed by a so-called Ala-scan in which a series of peptides, in which each amino acid sequentially was substituted with an alanine, were tested. As can be seen from FIG. 5a, substitution of any amino acid in the peptide resulted in a decrease of the neuritogenic potency and a complete loss of function was achieved if Glu 78, Asn 79, Gln 80, Gly 82, Lys 83 were substituted with Ala, indicating that these residues are important for interaction with the FGF-receptor. Double substitution of the two amino acids from the turn region of the FG loop (Gln 80, Gln 81) for alanines in the entire FG loop peptide also resulted in a complete inactivation of the peptide (FIG. 5a). These findings are corroborated by the fact that Asn 79, Gln 81, Gly 82 and Lys 83 were perturbed in the second F3 module by binding to the third module of the FGF-receptor. However, when the residues which seem to be important for interaction with ATP (Tyr 74, Lys 83 and Lys 85) were substituted for alanines in the FG loop peptide, the peptide retained about 60% of the stimulatory effect as compared to the non-mutated peptide (FIG. 5a). The structure of the heptameric peptide in the F3 module was compared to the known three-dimensional structure of a natural ligand of the FGF-receptor, basic FGF (PDB code: 4FGF, Eriksson et al., 1993), and it was found that the peptide had a structure and sequence similarity to a loop region in basic FGF, Ala 42-Arg 48. The sequence and structure alignment of both of the peptides is shown in FIGS. 6a, b. The heptameric peptide derived from basic FGF and a series of peptides with Ala substitutions were tested for their capability to induce neritogenesis, and as can be seen from FIG. 5b, the peptide derived from basic FGF induced neurite outgrowth to the same extent as the similar seven amino acids from the second F3 module of NCAM. Substitution of any amino acid for alanine resulted in a complete loss of function.

Since ATP inhibited activation of the FGF-receptor by the second F3 module of NCAM (FIG. 3), it was presumed that ATP also could inhibit the neuritogenic activity of the module. To test this assumption, neurons were stimulated with the below described compounds in the presence of ATP or a non-hydrolysable analogue of ATP, AMP-PCP (added at concentrations of 0, 0.4 or 1 mM). As can be seen from FIG. 7, both ATP and AMP-PCP substantially reduced the neuritogenic effect induced by the second F3 module and the FG loop peptide, whereas when these compounds were added alone, they did not have any effect. In case of AMP-PCP, a complete inhibition was achieved of the effect of both the F3 module and the FG loop peptide, and in case of ATP, a complete inhibition was achieved only of the effect of the FG loop, indicating that ATP is a less potent inhibitor than its non-hydrolysable analogue AMP-PCP. Most significantly, when the amino acid residues of the FG loop presumed to be of importance for ATP binding (Tyr 74, Lys 83 and Lys 85) were substituted with alanines, the peptide retained its neuritogenic potency. However, the stimulatory effect of the peptide could no longer be inhibited by ATP (FIG. 7), supporting the notion that ATP binding regulates interaction between the F3 module and the FGF-receptor.

These results indicate that activation of the FGF-receptor in neurons by the second F3 module of NCAM induces neuritogenesis and this effect can be inhibited by ATP.

Example 5

Survival Assay for Testing Compounds of the Invention

Cerebellar granule neurons (CGN) from 7-days old rats are grown for 7-8 days in the presence of high potassium (40 mM). Cells are washed twice with serum-free culture medium (basal Eagle's medium BME) containing low potassium (5 mM) and grown in serum-free medium supplemented with FGL peptide for two days. Cultures are assayed for cell survival (D'Mello et al., 1997; Villalba et al., 1997; Skaper et al., 1998) by measuring reduction of MTS. MTS is a novel tetrazolium compound (Promega, USA), which is bioreduced by cells into a formazan that is soluble in tissue culture medium. The absorbance of the formazan at 490 nm is measured directly from 96 well assay plates without additional processing. The conversion of MTS into the aqueous soluble formazan is accomplished by dehydrogenase enzymes found in metabolically active cells. The quantity of formazan product as measured by the amount of 490 nm absorbance is directly proportional to the number of living cells in culture (Yao and Cooper, 1995);

The number of cells were determined and the amount of cells surviving in the presence of high-concentration of potassium was set at 100%. As can be seen approx. On FIG. 8 only 60% survived in the presence of brains-derived neurotrophic factor or basic fibroblast growth factor. When FGL was added in a sode-range of 2-250 microgram per ml statistically significant survival was observed up to 90% of the positive control at a dose of 250 microgram per ml of the monomeric form of the FGL peptide Example 6

FG Loop Fragments and Variants

Peptides derived from the FG-lops of the neural cell adhesion molecules L1 and NCAM (third F3-module of L1 and first F3 module of NCAM) were prepared in different lengths, see FIG. 9a, and their effect on neurite outgrowth from primary hippocampal neurons were tested adding the various peptides in a concentration of 25 microM. FIG. 9b. The NCAM peptides are referred to as FN3,1 and the L1 peptides are referred to as L1. The variants indicated in FIG. 9a are indicated by the number of amino acids in each peptide. As can be seen from the figure, the peptides had a stimulatory effect on neurite outgrowth reaching statistically significance for the nine amino acid variant of the Fgloop of first fibronectin type III module of NCAM and the nine amino acid variant of the FG-loop of the third fibronectin type III-module of L1.

REFERENCES

Banga, A. K. (Editor). Therapeutic peptides and protein formulation. Processing and delivery systems. Technomic Publishing AG, Basel, 1995.
Berezin, V., Bock, E. and Poulsen, F. M.: The neural cell adhesion molecule. Curr Opin Drug Disc Dev, 2000, 3:605-609.
Chan A W, Hutchinson E G, Harris D, Thornton J M. Identification, classification, and analysis of beta-bulges in proteins. Protein Sci 1993 October; 2(10): 1574-90
DeMello S. R., Borodezt K. and Soltoff S. P. (1997) Insulin-like growth factor and potassium depolarization maintain neuronal survival by distinct pathways: possible involvement of PI 3-kinase in IGF-1 signaling. J. Neurosci. 17:1548-1560.
Doherty P, Walsh F S. CAM-FGF Receptor Interactions: A Model for Axonal Growth Mol Cell Neurosci. 1996 2/3: 99-111.
Dzhandzhugazyan K, Bock E. Demonstration of (Ca(2+)-Mg2+)-ATPase activity of the neural cell adhesion molecule. FEBS Lett Dec. 27, 1993; 336(2):279-83
Dzhandzhugazyan K, Bock E. Demonstration of an extracellular ATP-binding site in NCAM: functional implications of nucleotide binding. Biochemistry Dec. 9, 1997; 36(49): 15381-95
Eilers A, Whitfield J, Babij C, Rubin L L, Ham J. Role of the Jun kinase pathway in the regulation of c-Jun expression and apoptosis in sympathetic neurons. J Neurosci. Mar. 1, 1998; 18(5):1713-24.
Eriksson A E, Cousens L S, Matthews B W. Refinement of the structure of human basic fibroblast growth factor at 1.6 Å resolution and analysis of presumed heparin binding sites by selenate substitution. Protein Sci 1993 August; 2(8): 1274-84
Furka A, Sebestyen F, Asgedom M, Dibo G. General method for rapid synthesis of multicomponent peptide mixtures. Int J Pept Protein Res. 1991 June; 37(6):487-93.
Hatten M E, Lynch M, Rydel R E, Sanchez J, Joseph-Silverstein J, Moscatelli D, Rifkin D B. In vitro neurite extension by granule neurons is dependent upon astroglial-derived fibroblast growth factor. Dev Biol 1988 February; 125(2): 280-9
Horstkorte R, Schachner M, Magyar J P, Vorherr T, Schmitz B. The fourth immunoglobulin-like domain of NCAM contains a carbohydrate recognition domain for oligomannosidic glycans implicated in association with L1 and neurite outgrowth. J Cell Biol. 1993 June; 121(6):1409-21.

Hulley P, Schachner M, Lubbert H. L1 neural cell adhesion molecule is a survival factor for fetal dopaminergic neurons. J Neurosci Res. Jul. 15, 1998; 53(2):129-34.

Jensen P H, Soroka V, Thomsen N K, Ralets I, Berezin V, Bock E, Poulsen F M. Structure and interactions of NCAM modules 1 and 2, basic elements in neural cell adhesion. Nat Struct Biol 1999 6:486-93

Kasper C, Rasmussen H, Kastrup J S, Ikemizu S, Jones E Y, Berezin V, Bock E, Larsen I K. Structural basis of cell-cell adhesion by NCAM. Nat Struct Biol 2000 May; 7(5):389-93

Kiselyov V V, Berezin V, Maar T E, Soroka V, Edvardsen K, Schousboe A, Bock E. The first immunoglobulin-like neural cell adhesion molecule (NCAM) domain is involved in double-reciprocal interaction with the second immunoglobulin-like NCAM domain and in heparin binding. J Biol Chem Apr. 11, 1997; 272(15):10125-34

Lam K S, Salmon S E, Hersh E M, Hruby V J, Kazmierski W M, Knapp R J. A new type of synthetic peptide library for identifying ligand-binding activity. Nature. 1991 354:82-84.

Ranheim T S, Edelman G M, Cunningham B A. Homophilic adhesion mediated by the neural cell adhesion molecule involves multiple immunoglobulin domains. Proc Natl Acad Sci U S A Apr. 30, 1996; 93(9):4071-5

Rao Y, Wu X F, Gariepy J, Rutishauser U, Siu C H. Identification of a peptide sequence involved in homophilic binding in the neural cell adhesion molecule NCAM. J Cell Biol 1992 August; 118(4):937-49

Rao Y, Zhao X, Siu C H. Mechanism of homophilic binding mediated by the neural cell adhesion molecule NCAM. Evidence for isologous interaction. J Biol Chem. Nov. 4, 1994; 269(44):27540-8.

Retzler C, Gohring W, Rauch U. Analysis of neurocan structures interacting with the neural cell adhesion molecule N-CAM. J Biol Chem. Nov. 1, 1996; 271(44):27304-10.

Ronn L C, Bock E, Linnemann D, Jahnsen H. NCAM-antibodies modulate induction of long-term potentiation in rat hippocampal CA1. Brain Res. Apr. 17, 1995; 677(1):145-51.

Ronn L C, Olsen M, Ostergaard S, Kiselyov V, Berezin V, Mortensen M T, Lerche M H, Jensen P H, Soroka V, Saffell J L, Doherty P, Poulsen F M, Bock E, Holm A, Saffells J L. Identification of a neuritogenic ligand of the neural cell adhesion molecule using a combinatorial library of synthetic peptides. Nat Biotechnol. 1999 October; 17(10):1000-5.

Ronn L C, Ralets I, Hartz B P, Bech M, Berezin A, Berezin V, Moller A, Bock E. A simple procedure for quantification of neurite outgrowth based on stereological principles. J Neurosci Methods. Jul. 31, 2000; 100(1-2):25-32.

Sibanda B L, Blundell T L, Thornton J M. Conformation of beta-hairpins in protein structures. A systematic classification with applications to modelling by homology, electron density fitting and protein engineering. J Mol Biol Apr. 20, 1989; 206(4):759-77

Skaper S D, Floreani M, Negro A, Facci L, Giusti P. Neurotrophins rescue cerebellar granule neurons from oxidative stress-mediated apoptotic death: selective involvement of phosphatidylinositol 3-kinase and the mitogen-activated protein kinase pathway. J Neurochem. 1998 May; 70(5):1859-68.

Skladchikova G, Ronn L C, Berezin V, Bock E. Extracellular adenosine triphosphate affects neural cell adhesion molecule (NCAM)-mediated cell adhesion and neurite outgrowth. J Neurosci Res Jul. 15, 1999; 57(2):207-18

Villalba M, Bockaert J, Journot L. Pituitary adenylate cyclase-activating polypeptide (PACAP-38) protects cerebellar granule neurons from apoptosis by activating the mitogen-activated protein kinase (MAP kinase) pathway. J Neurosci. Jan. 1, 1997; 17(1):83-90.

Wilmot C M, Thornton J M. Beta-turns and their distortions: a proposed new nomenclature. Protein Eng. 1990 May; 3(6):479-93.

Yao R, Cooper G M. Requirement for phosphatidylinositol-3 kinase in the prevention of apoptosis by nerve growth factor. Science. Mar. 31, 1995; 267(5206):2003-6.

The invention claimed is:

1. A compound which is
(I) a peptide consisting of 5 to 80 amino acid residues, said peptide comprising
  (i) (a) the putative FG loop (SEQ ID NO:1) of the second Fibronectin III (Fn3,2) module of the neural cell adhesion molecule (NCAM), or (b) a fragment at least five amino acids long thereof, or (c) a substitution variant of said FG loop wherein said variant is at least 75% identical to said Fn3,2 FG loop (i) (a), or
  (ii) (a) the putative FG loop (SEQ ID NO:31) of the first Fibronectin III (Fn3 µl) module of NCAM, or (b) a fragment at least five amino acids long thereof, or
  (iii) (a) the putative FG loop (SEQ ID NO:29) of the third Fibronection III (Fn3,3) module of L1, or (b) a fragment at least five amino acids long thereof, or (c) a substitution variant of said FG loop, wherein said variant is at least 75% identical to said FG loop (iii) (a), or
(II) an oligomeric peptide consisting essentially of two or more monomers, which may be the same or different, and which independently consist of an amino acid sequence satisfying that of a peptide according to (I), or
(III) a salt, ester or amide of the peptide of (I) or the oligomeric peptide of (II),
wherein said compound is not a peptide consisting of the amino acid sequence AENQQKS (SEQ ID NO:4), or a salt, ester or amide thereof,
said compound being in at least partially purified and soluble form and capable of binding to Fibroblast Growth Factor (FGF) receptor and capable of stimulating FGFR signaling.

2. The compound according to claim 1, comprising the sequence NGKGL (SEQ ID NO:26) or NGRGL (SEQ ID NO:27).

3. The compound according to claim 1, wherein said compound comprises a peptide sequence having the motif A-E-N-Q-X-X-K (SEQ ID NO:206), wherein X may be any amino acid residue.

4. The compound according to claim 3, wherein X is selected from Glutamine (Q), Alanine (A) and/or Asparagine (N) and/or Glycine (G).

5. The compound according to claim 1, wherein said compound comprises at least one peptide sequence selected from the group consisting of

EVYVVAENQQGKSKA, (SEQ ID NO 1)

EVAVVAENQQGASAA, (SEQ ID NO 2)

VAENQQGKS, (SEQ ID NO 3)

AENQQGK (SEQ ID NO 5)

EVQAFNGRGLGPPAS, (SEQ ID NO 29)

RLAALNGKGLGEIS, (SEQ ID NO 31)
and

LNGKG. (SEQ ID NO 36)

6. The compound according to claim 1, wherein the compound comprises the amino acid sequence AENQ-L4-G (SEQ ID NO:205) wherein L4 is a single amino acid residue.

7. The compound according to claim 1, wherein the compound is a dimer or a multimer, and thereby comprises a plurality of monomers.

8. The compound according to claim 7, wherein the monomers are identical to each other.

9. The compound according to claim 7, wherein the monomers are not identical to each other.

10. The compound according to claim 1, consisting of 10-80 amino acid residues.

11. The compound according to claim 1, consisting of 5-20 amino acid residues.

12. The compound of claim 1, wherein said sequence identity of at least 75% is at least 85%.

13. The compound of claim 12, wherein said substitution variants (c) of each of (i) and (iii) differ from their reference sequence (a) of (i) (and (iii), respectively, solely by one or more conservative substitutions.

14. The compound of claim 1, wherein said substitution variants (c) of each of (i) and (iii) differ from their reference sequence (a) of (i) or (iii), respectively, solely by one or more conservative substitutions.

15. The compound of claim 1, wherein said substitution variants (c) of each of (i) and (iii) differ from their reference sequence (a) of (i) or (iii), respectively, solely by one or more conservative substitutions, and/or by replacement of an L-amino acid with the corresponding D-amino acid.

16. The compound of claim 1 wherein the peptide of (I), and the corresponding monomer of the oligomeric peptide of (II), are each at least seven amino acid residues in length.

17. The compound of claim 16, wherein the peptide of (I) is or the monomers of the oligomeric peptide of (II) are peptides according to (i).

18. The compound of claim 1 wherein the peptide of (I), and the corresponding monomer of the oligomeric peptide of (II), are each at least ten amino acid residues in length.

19. The compound of claim 1, which is in pharmaceutically acceptable form.

20. A composition comprising at least one compound as defined in claim 19.

21. The composition according to claim 20, wherein the compounds are formulated as dimers.

22. The composition according to claim 20, wherein the compounds are formulated as multimers.

23. The composition according to claim 20 formulated for oral, percutaneous, intramuscular, intravenous, intracranial, intrathecal, intracerebroventricular, intranasal or pulmonal administration.

24. The compound of claim 1, wherein the compound is a compound according to (I), or an ester, salt or amide of a compound according to (I).

25. The compound of claim 24, said compound comprising SEQ ID NO:1.

26. The compound of claim 24, wherein the peptide of (I) is at least seven amino acid residues in length.

27. The compound of claim 24, wherein the peptide of (I) is at least ten amino acid residues in length.

28. The compound of claim 1, wherein the oligomeric peptide of (II) is a dendrimer.

29. The compound of claim 1, wherein the peptide of (I) consists of 5-20 residues.

30. The compound according to claim 1, wherein the FGF receptor is selected from the group consisting of FGF receptor I, FGF receptor II, FGF receptor III, and FGF receptor IV.

31. The compound of claim 30 in which the receptor is a human FGF receptor.

32. The compound of claim 30 in which the receptor is FGF receptor I.

33. The compound according to claim 30, wherein said compound comprises a peptide sequence having the motif A-E-N-Q-X-X-K (SEQ ID NO:206), wherein X may be any amino acid residue.

34. The compound of claim 30, wherein said sequence identity of at least 75% is at least 85%.

35. The compound of claim 34, wherein said substitution variants (c) of each of (i) and (iii) differ from their reference sequence (a) of (i) or (iii), respectively, solely by one or more conservative substitutions.

36. The compound according to claim 30, wherein said compound comprises the amino acid sequence AENQ-L4-G (SEQ ID NO:205)
wherein L4 is a single amino acid residue.

37. The compound of claim 1, wherein said peptide of (I) does not comprise SEQ ID NO:4.

38. The compound of claim 37, wherein the peptide of (I) is or the monomers of the oligomeric peptide of (II) are peptides according to (i).

39. The compound of claim 1, wherein said peptide of (I) does not comprise SEQ ID NO:4 or a substitution variant of SEQ ID NO:4 that is at least 75% identical to SEQ ID NO:4.

40. The compound of claim 1, wherein the peptide of (I) is or the monomers of the oligomeric peptide of (II) are peptides according to (i).

41. The compound of claim 1, wherein the peptide of (I) is or the monomers of the oligomeric peptide of (II) are peptides according to (ii).

42. The compound of claim 1, wherein the peptide of (I) is or the monomers of the oligomeric peptide of (II) are peptides according to (iii).

43. The compound of claim 1, wherein said peptide of (I) comprises (i) (a), (i)(b), (ii) (a), (ii) (b), (iii) (a) or (iii) (b).

44. The compound of claim 1, wherein said peptide of (I) comprises (i)(a), (i)(c), (ii) (a), (iii) (a), or (iii) (c).

45. The compound of claim 1, wherein the peptide of (I) is or the monomers of the oligomeric peptide of (II) are peptides selected from the group consisting of SEQ ID NOS: 1, 29, 31, 2, 3, and 5.

46. The compound of claim 1, wherein the peptide of (I) is and the monomers of the oligomeric peptide of (II) are each not more than 20 amino acid residues.

47. The compound of claim 1, which is not part of a peptide library.

48. The compound of claim 1, said compound comprising SEQ ID NO:1.

49. The compound of claim 1, said compound consisting of SEQ ID NO:1, or a salt, ester or amide thereof.

50. A process of producing a composition, comprising mixing an effective amount of one or more of the compounds according to claim 1, with one or more pharmaceutically acceptable additives or carriers.

51. A method of modulating an FGF receptor, in a cell, said FGF receptor selected from the group consisting of FGF receptor I, FGF receptor II, FGF receptor III and FGF receptor IV, which comprises introducing into said cell a modulatory amount of the compound of claim 30.

52. The method of claim 51, wherein the modulation is of a human FGF receptor in cells in a human.

53. The method of claim 51, wherein the human is suffering from a disease or condition of the central or peripheral nervous system.

54. The method of claim 51, wherein the human is suffering from a disease or condition of the gonads, the pancreas, or the kidney.

55. The method of claim 51, wherein the human is suffering from a wound.

56. The method of claim 51, wherein the human is suffering from cancer.

57. The method of claim 51, wherein the human is suffering from impaired or subnormal ability to learn, short term memory, or long term memory.

58. A compound which is
(I) a peptide consisting of
A)
(i)(a) the putative FG loop (SEQ ID NO:1) of the second Fibronectin III (Fn3,2) module of the neural cell adhesion molecule (NCAM), or (b) a fragment at least five amino acids long thereof, or (c) a substitution variant of said FG loop wherein said variant is at least 75% identical to said Fn3,2 FG loop (i)(a), or (d) a substitution variant of said fragment (i)(b) wherein said variant is at least 75% identical to said fragment, and/or
(ii) (a) the putative FG loop (SEQ ID NO:31) of the first Fibronectin III (Fn3,1) module of NCAM, or (b) a fragment at least five amino acids long thereof, or (c) a substitution variant of said FG loop, or said fragment, wherein said variant is at least 75% identical to said Fn3,1 FG loop (ii)(a), or (d) a substitution variant of said fragment (ii)(b) wherein said variant is at least 75% identical to said fragment,
(iii) (a) the putative FG loop (SEQ ID NO:29) of the third Fibronection III (Fn3,3) module of L1, or (b) a fragment at least five amino acids long thereof, or (c) a substitution variant of said FG loop, wherein said variant is at least 75% identical to said FG loop (iii) (a), or (d) a substitution variant of said fragment (iii)(c) wherein said variant is at least 75% identical to said fragment,
(iv) (a) the subsequence SEQ ID NO:7 of the putative FG loop of basic fibroblast growth factor (FGF), or (b) a fragment at least five amino acids long thereof, or (c) a substitution variant of said FG loop, wherein said variant is at least 75% identical to said subsequence (iv) (a), or (d) a substitution variant of said fragment (iv) (b) wherein said variant is at least 75% identical to said fragment, or B) amino acid residues in the range of 5 to 10 amino acid residues, wherein said compound is selected from the group consisting of:

| | |
|---|---|
| VAENQQGKS, | (SEQ ID NO 3) |
| AENQQGK, | (SEQ ID NO 5) |
| AENQAGK, | (SEQ ID NO 6) |
| AMKEDGR, | (SEQ ID NO 7) |
| ALNGKGLG, | (SEQ ID NO 8) |
| AFNGRGLG, | (SEQ ID NO 9) |
| LNGKGLG, | (SEQ ID NO 10) |
| LNGKGL, | (SEQ ID NO 11) |
| ALNGKG, | (SEQ ID NO 12) |
| LNGNALGE, | (SEQ ID NO 13) |
| LNGKALG, | (SEQ ID NO 14) |
| ALNGKAL, | (SEQ ID NO 15) |
| ALNLKGLGD, | (SEQ ID NO 16) |
| LNGKELG, | (SEQ ID NO 17) |
| LTGKGLAE, | (SEQ ID NO 18) |
| LKGKGLEE, | (SEQ ID NO 19) |
| LNSKGLVE, | (SEQ ID NO 20) |
| LNGKALVE, | (SEQ ID NO 21) |
| LAAKGLGE, | (SEQ ID NO 22) |
| LDGKGL, | (SEQ ID NO 23) |
| KGLGE, | (SEQ ID NO 24) |
| DGKSLGE, | (SEQ ID NO 25) |
| NGKGL, | (SEQ ID NO 26) |
| NGRGL, | (SEQ ID NO 27) |
| QAFNGRGLGP, | (SEQ ID NO 28) |
| AALNGKGLGE, | (SEQ ID NO 30) |
| ALNGKGAP, | (SEQ ID NO 32) |
| VALNGKGAPR, | (SEQ ID NO 33) |
| LNGRG, and | (SEQ ID NO 35) |
| LNGKG, or | (SEQ ID NO 36) |

(II) an oligomeric peptide consisting essentially of two or more monomers, which may be the same or different, and which independently consist of an amino acid sequence satisfying that of a peptide according to (I), or (III) a salt, ester or amide of the peptide of (I) or the oligomeric peptide of (II), wherein said compound is not a peptide consisting of the amino acid sequence AENQQKS (SEQ ID NO:4), or a salt, ester or amide thereof, said compound being in at least partially purified and soluble form and capable of binding to Fibroblast Growth Factor (FGF) receptor and capable of stimulating FGFR signaling.

59. The compound of claim 58 wherein the peptide of (I), and the corresponding monomer of the oligomeric peptide of (II), are each at least seven amino acid residues.

60. The compound of claim 58 wherein the peptide of (I), and the corresponding monomer of the oligomeric peptide of (II), are each at least ten amino acid residues.

* * * * *

SEQUENCE LISTING

```
<160> NUMBER OF SEQ ID NOS: 218

<210> SEQ ID NO 1
<211> LENGTH: 15
<212> TYPE: PRT
<213> ORGANISM: Homo sapiens

<400> SEQUENCE: 1

Glu Val Tyr Val Val Ala Glu Asn Gln Gln Gly Lys Ser Lys Ala
1               5                   10                  15

<210> SEQ ID NO 2
<211> LENGTH: 15
<212> TYPE: PRT
<213> ORGANISM: Homo sapiens

<400> SEQUENCE: 2

Glu Val Ala Val Val Ala Glu Asn Gln Gln Gly Ala Ser Ala Ala
1               5                   10                  15

<210> SEQ ID NO 3
<211> LENGTH: 9
<212> TYPE: PRT
<213> ORGANISM: Homo sapiens
```

-continued

<400> SEQUENCE: 3

Val Ala Glu Asn Gln Gln Gly Lys Ser
1               5

<210> SEQ ID NO 4
<211> LENGTH: 7
<212> TYPE: PRT
<213> ORGANISM: Homo sapiens

<400> SEQUENCE: 4

Ala Glu Asn Gln Gln Gly Lys
1               5

<210> SEQ ID NO 5
<211> LENGTH: 7
<212> TYPE: PRT
<213> ORGANISM: Homo sapiens

<400> SEQUENCE: 5

Ala Glu Asn Gln Ala Gly Lys
1               5

<210> SEQ ID NO 6
<211> LENGTH: 7
<212> TYPE: PRT
<213> ORGANISM: Homo sapiens

<400> SEQUENCE: 6

Ala Glu Asn Gln Ala Gly Lys
1               5

<210> SEQ ID NO 7
<211> LENGTH: 7
<212> TYPE: PRT
<213> ORGANISM: Homo sapiens

<400> SEQUENCE: 7

Ala Met Lys Glu Asp Gly Arg
1               5

<210> SEQ ID NO 8
<211> LENGTH: 8
<212> TYPE: PRT
<213> ORGANISM: Homo sapiens

<400> SEQUENCE: 8

Ala Leu Asn Gly Lys Gly Leu Gly
1               5

<210> SEQ ID NO 9
<211> LENGTH: 8
<212> TYPE: PRT
<213> ORGANISM: Homo sapiens

<400> SEQUENCE: 9

Ala Phe Asn Gly Arg Gly Leu Gly
1               5

<210> SEQ ID NO 10
<211> LENGTH: 7
<212> TYPE: PRT
<213> ORGANISM: Homo sapiens

<400> SEQUENCE: 10

Leu Asn Gly Lys Gly Leu Gly
1               5

<210> SEQ ID NO 11
<211> LENGTH: 6
<212> TYPE: PRT
<213> ORGANISM: Homo sapiens

<400> SEQUENCE: 11

Leu Asn Gly Lys Gly Leu
1               5

<210> SEQ ID NO 12
<211> LENGTH: 6
<212> TYPE: PRT
<213> ORGANISM: Homo sapiens

<400> SEQUENCE: 12

Ala Leu Asn Gly Lys Gly
1               5

<210> SEQ ID NO 13
<211> LENGTH: 8
<212> TYPE: PRT
<213> ORGANISM: Homo sapiens

<400> SEQUENCE: 13

Leu Asn Gly Asn Ala Leu Gly Glu
1               5

<210> SEQ ID NO 14
<211> LENGTH: 7
<212> TYPE: PRT
<213> ORGANISM: Homo sapiens

<400> SEQUENCE: 14

Leu Asn Gly Lys Ala Leu Gly
1               5

<210> SEQ ID NO 15
<211> LENGTH: 7
<212> TYPE: PRT
<213> ORGANISM: Homo sapiens

<400> SEQUENCE: 15

Ala Leu Asn Gly Lys Ala Leu
1               5

<210> SEQ ID NO 16
<211> LENGTH: 9
<212> TYPE: PRT
<213> ORGANISM: Homo sapiens

<400> SEQUENCE: 16

Ala Leu Asn Leu Lys Gly Leu Gly Asp
1               5

<210> SEQ ID NO 17
<211> LENGTH: 7
<212> TYPE: PRT
<213> ORGANISM: Homo sapiens

<400> SEQUENCE: 17

Leu Asn Gly Lys Glu Leu Gly
1               5

```
<210> SEQ ID NO 18
<211> LENGTH: 8
<212> TYPE: PRT
<213> ORGANISM: Homo sapiens

<400> SEQUENCE: 18

Leu Thr Gly Lys Gly Leu Ala Glu
1               5

<210> SEQ ID NO 19
<211> LENGTH: 8
<212> TYPE: PRT
<213> ORGANISM: Homo sapiens

<400> SEQUENCE: 19

Leu Lys Gly Lys Gly Leu Glu Glu
1               5

<210> SEQ ID NO 20
<211> LENGTH: 8
<212> TYPE: PRT
<213> ORGANISM: Homo sapiens

<400> SEQUENCE: 20

Leu Asn Ser Lys Gly Leu Val Glu
1               5

<210> SEQ ID NO 21
<211> LENGTH: 8
<212> TYPE: PRT
<213> ORGANISM: Homo sapiens

<400> SEQUENCE: 21

Leu Asn Gly Lys Ala Leu Val Glu
1               5

<210> SEQ ID NO 22
<211> LENGTH: 8
<212> TYPE: PRT
<213> ORGANISM: Homo sapiens

<400> SEQUENCE: 22

Leu Ala Ala Lys Gly Leu Gly Glu
1               5

<210> SEQ ID NO 23
<211> LENGTH: 6
<212> TYPE: PRT
<213> ORGANISM: Homo sapiens

<400> SEQUENCE: 23

Leu Asp Gly Lys Gly Leu
1               5

<210> SEQ ID NO 24
<211> LENGTH: 5
<212> TYPE: PRT
<213> ORGANISM: Homo sapiens

<400> SEQUENCE: 24

Lys Gly Leu Gly Glu
1               5

<210> SEQ ID NO 25
<211> LENGTH: 7
```

```
<212> TYPE: PRT
<213> ORGANISM: Homo sapiens

<400> SEQUENCE: 25

Asp Gly Lys Ser Leu Gly Glu
 1               5

<210> SEQ ID NO 26
<211> LENGTH: 5
<212> TYPE: PRT
<213> ORGANISM: Homo sapiens

<400> SEQUENCE: 26

Asn Gly Lys Gly Leu
 1               5

<210> SEQ ID NO 27
<211> LENGTH: 5
<212> TYPE: PRT
<213> ORGANISM: Homo sapiens

<400> SEQUENCE: 27

Asn Gly Arg Gly Leu
 1               5

<210> SEQ ID NO 28
<211> LENGTH: 10
<212> TYPE: PRT
<213> ORGANISM: Homo sapiens

<400> SEQUENCE: 28

Gln Ala Phe Asn Gly Arg Gly Leu Gly Pro
 1               5                  10

<210> SEQ ID NO 29
<211> LENGTH: 15
<212> TYPE: PRT
<213> ORGANISM: Homo sapiens

<400> SEQUENCE: 29

Glu Val Gln Ala Phe Asn Gly Arg Gly Leu Gly Pro Pro Ala Ser
 1               5                  10                  15

<210> SEQ ID NO 30
<211> LENGTH: 10
<212> TYPE: PRT
<213> ORGANISM: Homo sapiens

<400> SEQUENCE: 30

Ala Ala Leu Asn Gly Lys Gly Leu Gly Glu
 1               5                  10

<210> SEQ ID NO 31
<211> LENGTH: 14
<212> TYPE: PRT
<213> ORGANISM: Homo sapiens

<400> SEQUENCE: 31

Arg Leu Ala Ala Leu Asn Gly Lys Gly Leu Gly Glu Ile Ser
 1               5                  10

<210> SEQ ID NO 32
<211> LENGTH: 8
<212> TYPE: PRT
<213> ORGANISM: Homo sapiens
```

```
<400> SEQUENCE: 32

Ala Leu Asn Gly Lys Gly Ala Pro
1               5

<210> SEQ ID NO 33
<211> LENGTH: 10
<212> TYPE: PRT
<213> ORGANISM: Homo sapiens

<400> SEQUENCE: 33

Val Ala Leu Asn Gly Lys Gly Ala Pro Arg
1               5                   10

<210> SEQ ID NO 34
<211> LENGTH: 14
<212> TYPE: PRT
<213> ORGANISM: Homo sapiens

<400> SEQUENCE: 34

Met Tyr Val Ala Leu Asn Gly Lys Gly Ala Pro Arg Arg Gln
1               5                   10

<210> SEQ ID NO 35
<211> LENGTH: 5
<212> TYPE: PRT
<213> ORGANISM: Homo sapiens

<400> SEQUENCE: 35

Leu Asn Gly Arg Gly
1               5

<210> SEQ ID NO 36
<211> LENGTH: 5
<212> TYPE: PRT
<213> ORGANISM: Homo sapiens

<400> SEQUENCE: 36

Leu Asn Gly Lys Gly
1               5

<210> SEQ ID NO 37
<211> LENGTH: 15
<212> TYPE: PRT
<213> ORGANISM: Homo sapiens

<400> SEQUENCE: 37

Met Tyr Val Ala Leu Asn Gly Lys Gly Ala Pro Arg Arg Gly Gln
1               5                   10                  15

<210> SEQ ID NO 38
<211> LENGTH: 15
<212> TYPE: PRT
<213> ORGANISM: Homo sapiens

<400> SEQUENCE: 38

Met Phe Leu Ala Leu Asp Arg Arg Gly Gly Pro Arg Pro Gly Gly
1               5                   10                  15

<210> SEQ ID NO 39
<211> LENGTH: 15
<212> TYPE: PRT
<213> ORGANISM: Homo sapiens

<400> SEQUENCE: 39

Met Phe Leu Ala Leu Asp Ser Gln Gly Ile Pro Arg Gln Gly Gln
```

<210> SEQ ID NO 40
<211> LENGTH: 14
<212> TYPE: PRT
<213> ORGANISM: Homo sapiens

<400> SEQUENCE: 40

Met Phe Val Ala Leu Asn Gln Lys Gly Ile Pro Val Arg Gly
1               5                   10

<210> SEQ ID NO 41
<211> LENGTH: 14
<212> TYPE: PRT
<213> ORGANISM: Homo sapiens

<400> SEQUENCE: 41

Met Phe Val Ala Leu Asn Gln Lys Gly Ile Pro Val Lys Gly
1               5                   10

<210> SEQ ID NO 42
<211> LENGTH: 14
<212> TYPE: PRT
<213> ORGANISM: Homo sapiens

<400> SEQUENCE: 42

Met Phe Val Ala Leu Asn Gln Lys Gly Leu Pro Val Lys Gly
1               5                   10

<210> SEQ ID NO 43
<211> LENGTH: 14
<212> TYPE: PRT
<213> ORGANISM: Homo sapiens

<400> SEQUENCE: 43

Trp Tyr Val Ser Val Asn Gly Lys Gly Arg Pro Arg Arg Gly
1               5                   10

<210> SEQ ID NO 44
<211> LENGTH: 14
<212> TYPE: PRT
<213> ORGANISM: Homo sapiens

<400> SEQUENCE: 44

Tyr Tyr Val Ala Leu Asn Lys Asp Gly Thr Pro Arg Glu Gly
1               5                   10

<210> SEQ ID NO 45
<211> LENGTH: 14
<212> TYPE: PRT
<213> ORGANISM: Homo sapiens

<400> SEQUENCE: 45

Tyr Tyr Val Ala Leu Asn Lys Asp Gly Ser Pro Arg Glu Gly
1               5                   10

<210> SEQ ID NO 46
<211> LENGTH: 14
<212> TYPE: PRT
<213> ORGANISM: Homo sapiens

<400> SEQUENCE: 46

Tyr Phe Val Ala Leu Asn Lys Asp Gly Thr Pro Arg Asp Gly
1               5                   10

```
<210> SEQ ID NO 47
<211> LENGTH: 14
<212> TYPE: PRT
<213> ORGANISM: Homo sapiens

<400> SEQUENCE: 47

Trp Tyr Val Ala Leu Asn Lys Arg Gly Lys Ala Lys Arg Gly
1               5                   10

<210> SEQ ID NO 48
<211> LENGTH: 14
<212> TYPE: PRT
<213> ORGANISM: Homo sapiens

<400> SEQUENCE: 48

Trp Tyr Leu Gly Leu Asn Lys Glu Gly Glu Ile Met Lys Gly
1               5                   10

<210> SEQ ID NO 49
<211> LENGTH: 14
<212> TYPE: PRT
<213> ORGANISM: Homo sapiens

<400> SEQUENCE: 49

Trp Phe Leu Gly Leu Asn Lys Glu Gly Gln Ile Met Lys Gly
1               5                   10

<210> SEQ ID NO 50
<211> LENGTH: 14
<212> TYPE: PRT
<213> ORGANISM: Homo sapiens

<400> SEQUENCE: 50

Thr Tyr Ile Ala Leu Ser Lys Tyr Gly Arg Val Lys Arg Gly
1               5                   10

<210> SEQ ID NO 51
<211> LENGTH: 14
<212> TYPE: PRT
<213> ORGANISM: Homo sapiens

<400> SEQUENCE: 51

Trp Phe Leu Gly Leu Asn Lys Glu Gly Gln Ala Met Lys Gly
1               5                   10

<210> SEQ ID NO 52
<211> LENGTH: 14
<212> TYPE: PRT
<213> ORGANISM: Homo sapiens

<400> SEQUENCE: 52

Trp Phe Leu Gly Leu Asn Lys Glu Gly Gln Val Met Lys Gly
1               5                   10

<210> SEQ ID NO 53
<211> LENGTH: 14
<212> TYPE: PRT
<213> ORGANISM: Homo sapiens

<400> SEQUENCE: 53

Trp Tyr Leu Gly Leu Asp Lys Glu Gly Gln Val Met Lys Gly
1               5                   10

<210> SEQ ID NO 54
<211> LENGTH: 14
<212> TYPE: PRT
```

<213> ORGANISM: Homo sapiens

<400> SEQUENCE: 54

Trp Tyr Leu Gly Leu Asp Lys Glu Gly Arg Val Met Lys Gly
1               5                   10

<210> SEQ ID NO 55
<211> LENGTH: 14
<212> TYPE: PRT
<213> ORGANISM: Homo sapiens

<400> SEQUENCE: 55

Trp Tyr Val Ala Leu Lys Arg Thr Gly Gln Tyr Lys Leu Gly
1               5                   10

<210> SEQ ID NO 56
<211> LENGTH: 14
<212> TYPE: PRT
<213> ORGANISM: Homo sapiens

<400> SEQUENCE: 56

Trp Phe Val Gly Leu Lys Lys Asn Gly Ser Cys Lys Arg Gly
1               5                   10

<210> SEQ ID NO 57
<211> LENGTH: 16
<212> TYPE: PRT
<213> ORGANISM: Homo sapiens

<400> SEQUENCE: 57

Ala Asn Arg Tyr Leu Ala Met Lys Glu Asp Gly Arg Leu Leu Ala Ser
1               5                   10                  15

<210> SEQ ID NO 58
<211> LENGTH: 16
<212> TYPE: PRT
<213> ORGANISM: Homo sapiens

<400> SEQUENCE: 58

Thr Gly Gln Tyr Leu Ala Met Asp Thr Glu Gly Leu Leu Tyr Gly Ser
1               5                   10                  15

<210> SEQ ID NO 59
<211> LENGTH: 16
<212> TYPE: PRT
<213> ORGANISM: Homo sapiens

<400> SEQUENCE: 59

Thr Gly Gln Tyr Leu Ala Met Asp Thr Asp Gly Leu Leu Tyr Gly Ser
1               5                   10                  15

<210> SEQ ID NO 60
<211> LENGTH: 16
<212> TYPE: PRT
<213> ORGANISM: Homo sapiens

<400> SEQUENCE: 60

Thr Gly Gln Tyr Leu Ala Met Asp Thr Ser Gly Leu Leu Tyr Gly Ser
1               5                   10                  15

<210> SEQ ID NO 61
<211> LENGTH: 16
<212> TYPE: PRT
<213> ORGANISM: Homo sapiens

<400> SEQUENCE: 61

```
Thr Gly Gln Phe Leu Ala Met Asp Thr Asp Gly Leu Leu Tyr Gly Ser
1               5                   10                  15
```

<210> SEQ ID NO 62
<211> LENGTH: 16
<212> TYPE: PRT
<213> ORGANISM: Homo sapiens

<400> SEQUENCE: 62

```
Ser Arg Phe Phe Val Ala Met Ser Ser Lys Gly Lys Leu Tyr Gly Ser
1               5                   10                  15
```

<210> SEQ ID NO 63
<211> LENGTH: 16
<212> TYPE: PRT
<213> ORGANISM: Homo sapiens

<400> SEQUENCE: 63

```
Ser Arg Phe Phe Val Ala Met Ser Ser Arg Gly Lys Leu Phe Gly Val
1               5                   10                  15
```

<210> SEQ ID NO 64
<211> LENGTH: 16
<212> TYPE: PRT
<213> ORGANISM: Homo sapiens

<400> SEQUENCE: 64

```
Ser Arg Phe Phe Val Ala Met Ser Ser Arg Gly Arg Leu Tyr Gly Ser
1               5                   10                  15
```

<210> SEQ ID NO 65
<211> LENGTH: 16
<212> TYPE: PRT
<213> ORGANISM: Homo sapiens

<400> SEQUENCE: 65

```
Ser Gly Leu Phe Val Ala Met Asn Ser Lys Gly Lys Leu Tyr Gly Ser
1               5                   10                  15
```

<210> SEQ ID NO 66
<211> LENGTH: 16
<212> TYPE: PRT
<213> ORGANISM: Homo sapiens

<400> SEQUENCE: 66

```
Ser Asn Lys Phe Leu Ala Met Ser Lys Lys Gly Lys Leu His Ala Ser
1               5                   10                  15
```

<210> SEQ ID NO 67
<211> LENGTH: 16
<212> TYPE: PRT
<213> ORGANISM: Homo sapiens

<400> SEQUENCE: 67

```
Ser Ala Leu Phe Val Ala Met Asn Ser Lys Gly Arg Leu Tyr Ala Thr
1               5                   10                  15
```

<210> SEQ ID NO 68
<211> LENGTH: 16
<212> TYPE: PRT
<213> ORGANISM: Homo sapiens

<400> SEQUENCE: 68

```
Ser Ala Leu Phe Ile Ala Met Asn Ser Lys Gly Arg Leu Tyr Thr Thr
1               5                   10                  15
```

```
<210> SEQ ID NO 69
<211> LENGTH: 16
<212> TYPE: PRT
<213> ORGANISM: Homo sapiens

<400> SEQUENCE: 69

Ser Gly Arg Tyr Leu Ala Met Asn Lys Arg Gly Arg Leu Tyr Ala Ser
1               5                   10                  15

<210> SEQ ID NO 70
<211> LENGTH: 16
<212> TYPE: PRT
<213> ORGANISM: Homo sapiens

<400> SEQUENCE: 70

Ser Glu Tyr Tyr Leu Ala Met Asn Lys Glu Gly Lys Leu Tyr Ala Lys
1               5                   10                  15

<210> SEQ ID NO 71
<211> LENGTH: 15
<212> TYPE: PRT
<213> ORGANISM: Homo sapiens

<400> SEQUENCE: 71

Ser Glu Tyr Tyr Leu Ala Met Asn Lys Gln Gly Leu Tyr Ala Lys
1               5                   10                  15

<210> SEQ ID NO 72
<211> LENGTH: 16
<212> TYPE: PRT
<213> ORGANISM: Homo sapiens

<400> SEQUENCE: 72

Ser Glu Phe Tyr Leu Ala Met Asn Lys Glu Gly Lys Leu Tyr Ala Lys
1               5                   10                  15

<210> SEQ ID NO 73
<211> LENGTH: 16
<212> TYPE: PRT
<213> ORGANISM: Homo sapiens

<400> SEQUENCE: 73

Ser Gly Leu Tyr Leu Gly Met Asn Glu Lys Gly Glu Leu Tyr Gly Ser
1               5                   10                  15

<210> SEQ ID NO 74
<211> LENGTH: 16
<212> TYPE: PRT
<213> ORGANISM: Homo sapiens

<400> SEQUENCE: 74

Ser Gly Leu Tyr Leu Gly Met Asn Asp Lys Gly Glu Leu Tyr Gly Ser
1               5                   10                  15

<210> SEQ ID NO 75
<211> LENGTH: 16
<212> TYPE: PRT
<213> ORGANISM: Homo sapiens

<400> SEQUENCE: 75

Ser Gly Leu Tyr Leu Gly Met Asn Glu Arg Gly Glu Leu Tyr Gly Ser
1               5                   10                  15

<210> SEQ ID NO 76
```

```
-continued

<211> LENGTH: 16
<212> TYPE: PRT
<213> ORGANISM: Homo sapiens

<400> SEQUENCE: 76

Ser Gly Leu Tyr Leu Gly Met Asn Glu Arg Gly Glu Leu Phe Gly Ser
1               5                   10                  15

<210> SEQ ID NO 77
<211> LENGTH: 16
<212> TYPE: PRT
<213> ORGANISM: Homo sapiens

<400> SEQUENCE: 77

Ser Asn Tyr Tyr Leu Ala Met Asn Lys Lys Gly Lys Leu Tyr Gly Ser
1               5                   10                  15

<210> SEQ ID NO 78
<211> LENGTH: 16
<212> TYPE: PRT
<213> ORGANISM: Homo sapiens

<400> SEQUENCE: 78

Ser Gly Phe Tyr Val Ala Met Asn Arg Arg Gly Arg Leu Tyr Gly Ser
1               5                   10                  15

<210> SEQ ID NO 79
<211> LENGTH: 16
<212> TYPE: PRT
<213> ORGANISM: Homo sapiens

<400> SEQUENCE: 79

Thr Gly Leu Tyr Ile Ala Met Asn Gly Glu Gly Tyr Leu Tyr Pro Ser
1               5                   10                  15

<210> SEQ ID NO 80
<211> LENGTH: 16
<212> TYPE: PRT
<213> ORGANISM: Homo sapiens

<400> SEQUENCE: 80

Ala Ser Leu Tyr Val Ala Met Asn Gly Glu Gly Tyr Leu Tyr Ser Ser
1               5                   10                  15

<210> SEQ ID NO 81
<211> LENGTH: 16
<212> TYPE: PRT
<213> ORGANISM: Homo sapiens

<400> SEQUENCE: 81

Thr Lys Leu Tyr Leu Ala Met Asn Ser Glu Gly Tyr Leu Tyr Thr Ser
1               5                   10                  15

<210> SEQ ID NO 82
<211> LENGTH: 17
<212> TYPE: PRT
<213> ORGANISM: Homo sapiens

<400> SEQUENCE: 82

Thr Gly Leu Tyr Ile Cys Met Asn Lys Lys Gly Lys Leu Ile Ala Lys
1               5                   10                  15

Ser

<210> SEQ ID NO 83
<211> LENGTH: 16
```

```
<212> TYPE: PRT
<213> ORGANISM: Homo sapiens

<400> SEQUENCE: 83

Leu Gly His Tyr Met Ala Met Asn Ala Glu Gly Leu Leu Tyr Ser Ser
1               5                   10                  15

<210> SEQ ID NO 84
<211> LENGTH: 16
<212> TYPE: PRT
<213> ORGANISM: Homo sapiens

<400> SEQUENCE: 84

Thr Glu Phe Tyr Leu Cys Met Asn Arg Lys Gly Lys Leu Val Gly Lys
1               5                   10                  15

<210> SEQ ID NO 85
<211> LENGTH: 16
<212> TYPE: PRT
<213> ORGANISM: Homo sapiens

<400> SEQUENCE: 85

Ser Val Arg Tyr Leu Cys Met Gly Ala Asp Gly Lys Met Gln Gly Leu
1               5                   10                  15

<210> SEQ ID NO 86
<211> LENGTH: 14
<212> TYPE: PRT
<213> ORGANISM: Homo sapiens

<400> SEQUENCE: 86

Trp Phe Val Gly Leu Lys Lys Asn Gly Ser Cys Lys Arg Gly
1               5                   10

<210> SEQ ID NO 87
<211> LENGTH: 14
<212> TYPE: PRT
<213> ORGANISM: Homo sapiens

<400> SEQUENCE: 87

Trp Tyr Val Ala Leu Lys Arg Thr Gly Gln Tyr Lys Leu Gly
1               5                   10

<210> SEQ ID NO 88
<211> LENGTH: 14
<212> TYPE: PRT
<213> ORGANISM: Homo sapiens

<400> SEQUENCE: 88

Trp Tyr Val Ser Val Asn Gly Lys Gly Arg Pro Arg Arg Gly
1               5                   10

<210> SEQ ID NO 89
<211> LENGTH: 15
<212> TYPE: PRT
<213> ORGANISM: Homo sapiens

<400> SEQUENCE: 89

Gly Met Phe Ile Ala Leu Ser Lys Asn Gly Lys Thr Lys Lys Gly
1               5                   10                  15

<210> SEQ ID NO 90
<211> LENGTH: 15
<212> TYPE: PRT
<213> ORGANISM: Mus musculus
```

```
<400> SEQUENCE: 90

Gly Met Phe Met Ala Leu Ser Lys Asn Gly Arg Thr Lys Lys Gly
1               5                   10                  15

<210> SEQ ID NO 91
<211> LENGTH: 15
<212> TYPE: PRT
<213> ORGANISM: Bos taurus

<400> SEQUENCE: 91

Gly Met Phe Ile Ala Leu Ser Lys Asn Gly Lys Ala Lys Lys Gly
1               5                   10                  15

<210> SEQ ID NO 92
<211> LENGTH: 14
<212> TYPE: PRT
<213> ORGANISM: Homo sapiens

<400> SEQUENCE: 92

Trp Tyr Val Ala Leu Asn Lys Arg Gly Lys Ala Lys Arg Gly
1               5                   10

<210> SEQ ID NO 93
<211> LENGTH: 14
<212> TYPE: PRT
<213> ORGANISM: Homo sapiens

<400> SEQUENCE: 93

Thr Tyr Ile Ala Leu Ser Lys Tyr Gly Arg Val Lys Arg Gly
1               5                   10

<210> SEQ ID NO 94
<211> LENGTH: 14
<212> TYPE: PRT
<213> ORGANISM: Homo sapiens

<400> SEQUENCE: 94

Met Phe Val Ala Leu Asn Gln Lys Gly Ile Pro Val Arg Gly
1               5                   10

<210> SEQ ID NO 95
<211> LENGTH: 14
<212> TYPE: PRT
<213> ORGANISM: Mus musculus

<400> SEQUENCE: 95

Met Phe Val Ala Leu Asn Gln Lys Gly Ile Pro Val Lys Gly
1               5                   10

<210> SEQ ID NO 96
<211> LENGTH: 14
<212> TYPE: PRT
<213> ORGANISM: Rattus spp.

<400> SEQUENCE: 96

Met Phe Val Ala Leu Asn Gln Lys Gly Leu Pro Val Lys Gly
1               5                   10

<210> SEQ ID NO 97
<211> LENGTH: 14
<212> TYPE: PRT
<213> ORGANISM: Homo sapiens

<400> SEQUENCE: 97

Trp Tyr Met Ala Phe Thr Arg Lys Gly Arg Pro Arg Lys Gly
```

```
<210> SEQ ID NO 98
<211> LENGTH: 14
<212> TYPE: PRT
<213> ORGANISM: Homo sapiens

<400> SEQUENCE: 98

Tyr Tyr Val Ala Leu Asn Lys Asp Gly Thr Pro Arg Glu Gly
1               5                   10

<210> SEQ ID NO 99
<211> LENGTH: 15
<212> TYPE: PRT
<213> ORGANISM: Homo sapiens

<400> SEQUENCE: 99

Met Tyr Val Ala Leu Asn Gly Lys Gly Ala Pro Arg Arg Gly Gln
1               5                   10                  15

<210> SEQ ID NO 100
<211> LENGTH: 14
<212> TYPE: PRT
<213> ORGANISM: Homo sapiens

<400> SEQUENCE: 100

Trp Tyr Leu Gly Leu Asp Lys Glu Gly Gln Val Met Lys Gly
1               5                   10

<210> SEQ ID NO 101
<211> LENGTH: 14
<212> TYPE: PRT
<213> ORGANISM: Mus musculus

<400> SEQUENCE: 101

Trp Tyr Leu Gly Leu Asp Lys Glu Gly Arg Val Met Lys Gly
1               5                   10

<210> SEQ ID NO 102
<211> LENGTH: 14
<212> TYPE: PRT
<213> ORGANISM: Homo sapiens

<400> SEQUENCE: 102

Trp Phe Leu Gly Leu Asn Lys Glu Gly Gln Ile Met Lys Gly
1               5                   10

<210> SEQ ID NO 103
<211> LENGTH: 14
<212> TYPE: PRT
<213> ORGANISM: Homo sapiens

<400> SEQUENCE: 103

Trp Tyr Leu Gly Leu Asn Lys Glu Gly Glu Ile Met Lys Gly
1               5                   10

<210> SEQ ID NO 104
<211> LENGTH: 14
<212> TYPE: PRT
<213> ORGANISM: Homo sapiens

<400> SEQUENCE: 104

Trp Phe Leu Gly Leu Asn Lys Glu Gly Gln Ala Met Lys Gly
1               5                   10
```

```
<210> SEQ ID NO 105
<211> LENGTH: 14
<212> TYPE: PRT
<213> ORGANISM: Mus musculus

<400> SEQUENCE: 105

Trp Phe Leu Gly Leu Asn Lys Glu Gly Gln Val Met Lys Gly
1               5                   10

<210> SEQ ID NO 106
<211> LENGTH: 14
<212> TYPE: PRT
<213> ORGANISM: Homo sapiens

<400> SEQUENCE: 106

Tyr Tyr Val Ala Leu Asn Lys Asp Gly Ser Pro Arg Glu Gly
1               5                   10

<210> SEQ ID NO 107
<211> LENGTH: 13
<212> TYPE: PRT
<213> ORGANISM: Homo sapiens

<400> SEQUENCE: 107

Trp Phe Met Ala Phe Thr Arg Gln Gly Arg Pro Arg Gln
1               5                   10

<210> SEQ ID NO 108
<211> LENGTH: 14
<212> TYPE: PRT
<213> ORGANISM: Homo sapiens

<400> SEQUENCE: 108

Trp Phe Val Gly Leu Lys Lys Asn Gly Ser Cys Lys Arg Gly
1               5                   10

<210> SEQ ID NO 109
<211> LENGTH: 14
<212> TYPE: PRT
<213> ORGANISM: Mus musculus

<400> SEQUENCE: 109

Trp Tyr Val Gly Phe Thr Lys Lys Gly Arg Pro Arg Lys Gly
1               5                   10

<210> SEQ ID NO 110
<211> LENGTH: 14
<212> TYPE: PRT
<213> ORGANISM: Homo sapiens

<400> SEQUENCE: 110

Tyr Phe Val Ala Leu Asn Lys Asp Gly Thr Pro Arg Asp Gly
1               5                   10

<210> SEQ ID NO 111
<211> LENGTH: 15
<212> TYPE: PRT
<213> ORGANISM: Homo sapiens

<400> SEQUENCE: 111

Met Phe Leu Ala Leu Asp Arg Arg Gly Gly Pro Arg Pro Gly Gly
1               5                   10                  15

<210> SEQ ID NO 112
<211> LENGTH: 15
<212> TYPE: PRT
```

<213> ORGANISM: Mus musculus

<400> SEQUENCE: 112

Met Phe Leu Ala Leu Asp Ser Gln Gly Ile Pro Arg Gln Gly Gln
1               5                   10                  15

<210> SEQ ID NO 113
<211> LENGTH: 16
<212> TYPE: PRT
<213> ORGANISM: Mus musculus

<400> SEQUENCE: 113

Thr Gly Gln Tyr Leu Ala Met Asp Thr Glu Gly Leu Leu Tyr Gly Ser
1               5                   10                  15

<210> SEQ ID NO 114
<211> LENGTH: 16
<212> TYPE: PRT
<213> ORGANISM: Homo sapiens

<400> SEQUENCE: 114

Thr Gly Gln Tyr Leu Ala Met Asp Thr Asp Gly Leu Leu Tyr Gly Ser
1               5                   10                  15

<210> SEQ ID NO 115
<211> LENGTH: 16
<212> TYPE: PRT
<213> ORGANISM: Sus scrofa

<400> SEQUENCE: 115

Thr Gly Gln Tyr Leu Ala Met Asp Thr Ser Gly Leu Leu Tyr Gly Ser
1               5                   10                  15

<210> SEQ ID NO 116
<211> LENGTH: 16
<212> TYPE: PRT
<213> ORGANISM: Bos taurus

<400> SEQUENCE: 116

Thr Gly Gln Phe Leu Ala Met Asp Thr Asp Gly Leu Leu Tyr Gly Ser
1               5                   10                  15

<210> SEQ ID NO 117
<211> LENGTH: 16
<212> TYPE: PRT
<213> ORGANISM: Homo sapiens

<400> SEQUENCE: 117

Ala Asn Arg Tyr Leu Ala Met Lys Glu Asp Gly Arg Leu Leu Ala Ser
1               5                   10                  15

<210> SEQ ID NO 118
<211> LENGTH: 16
<212> TYPE: PRT
<213> ORGANISM: Homo sapiens

<400> SEQUENCE: 118

Ser Gly Arg Tyr Leu Ala Met Asn Lys Arg Gly Arg Leu Tyr Ala Ser
1               5                   10                  15

<210> SEQ ID NO 119
<211> LENGTH: 16
<212> TYPE: PRT
<213> ORGANISM: Mus musculus

<400> SEQUENCE: 119

```
Ser Arg Phe Phe Val Ala Met Ser Ser Lys Gly Lys Leu Tyr Gly Ser
1               5                   10                  15
```

<210> SEQ ID NO 120
<211> LENGTH: 16
<212> TYPE: PRT
<213> ORGANISM: Mus musculus

<400> SEQUENCE: 120

```
Ser Arg Phe Phe Val Ala Met Ser Ser Arg Gly Lys Leu Phe Gly Val
1               5                   10                  15
```

<210> SEQ ID NO 121
<211> LENGTH: 16
<212> TYPE: PRT
<213> ORGANISM: Bos taurus

<400> SEQUENCE: 121

```
Ser Arg Phe Phe Val Ala Met Ser Ser Arg Gly Arg Leu Tyr Gly Ser
1               5                   10                  15
```

<210> SEQ ID NO 122
<211> LENGTH: 16
<212> TYPE: PRT
<213> ORGANISM: Gallus gallus

<400> SEQUENCE: 122

```
Ser Gly Leu Phe Val Ala Met Asn Ser Lys Gly Lys Leu Tyr Gly Ser
1               5                   10                  15
```

<210> SEQ ID NO 123
<211> LENGTH: 16
<212> TYPE: PRT
<213> ORGANISM: Homo sapiens

<400> SEQUENCE: 123

```
Ser Asn Lys Phe Leu Ala Met Ser Lys Gly Lys Leu His Ala Ser
1               5                   10                  15
```

<210> SEQ ID NO 124
<211> LENGTH: 16
<212> TYPE: PRT
<213> ORGANISM: Homo sapiens

<400> SEQUENCE: 124

```
Ser Ala Leu Phe Val Ala Met Asn Ser Lys Gly Arg Leu Tyr Ala Thr
1               5                   10                  15
```

<210> SEQ ID NO 125
<211> LENGTH: 16
<212> TYPE: PRT
<213> ORGANISM: Mus musculus

<400> SEQUENCE: 125

```
Ser Ala Leu Phe Ile Ala Met Asn Ser Lys Gly Arg Leu Tyr Thr Thr
1               5                   10                  15
```

<210> SEQ ID NO 126
<211> LENGTH: 16
<212> TYPE: PRT
<213> ORGANISM: Homo sapiens

<400> SEQUENCE: 126

```
Ser Glu Tyr Tyr Leu Ala Met Asn Lys Glu Gly Lys Leu Tyr Ala Lys
1               5                   10                  15
```

```
<210> SEQ ID NO 127
<211> LENGTH: 15
<212> TYPE: PRT
<213> ORGANISM: Homo sapiens

<400> SEQUENCE: 127

Ser Glu Tyr Tyr Leu Ala Met Asn Lys Gln Gly Leu Tyr Ala Lys
1               5                   10                  15

<210> SEQ ID NO 128
<211> LENGTH: 16
<212> TYPE: PRT
<213> ORGANISM: Rattus spp.

<400> SEQUENCE: 128

Ser Glu Phe Tyr Leu Ala Met Asn Lys Glu Gly Lys Leu Tyr Ala Lys
1               5                   10                  15

<210> SEQ ID NO 129
<211> LENGTH: 17
<212> TYPE: PRT
<213> ORGANISM: Homo sapiens

<400> SEQUENCE: 129

Thr Gly Leu Tyr Ile Cys Met Asn Lys Lys Gly Lys Leu Ile Ala Lys
1               5                   10                  15
Ser

<210> SEQ ID NO 130
<211> LENGTH: 16
<212> TYPE: PRT
<213> ORGANISM: Homo sapiens

<400> SEQUENCE: 130

Ser Gly Leu Tyr Leu Gly Met Asn Glu Lys Gly Glu Leu Tyr Gly Ser
1               5                   10                  15

<210> SEQ ID NO 131
<211> LENGTH: 16
<212> TYPE: PRT
<213> ORGANISM: Homo sapiens

<400> SEQUENCE: 131

Ser Asn Tyr Tyr Leu Ala Met Asn Lys Lys Gly Lys Leu Tyr Gly Ser
1               5                   10                  15

<210> SEQ ID NO 132
<211> LENGTH: 16
<212> TYPE: PRT
<213> ORGANISM: Homo sapiens

<400> SEQUENCE: 132

Leu Gly His Tyr Met Ala Met Asn Ala Glu Gly Leu Leu Tyr Ser Ser
1               5                   10                  15

<210> SEQ ID NO 133
<211> LENGTH: 16
<212> TYPE: PRT
<213> ORGANISM: Homo sapiens

<400> SEQUENCE: 133

Ala Ser Leu Tyr Val Ala Met Asn Gly Glu Gly Tyr Leu Tyr Ser Ser
1               5                   10                  15
```

```
<210> SEQ ID NO 134
<211> LENGTH: 16
<212> TYPE: PRT
<213> ORGANISM: Homo sapiens

<400> SEQUENCE: 134

Thr Lys Leu Tyr Leu Ala Met Asn Ser Glu Gly Tyr Leu Tyr Thr Ser
1               5                   10                  15

<210> SEQ ID NO 135
<211> LENGTH: 16
<212> TYPE: PRT
<213> ORGANISM: Homo sapiens

<400> SEQUENCE: 135

Thr Gly Leu Tyr Ile Ala Met Asn Gly Glu Gly Tyr Leu Tyr Pro Ser
1               5                   10                  15

<210> SEQ ID NO 136
<211> LENGTH: 15
<212> TYPE: PRT
<213> ORGANISM: Mus musculus

<400> SEQUENCE: 136

Ser Val Arg Tyr Leu Cys Met Ser Ala Asp Gly Lys Ile Tyr Gly
1               5                   10                  15

<210> SEQ ID NO 137
<211> LENGTH: 16
<212> TYPE: PRT
<213> ORGANISM: Homo sapiens

<400> SEQUENCE: 137

Ser Gly Leu Tyr Leu Gly Met Asn Glu Arg Gly Glu Leu Tyr Gly Ser
1               5                   10                  15

<210> SEQ ID NO 138
<211> LENGTH: 16
<212> TYPE: PRT
<213> ORGANISM: Rattus spp.

<400> SEQUENCE: 138

Ser Gly Leu Tyr Leu Gly Met Asn Glu Arg Gly Glu Leu Phe Gly Ser
1               5                   10                  15

<210> SEQ ID NO 139
<211> LENGTH: 15
<212> TYPE: PRT
<213> ORGANISM: Homo sapiens

<400> SEQUENCE: 139

Ser Glu Lys Tyr Ile Cys Met Asn Lys Arg Gly Lys Leu Ile Gly
1               5                   10                  15

<210> SEQ ID NO 140
<211> LENGTH: 16
<212> TYPE: PRT
<213> ORGANISM: Homo sapiens

<400> SEQUENCE: 140

Thr Glu Phe Tyr Leu Cys Met Asn Arg Lys Gly Lys Leu Val Gly Lys
1               5                   10                  15

<210> SEQ ID NO 141
<211> LENGTH: 16
```

```
<212> TYPE: PRT
<213> ORGANISM: Homo sapiens

<400> SEQUENCE: 141

Ser Val Arg Tyr Leu Cys Met Gly Ala Asp Gly Lys Met Gln Gly Leu
1               5                   10                  15

<210> SEQ ID NO 142
<211> LENGTH: 16
<212> TYPE: PRT
<213> ORGANISM: Homo sapiens

<400> SEQUENCE: 142

Ser Gly Leu Tyr Leu Gly Met Asn Asp Lys Gly Glu Leu Tyr Gly Ser
1               5                   10                  15

<210> SEQ ID NO 143
<211> LENGTH: 15
<212> TYPE: PRT
<213> ORGANISM: Homo sapiens

<400> SEQUENCE: 143

Thr Ser Arg Phe Leu Cys Gln Arg Pro Asp Gly Ala Leu Tyr Gly
1               5                   10                  15

<210> SEQ ID NO 144
<211> LENGTH: 15
<212> TYPE: PRT
<213> ORGANISM: Mus musculus

<400> SEQUENCE: 144

Ala Ser Arg Phe Leu Cys Gln Gln Pro Asp Gly Ala Leu Tyr Gly
1               5                   10                  15

<210> SEQ ID NO 145
<211> LENGTH: 16
<212> TYPE: PRT
<213> ORGANISM: Homo sapiens

<400> SEQUENCE: 145

Ser Gly Phe Tyr Val Ala Met Asn Arg Arg Gly Arg Leu Tyr Gly Ser
1               5                   10                  15

<210> SEQ ID NO 146
<211> LENGTH: 16
<212> TYPE: PRT
<213> ORGANISM: Homo sapiens

<400> SEQUENCE: 146

Ser Arg Arg Tyr Leu Cys Met Asp Phe Arg Gly Asn Ile Phe Gly Ser
1               5                   10                  15

<210> SEQ ID NO 147
<211> LENGTH: 16
<212> TYPE: PRT
<213> ORGANISM: Mus musculus

<400> SEQUENCE: 147

Thr Arg Arg Phe Leu Cys Met Asp Leu His Gly Asn Ile Phe Gly Ser
1               5                   10                  15

<210> SEQ ID NO 148
<211> LENGTH: 8
<212> TYPE: PRT
<213> ORGANISM: Homo sapiens
```

```
<400> SEQUENCE: 148

Gly Leu Lys Lys Asn Gly Ser Cys
 1               5

<210> SEQ ID NO 149
<211> LENGTH: 8
<212> TYPE: PRT
<213> ORGANISM: Homo sapiens

<400> SEQUENCE: 149

Ala Leu Lys Arg Thr Gly Gln Tyr
 1               5

<210> SEQ ID NO 150
<211> LENGTH: 8
<212> TYPE: PRT
<213> ORGANISM: Homo sapiens

<400> SEQUENCE: 150

Ser Val Asn Gly Lys Gly Arg Pro
 1               5

<210> SEQ ID NO 151
<211> LENGTH: 9
<212> TYPE: PRT
<213> ORGANISM: Homo sapiens

<400> SEQUENCE: 151

Ile Ala Leu Ser Lys Asn Gly Lys Thr
 1               5

<210> SEQ ID NO 152
<211> LENGTH: 9
<212> TYPE: PRT
<213> ORGANISM: Mus musculus

<400> SEQUENCE: 152

Met Ala Leu Ser Lys Asn Gly Arg Thr
 1               5

<210> SEQ ID NO 153
<211> LENGTH: 9
<212> TYPE: PRT
<213> ORGANISM: Bos taurus

<400> SEQUENCE: 153

Ile Ala Leu Ser Lys Asn Gly Lys Ala
 1               5

<210> SEQ ID NO 154
<211> LENGTH: 8
<212> TYPE: PRT
<213> ORGANISM: Homo sapiens

<400> SEQUENCE: 154

Ala Leu Asn Lys Arg Gly Lys Ala
 1               5

<210> SEQ ID NO 155
<211> LENGTH: 8
<212> TYPE: PRT
<213> ORGANISM: Homo sapiens

<400> SEQUENCE: 155

Ala Leu Ser Lys Tyr Gly Arg Val
```

```
<210> SEQ ID NO 156
<211> LENGTH: 8
<212> TYPE: PRT
<213> ORGANISM: Homo sapiens

<400> SEQUENCE: 156

Ala Leu Asn Gln Lys Gly Ile Pro
1               5

<210> SEQ ID NO 157
<211> LENGTH: 8
<212> TYPE: PRT
<213> ORGANISM: Rattus spp.

<400> SEQUENCE: 157

Ala Leu Asn Gln Lys Gly Leu Pro
1               5

<210> SEQ ID NO 158
<211> LENGTH: 8
<212> TYPE: PRT
<213> ORGANISM: Homo sapiens

<400> SEQUENCE: 158

Ala Phe Thr Arg Lys Gly Arg Pro
1               5

<210> SEQ ID NO 159
<211> LENGTH: 8
<212> TYPE: PRT
<213> ORGANISM: Homo sapiens

<400> SEQUENCE: 159

Ala Leu Asn Lys Asp Gly Thr Pro
1               5

<210> SEQ ID NO 160
<211> LENGTH: 9
<212> TYPE: PRT
<213> ORGANISM: Homo sapiens

<400> SEQUENCE: 160

Ala Leu Asn Gly Lys Gly Ala Pro Arg
1               5

<210> SEQ ID NO 161
<211> LENGTH: 8
<212> TYPE: PRT
<213> ORGANISM: Homo sapiens

<400> SEQUENCE: 161

Gly Leu Asp Lys Glu Gly Gln Val
1               5

<210> SEQ ID NO 162
<211> LENGTH: 8
<212> TYPE: PRT
<213> ORGANISM: Mus musculus

<400> SEQUENCE: 162

Gly Leu Asp Lys Glu Gly Arg Val
1               5
```

```
<210> SEQ ID NO 163
<211> LENGTH: 8
<212> TYPE: PRT
<213> ORGANISM: Homo sapiens

<400> SEQUENCE: 163

Gly Leu Asn Lys Glu Gly Gln Ile
1               5

<210> SEQ ID NO 164
<211> LENGTH: 8
<212> TYPE: PRT
<213> ORGANISM: Homo sapiens

<400> SEQUENCE: 164

Gly Leu Asn Lys Glu Gly Glu Ile
1               5

<210> SEQ ID NO 165
<211> LENGTH: 8
<212> TYPE: PRT
<213> ORGANISM: Homo sapiens

<400> SEQUENCE: 165

Gly Leu Asn Lys Glu Gly Gln Ala
1               5

<210> SEQ ID NO 166
<211> LENGTH: 8
<212> TYPE: PRT
<213> ORGANISM: Mus musculus

<400> SEQUENCE: 166

Gly Leu Asn Lys Glu Gly Gln Val
1               5

<210> SEQ ID NO 167
<211> LENGTH: 8
<212> TYPE: PRT
<213> ORGANISM: Homo sapiens

<400> SEQUENCE: 167

Ala Leu Asn Lys Asp Gly Ser Pro
1               5

<210> SEQ ID NO 168
<211> LENGTH: 7
<212> TYPE: PRT
<213> ORGANISM: Homo sapiens

<400> SEQUENCE: 168

Ala Phe Thr Arg Gln Gly Arg
1               5

<210> SEQ ID NO 169
<211> LENGTH: 8
<212> TYPE: PRT
<213> ORGANISM: Homo sapiens

<400> SEQUENCE: 169

Gly Leu Lys Lys Asn Gly Ser Cys
1               5

<210> SEQ ID NO 170
<211> LENGTH: 8
<212> TYPE: PRT
```

<213> ORGANISM: Mus musculus

<400> SEQUENCE: 170

Gly Phe Thr Lys Lys Gly Arg Pro
1               5

<210> SEQ ID NO 171
<211> LENGTH: 8
<212> TYPE: PRT
<213> ORGANISM: Homo sapiens

<400> SEQUENCE: 171

Ala Leu Asn Lys Asp Gly Thr Pro
1               5

<210> SEQ ID NO 172
<211> LENGTH: 9
<212> TYPE: PRT
<213> ORGANISM: Homo sapiens

<400> SEQUENCE: 172

Ala Leu Asp Arg Arg Gly Gly Pro Arg
1               5

<210> SEQ ID NO 173
<211> LENGTH: 9
<212> TYPE: PRT
<213> ORGANISM: Mus musculus

<400> SEQUENCE: 173

Ala Leu Asp Ser Gln Gly Ile Pro Arg
1               5

<210> SEQ ID NO 174
<211> LENGTH: 7
<212> TYPE: PRT
<213> ORGANISM: Homo sapiens

<400> SEQUENCE: 174

Ala Met Asp Thr Asp Gly Leu
1               5

<210> SEQ ID NO 175
<211> LENGTH: 7
<212> TYPE: PRT
<213> ORGANISM: Mus musculus

<400> SEQUENCE: 175

Ala Met Asp Thr Glu Gly Leu
1               5

<210> SEQ ID NO 176
<211> LENGTH: 7
<212> TYPE: PRT
<213> ORGANISM: Sus scrofa

<400> SEQUENCE: 176

Ala Met Asp Thr Ser Gly Leu
1               5

<210> SEQ ID NO 177
<211> LENGTH: 7
<212> TYPE: PRT
<213> ORGANISM: Homo sapiens

<400> SEQUENCE: 177

```
Ala Met Lys Glu Asp Gly Arg
1               5

<210> SEQ ID NO 178
<211> LENGTH: 7
<212> TYPE: PRT
<213> ORGANISM: Homo sapiens

<400> SEQUENCE: 178

Ala Met Asn Lys Arg Gly Arg
1               5

<210> SEQ ID NO 179
<211> LENGTH: 7
<212> TYPE: PRT
<213> ORGANISM: Homo sapiens

<400> SEQUENCE: 179

Ala Met Ser Ser Lys Gly Lys
1               5

<210> SEQ ID NO 180
<211> LENGTH: 7
<212> TYPE: PRT
<213> ORGANISM: Mus musculus

<400> SEQUENCE: 180

Ala Met Ser Ser Arg Gly Lys
1               5

<210> SEQ ID NO 181
<211> LENGTH: 7
<212> TYPE: PRT
<213> ORGANISM: Gallus gallus

<400> SEQUENCE: 181

Ala Met Asn Ser Lys Gly Lys
1               5

<210> SEQ ID NO 182
<211> LENGTH: 7
<212> TYPE: PRT
<213> ORGANISM: Homo sapiens

<400> SEQUENCE: 182

Ala Met Ser Lys Lys Gly Lys
1               5

<210> SEQ ID NO 183
<211> LENGTH: 7
<212> TYPE: PRT
<213> ORGANISM: Homo sapiens

<400> SEQUENCE: 183

Ala Met Asn Ser Lys Gly Arg
1               5

<210> SEQ ID NO 184
<211> LENGTH: 7
<212> TYPE: PRT
<213> ORGANISM: Mus musculus

<400> SEQUENCE: 184

Ala Met Asn Lys Glu Gly Lys
1               5
```

```
<210> SEQ ID NO 185
<211> LENGTH: 7
<212> TYPE: PRT
<213> ORGANISM: Homo sapiens

<400> SEQUENCE: 185

Ala Met Asn Lys Glu Gly Lys
1               5

<210> SEQ ID NO 186
<211> LENGTH: 7
<212> TYPE: PRT
<213> ORGANISM: Rattus spp.

<400> SEQUENCE: 186

Ala Met Asn Lys Gln Gly Leu
1               5

<210> SEQ ID NO 187
<211> LENGTH: 7
<212> TYPE: PRT
<213> ORGANISM: Homo sapiens

<400> SEQUENCE: 187

Cys Met Asn Lys Lys Gly Lys
1               5

<210> SEQ ID NO 188
<211> LENGTH: 7
<212> TYPE: PRT
<213> ORGANISM: Homo sapiens

<400> SEQUENCE: 188

Gly Met Asn Glu Lys Gly Glu
1               5

<210> SEQ ID NO 189
<211> LENGTH: 7
<212> TYPE: PRT
<213> ORGANISM: Homo sapiens

<400> SEQUENCE: 189

Ala Met Asn Lys Lys Gly Lys
1               5

<210> SEQ ID NO 190
<211> LENGTH: 7
<212> TYPE: PRT
<213> ORGANISM: Homo sapiens

<400> SEQUENCE: 190

Ala Met Asn Ala Glu Gly Leu
1               5

<210> SEQ ID NO 191
<211> LENGTH: 7
<212> TYPE: PRT
<213> ORGANISM: Homo sapiens

<400> SEQUENCE: 191

Ala Met Asn Gly Glu Gly Tyr
1               5

<210> SEQ ID NO 192
```

```
<211> LENGTH: 7
<212> TYPE: PRT
<213> ORGANISM: Homo sapiens

<400> SEQUENCE: 192

Ala Met Asn Ser Glu Gly Tyr
1               5

<210> SEQ ID NO 193
<211> LENGTH: 7
<212> TYPE: PRT
<213> ORGANISM: Homo sapiens

<400> SEQUENCE: 193

Ala Met Asn Gly Glu Gly Tyr
1               5

<210> SEQ ID NO 194
<211> LENGTH: 7
<212> TYPE: PRT
<213> ORGANISM: Mus musculus

<400> SEQUENCE: 194

Cys Met Ser Ala Asp Gly Lys
1               5

<210> SEQ ID NO 195
<211> LENGTH: 7
<212> TYPE: PRT
<213> ORGANISM: Homo sapiens

<400> SEQUENCE: 195

Gly Met Asn Glu Arg Gly Glu
1               5

<210> SEQ ID NO 196
<211> LENGTH: 7
<212> TYPE: PRT
<213> ORGANISM: Homo sapiens

<400> SEQUENCE: 196

Cys Met Asn Lys Arg Gly Lys
1               5

<210> SEQ ID NO 197
<211> LENGTH: 7
<212> TYPE: PRT
<213> ORGANISM: Homo sapiens

<400> SEQUENCE: 197

Cys Met Asn Arg Lys Gly Lys
1               5

<210> SEQ ID NO 198
<211> LENGTH: 7
<212> TYPE: PRT
<213> ORGANISM: Homo sapiens

<400> SEQUENCE: 198

Cys Met Gly Ala Asp Gly Lys
1               5

<210> SEQ ID NO 199
<211> LENGTH: 7
<212> TYPE: PRT
<213> ORGANISM: Homo sapiens
```

```
<400> SEQUENCE: 199

Gly Met Asn Asp Lys Gly Glu
1               5

<210> SEQ ID NO 200
<211> LENGTH: 7
<212> TYPE: PRT
<213> ORGANISM: Homo sapiens

<400> SEQUENCE: 200

Leu Cys Gln Arg Pro Asp Gly
1               5

<210> SEQ ID NO 201
<211> LENGTH: 7
<212> TYPE: PRT
<213> ORGANISM: Mus musculus

<400> SEQUENCE: 201

Leu Cys Gln Gln Pro Asp Gly
1               5

<210> SEQ ID NO 202
<211> LENGTH: 7
<212> TYPE: PRT
<213> ORGANISM: Homo sapiens

<400> SEQUENCE: 202

Cys Met Asp Phe Arg Gly Asn
1               5

<210> SEQ ID NO 203
<211> LENGTH: 7
<212> TYPE: PRT
<213> ORGANISM: Mus musulus

<400> SEQUENCE: 203

Cys Met Asp Leu His Gly Asn
1               5

<210> SEQ ID NO 204
<211> LENGTH: 7
<212> TYPE: PRT
<213> ORGANISM: Homo sapiens

<400> SEQUENCE: 204

Ala Met Asn Arg Arg Gly Arg
1               5

<210> SEQ ID NO 205
<211> LENGTH: 10
<212> TYPE: PRT
<213> ORGANISM: Artificial sequence
<220> FEATURE:
<223> OTHER INFORMATION: Suggested active motif
<220> FEATURE:
<221> NAME/KEY: VARIANT
<222> LOCATION: (5)..(9)
<223> OTHER INFORMATION: each Xaa is absent or is any amino acid

<400> SEQUENCE: 205

Ala Glu Asn Gln Xaa Xaa Xaa Xaa Xaa Gly
1               5                   10

<210> SEQ ID NO 206
```

```
<211> LENGTH: 7
<212> TYPE: PRT
<213> ORGANISM: Artificial sequence
<220> FEATURE:
<223> OTHER INFORMATION: suggested active motif
<220> FEATURE:
<221> NAME/KEY: VARIANT
<222> LOCATION: (5)..(6)
<223> OTHER INFORMATION: each Xaa is absent or is any amino acid

<400> SEQUENCE: 206

Ala Glu Asn Gln Xaa Xaa Lys
1               5

<210> SEQ ID NO 207
<211> LENGTH: 15
<212> TYPE: PRT
<213> ORGANISM: Artificial sequence
<220> FEATURE:
<223> OTHER INFORMATION: Ala substituted variant

<400> SEQUENCE: 207

Glu Val Tyr Val Val Ala Glu Asn Ala Ala Gly Lys Ser Lys Ala
1               5                   10                  15

<210> SEQ ID NO 208
<211> LENGTH: 7
<212> TYPE: PRT
<213> ORGANISM: Artificial sequence
<220> FEATURE:
<223> OTHER INFORMATION: Ala substituted variant

<400> SEQUENCE: 208

Ala Ala Asn Gln Gln Gly Lys
1               5

<210> SEQ ID NO 209
<211> LENGTH: 7
<212> TYPE: PRT
<213> ORGANISM: Artificial sequence
<220> FEATURE:
<223> OTHER INFORMATION: Ala substituted variant

<400> SEQUENCE: 209

Ala Glu Ala Gln Gln Gly Lys
1               5

<210> SEQ ID NO 210
<211> LENGTH: 7
<212> TYPE: PRT
<213> ORGANISM: Artificial sequence
<220> FEATURE:
<223> OTHER INFORMATION: Ala substituted variant

<400> SEQUENCE: 210

Ala Glu Asn Ala Gln Gly Lys
1               5

<210> SEQ ID NO 211
<211> LENGTH: 7
<212> TYPE: PRT
<213> ORGANISM: Artificial sequence
<220> FEATURE:
<223> OTHER INFORMATION: Ala substituted variant

<400> SEQUENCE: 211

Ala Glu Asn Gln Gln Ala Lys
1               5
```

```
<210> SEQ ID NO 212
<211> LENGTH: 7
<212> TYPE: PRT
<213> ORGANISM: Artificial sequence
<220> FEATURE:
<223> OTHER INFORMATION: Ala substituted variant

<400> SEQUENCE: 212

Ala Glu Asn Gln Gln Gly Ala
1               5

<210> SEQ ID NO 213
<211> LENGTH: 7
<212> TYPE: PRT
<213> ORGANISM: Artificial sequence
<220> FEATURE:
<223> OTHER INFORMATION: Ala substituted variant

<400> SEQUENCE: 213

Ala Ala Lys Glu Asp Gly Arg
1               5

<210> SEQ ID NO 214
<211> LENGTH: 7
<212> TYPE: PRT
<213> ORGANISM: Artificial sequence
<220> FEATURE:
<223> OTHER INFORMATION: Ala substituted variant

<400> SEQUENCE: 214

Ala Met Ala Glu Asp Gly Arg
1               5

<210> SEQ ID NO 215
<211> LENGTH: 7
<212> TYPE: PRT
<213> ORGANISM: Artificial sequence
<220> FEATURE:
<223> OTHER INFORMATION: Ala substituted variant

<400> SEQUENCE: 215

Ala Met Lys Ala Asp Gly Arg
1               5

<210> SEQ ID NO 216
<211> LENGTH: 7
<212> TYPE: PRT
<213> ORGANISM: Artificial sequence
<220> FEATURE:
<223> OTHER INFORMATION: Ala substituted variant

<400> SEQUENCE: 216

Ala Met Lys Glu Ala Gly Arg
1               5

<210> SEQ ID NO 217
<211> LENGTH: 7
<212> TYPE: PRT
<213> ORGANISM: Artificial sequence
<220> FEATURE:
<223> OTHER INFORMATION: Ala substituted variant

<400> SEQUENCE: 217

Ala Met Lys Glu Asp Ala Arg
1               5

<210> SEQ ID NO 218
```

-continued

<211> LENGTH: 7
<212> TYPE: PRT
<213> ORGANISM: Artificial sequence
<220> FEATURE:
<223> OTHER INFORMATION: Ala substituted variant

<400> SEQUENCE: 218

Ala Met Lys Glu Asp Gly Ala
1               5